(12) United States Patent
Okazawa

(10) Patent No.: US 11,623,946 B2
(45) Date of Patent: Apr. 11, 2023

(54) DIAGNOSIS METHODS, DIAGNOSTIC AGENTS, AND THERAPEUTIC AGENTS AGAINST ALZHEIMER'S DISEASE AND FRONTOTEMPORAL LOBAR DEGENERATION, AND SCREENING METHODS FOR THESE AGENTS

(71) Applicant: National University Corporation Tokyo Medical and Dental University, Tokyo (JP)

(72) Inventor: Hitoshi Okazawa, Tokyo (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 0 days.

(21) Appl. No.: 15/107,502

(22) PCT Filed: Dec. 25, 2014

(86) PCT No.: PCT/JP2014/084424
§ 371 (c)(1),
(2) Date: Sep. 23, 2016

(87) PCT Pub. No.: WO2015/099094
PCT Pub. Date: Jul. 2, 2015

(65) Prior Publication Data
US 2017/0182012 A1 Jun. 29, 2017

(30) Foreign Application Priority Data
Dec. 27, 2013 (JP) .............................. JP2013-272189

(51) Int. Cl.
| C07K 14/47 | (2006.01) |
| C12Q 1/48 | (2006.01) |
| G01N 33/68 | (2006.01) |
| A61K 31/44 | (2006.01) |
| A61K 31/4439 | (2006.01) |
| A61K 31/506 | (2006.01) |
| A61K 38/16 | (2006.01) |
| A61K 38/02 | (2006.01) |
| A61K 31/437 | (2006.01) |

(52) U.S. Cl.
CPC .......... *C07K 14/4703* (2013.01); *A61K 31/44* (2013.01); *A61K 31/4439* (2013.01); *A61K 31/506* (2013.01); *A61K 38/02* (2013.01); *A61K 38/16* (2013.01); *C12Q 1/485* (2013.01); *G01N 33/6896* (2013.01); *A61K 31/437* (2013.01); *G01N 2500/04* (2013.01); *G01N 2500/20* (2013.01); *G01N 2800/2821* (2013.01)

(58) Field of Classification Search
CPC combination set(s) only.
See application file for complete search history.

(56) References Cited

U.S. PATENT DOCUMENTS

| 2005/0059092 A1 | 3/2005 | Zhao et al. |
| 2012/0094991 A1 | 4/2012 | D'Mello et al. |
| 2013/0139925 A1 | 8/2013 | Huentelman |

FOREIGN PATENT DOCUMENTS

| JP | 2012500220 A | 1/2012 | |
| WO | 02067764 | 9/2002 | |
| WO | WO 02067764 A2 * | 9/2002 | ......... G01N 33/6896 |
| WO | 2012006640 | 1/2012 | |
| WO | WO 2012006640 A2 * | 1/2012 | ........... A61K 38/162 |

OTHER PUBLICATIONS

Hasegawa et al.: Microglia signaling by amyloid _ protein through mitogen-activated protein kinase mediated phosphorylation of MARCKS, NeuroReport, vol. 12, No. 11, Aug. 8, 2001 (2001), pp. 2567-2571.*
Allen et al., Inhibition of MARCS Phosphorylation Improves Working Memory, Alzheimer's & Dementia: The Journal of the Alzheimer's Association, Jul. 2010, pp. S581, vol. 6, Issue 4, Supplement.*
Nakai et al., Amyloid Protein(25-35) Phosphorylates MARCKS Through Tyrosine Kinase-Activated Protein Kinase C Signaling Pathway in Microglia, J. Neurochem., vol. 72, No. 3, Mar. 1999 (Mar. 1999), pp. 1179-1186.*
Aaltonen et al., PKC$\alpha/\beta$ I Inhibitor G06976 Induces Dephosphorylation of Constitutively Hyperphosphorylated Rb and G1 Arrest in T24 Cells, Anticancer Research 30: 3995-4000 (2010).*
Kang et al., Protein kinase C (PKC) isozyme-specific substrates and their design, Biotechnology Advances 30 (2012) 1662-1672.*
Banks, Characteristics of compounds that cross the blood-brain barrier, BMC Neurology, 2009, 9 (Suppl I):S3.*
Frisoni, The clinical use of structural MRI in Alzheimer disease, Nature Reviews Neurology, vol. 6, pp. 67-77(2010) (Abstract).*

(Continued)

*Primary Examiner* — Adam Weidner
(74) *Attorney, Agent, or Firm* — Sughrue Mion, PLLC

(57) ABSTRACT

It has been revealed that, from a pre-onset stage of Alzheimer's disease, enhancement of phosphorylations of MARCKS and the like causes abnormal spine formation or the like, consequently developing the disease. Moreover, it has also been revealed that the phosphorylations of MARCKS and the like are caused by PKC and the like, and further that b-raf is involved in the phosphorylation of a tau protein important for the progression of Alzheimer's disease. Thus, these proteins have been found to be target molecules useful in the diagnosis and treatment of Alzheimer's disease. In addition, it has also been revealed that, pre-onset in a stage of frontotemporal lobar degeneration also, b-RAF phosphorylation enhancement causes a decrease in the number of spines and the like, consequently developing the disease. Thus, b-RAF has been found to be a target molecule useful in the diagnosis and treatment of frontotemporal lobar degeneration.

3 Claims, 32 Drawing Sheets
(1 of 32 Drawing Sheet(s) Filed in Color)

(56) References Cited

OTHER PUBLICATIONS

Stanford "Alzheimer's Prevention, Treatment and Research—A Q&A with Dr. Frank Longo" accessed from stanfordhealthcare.org on May 3, 2016 (Year: 2016).*
Communication, dated Aug. 21, 2017, issued by the European Patent Office in European Application No. 14875056.5.
Hasegawa et al., "Microglial Signaling by Amyloid Beta Protein Through Mitogen-Activated Protein Kinase Mediating Phosphorylation of MARKS", Neuroreport, 12(11):2567-2571 (2001).
Eliezer Masliah, et al., "Rapid Communication, Casein Kinase II Alteration Precedes Tau Accumulation in Tangle Formation", American Journal of Pathology, Feb. 1992, pp. 263-268, vol. 140, No. 2.
Mikio Shoji, et al., "JNK activation is associated with intracellular β-amyloid accumulation", Molecular Brian Research, 2001, pp. 221-233, vol. 85.
Xiongwei Zhu, et al., "JKK1, an upstream activator of JNK/SAPK, is activated in Alzheimer's disease", Journal of Neurochemistry, 2003, pp. 87-93, vol. 85.
Akihiko Takashima, et al., "tau protein kinase I is essential for amyloid β-protein-induced neurotoxicity", Proc. Natl. Acad. Sci., Aug. 1993, pp. 7789-7793, vol. 90.
Diane P. Hanger, et al., "Novel Phosphorylation Sites in Tau from Alzheimer Brain Supporta Role for Casein Kinase 1 in Disease Pathogenesis", The Journal of Biological Chemistry, Aug. 10, 2007, pp. 23645-23654, vol. 282, No. 32.
Jian-Zhi Wang, et al., "Kinases and phosphatases and tau sites involved in Alzheimer neurofibrillary degeneration", Eur. J. Neurosci., Jan. 2007, pp. 59-68, vol. 25(1).
Diego Piedrahita, et al., "Silencing of CDK5 Reduces Nurofibrillary Tangles in Transgenic Alzheimer's Mice", J. Neurosci., Oct. 20, 2010, pp. 13966-13976, vol. 30(42).
Alejandra Del C. Alonso, et al., "Role of abnormally phosphorylated tau in the breakdown of microtubules in Alzheimer disease", Proc. Natl. Acad. Sci., Jun. 1994, pp. 5562-5566, vol. 91.
Khalid Iqbal, et al., "Defective Brain Microtubule Assembly in Alzheimer's Disease", The Lancet, Aug. 23, 1986, pp. 421-426, vol. 2.
Asa Abeliovich, et al., "Modified Hippocampal Long-Term Potentiation in PKCγ-Mutant Mice", Cell, Dec. 31, 1993, pp. 1253-1262, vol. 75.
Asa Abeliovich, et al., "PKCγ Mutant Mice Exhibit Mild Deficits in Spatial and Contextual Learning", Cell, Dec. 31, 1993, pp. 1263-1271, vol. 75.
Caitlin A. Orsini, et al., "Neural and Cellular Mechanisms of Fear and Extinction Memory Formation", Neurosci. Biobehav. Rev., Aug. 2012, pp. 1773-1802, vol. 36(7).
Daniel L. Alkon, et al., "PKC signaling deficits: a mechanistic hypothesis for the origins of Alzheimer's disease", Trends Pharmacol. Sci., 2007, pp. 51-60, vol. 28, No. 2.
S. G. Birnbaum, et al., "Protein Kinase C Overactivity Impairs Prefrontal Cortical Regulation of Working Memory", Science, Oct. 29, 2004, pp. 882-884, vol. 306.
Rui Su, et al., "A possible role of myristoylated alanine-rich C kinase substrate in endocytic pathway of Alzheimer's disease", Neurosci. Bull., Aug. 1, 2010, pp. 338-344, vol. 26(4).
Takemi Kimura, "Phosphorylation of MARCKS in Alzheimer disease brains", Neuroreport, Mar. 20, 2000, pp. 869-873, vol. 11, No. 4.
Wei Tang, et al., "The Growth Factor Progranulin Binds to TNF Receptors and Is Therapeutic Against Inflammatory Arthritis in Mice", Science, Apr. 22, 2011, pp. 478-484, vol. 332(6028).
Xi Chen, et al., "Progranulin Does Not Bind Tumor Necrosis Factor (TNF) Receptors and Is Not a Direct Regulator of TNF-Dependent Signaling or Bioactivity in Immune or Neuronal Cells", The Journal of Neuroscience, May 22, 2013, pp. 9202-9213, vol. 33(21).
Jinlong Jian, et al., "Progranulin directly binds to the CRD2 and CRD3 of TNFR extracellular domains", FEBS Letters, 2013, pp. 3428-3436, vol. 587.
Nima Etemadi, et al., "Progranulin does not inhibit TNF and lymphotoxin-α signalling through TNF receptor 1", Immunology and Cell Biology, 2013, pp. 661-664, vol. 91.
Ya Hu, et al., "Progranulin promotes tumour necrosis factor-induced proliferation of suppressive mouse $CD_4^+$ $Foxp_3^+$ regulatory T cells", Immunology, 2014, pp. 193-201, vol. 142.
Lauren Herl Martens, et al., "Progranulin deficiency promotes neuroinflammation and neuron loss following toxin-induced injury", The Journal of Clinical Investigation, Nov. 2012, pp. 3955-3959, vol. 122, No. 11.
Fangfang Yin, et al., "Behavioral deficits and progressive neuropathology in progranulin-deficient mice: a mouse model of frontotemporal dementia", The FASEB Journal, Aug. 2016, pp. 4639-4647, vol. 24, No. 12.
Fangfang Yin, et al., "Exaggerated inflammation, impaired host defense, and neuropathology in progranulin-deficient mice", J. Exp. Med., Dec. 21, 2009, pp. 117-128, vol. 207, No. 1.
Hans Wils, et al., "Cellular ageing, increased mortality and FTLD-TDP-associated neuropathology in progranulin knockout mice", Journal of Pathology, 2012, pp. 67-76, vol. 228.
Terri L. Petkau, et al., "Synaptic dysfunction in progranulin-deficient mice", Neurobiology of Disease, 2012, pp. 711-722, vol. 45.
Zeshan Ahmed, et al., "Accelerated Lipofuscinosis and Ubiquitination in Granulin Knockout Mice Suggest a Role for Progranulin in Successful Aging", Neurobiology, Jul. 2010, pp. 311-324, vol. 177, No. 1.
N. Ghoshal, et al., "Core features of frontotemporal dementia recapitulated in progranulin knockout mice", Neurobiol. Dis., Jan. 2012, pp. 395-408, vol. 45(1).
Takashi Saito, et al., "Single Appknock-in mouse models of Alzheimer's disease", Nature Neuroscience, May 2014, pp. 661-663, vol. 17, No. 5.
Justyna Maria Czarna Bahl, et al., "Characterization of the Human Cerebrospinal Fluid Phosphoproteome by Titanium Dioxide Affinity Chromatography and Mass Spectrometry", Anal. Chem., 2008, pp. 6308-6316, vol. 80.
Masamichi Nakai, et al., "Amyloid β Protein (25-35)Phosphorylates MARCKS Through Tyrosine Kinase-Activated Protein Kinase C Signaling Pathway in Microglia" Journal of Neurochemistry, 1999, pp. 1179-1186, vol. 72, No. 3.
April N. Allen, et al., "Inhibition of MARCKS Phosphorylation Improves Working Memory", Alzheimer's & Dementia: The Journal of the Alzheimer's Association, Jul. 2010, pp. S581, vol. 6, Issue 4, Supplement.
Written Opinion for PCT/JP2014/084424 dated Apr. 7, 2015 [PCT/ISA/237].

* cited by examiner

Fig. 34

DIAGNOSIS METHODS, DIAGNOSTIC AGENTS, AND THERAPEUTIC AGENTS AGAINST ALZHEIMER'S DISEASE AND FRONTOTEMPORAL LOBAR DEGENERATION, AND SCREENING METHODS FOR THESE AGENTS

CROSS REFERENCE TO RELATED APPLICATIONS

This application is a National Stage of International Application No. PCT/JP2014/084424, filed on Dec. 25, 2014, which claims priority from Japanese Patent Application No. 2013-272189, filed on Dec. 27, 2013, the contents of all of which are incorporated herein by reference their entirety.

TECHNICAL FIELD

The present invention relates to a diagnosis method, a diagnostic agent, and a therapeutic agent against Alzheimer's disease. Further, the present invention relates to a screening method for candidate compounds of these agents. Moreover, the present invention relates to a diagnostic agent and a therapeutic agent against frontotemporal lobar degeneration.

BACKGROUND ART

Alzheimer's disease (Alzheimer's dementia, AD) is a progressive neurodegenerative disease that may occur in presenile to senile stages. The main symptoms include memory disorder, higher brain function disorders (aphasia, apraxia, agnosia, constructional apraxia), change in personality, and so forth. In addition, because of such symptoms, the disease not only reduces the quality of life of a patient himself/herself, but also greatly influences the living styles of family and so on around the patient. Further, the number of the patients is steadily increasing along with population ageing. Alzheimer's disease is a serious problem of modern society all over the world. Hence, Alzheimer's disease has been studied actively, but the elucidation of the full onset mechanism thereof and the development of an eradicative medicine have not been achieved yet under current situations.

On the other hand, it is now possible to delay the progression of Alzheimer's disease symptoms more than ever. Particularly, cholinesterase inhibitors have been actually used in clinical settings, resulting in some reasonable outcomes. The progression of the symptoms can also be suppressed to some degree currently. As a result, there is a demand in the treatment of Alzheimer's disease that the disease should be detected at earlier stages, thereby hastening developments of: electroencephalography, biochemical tests targeting blood and cerebrospinal fluid, diagnostic imagings such as CT, MRI, and PET/SPECT, and so forth. Particularly, PET is about to enable the detection of senile plaque (amyloid plaque) deposition in the brain, which is a characteristic of Alzheimer's disease and the most likely causative factor thereof. However, currently-available diagnostic techniques still have difficulty grasping a pre-onset stage of Alzheimer's disease is developed, and no effective early-stage diagnosis method has been established yet under current situations.

Besides senile plaque deposition, Alzheimer's disease is neuropathologically characterized also by neurofibrillary tangle (paired helical filament (PHF)) deposition. In addition, the deposition of these structures is believed to cause nerve function disorder and nerve cell death (nerve cell dropout) involved in the symptoms described above. Moreover, it has been revealed that senile plaques are structures formed when polypeptides, each composed of approximately 40 amino acids, called amyloid β (Aβ) aggregate and deposit outside nerve cells in high density. Further, neurofibrillary tangles have been revealed to be also structures formed when microtubule-associated proteins tau are phosphorylated and thereby dissociated from cytoskeleton-forming microtubules, followed by polymerization among the tau proteins. Meanwhile, although no conclusion has been drawn yet regarding the Alzheimer causative factor and onset mechanism, the most likely mechanism is such that when amyloid ρ molecules aggregate (amyloid pathology), the aggregation promotes the tau phosphorylation and polymerization (tau pathology), consequently leading to nerve cell death and so forth (amyloid cascade hypothesis).

Furthermore, it is suggested that various phosphorylation signal transductions are involved in a pathology of Alzheimer's disease. For example, as described above, the deposition of neurofibrillary tangles is due to tau phosphorylation. It is also revealed that this tau phosphorylation is regulated by various serine/threonine kinases such as GSK3β, JNK, PKA, Cdk5, and casein kinase II (NPLs 1 to 7). Moreover, it has been presumed that microtubules from which tau is dissociated by such phosphorylation become unstable, consequently decreasing neurites as observed in the brains of AD patients (NPLs 8 and 9).

In addition, it is suggested that a phosphorylation enzyme PKC is involved in memory formation (NPLs 10 and 11). Further, activating PKC and CaMKII is believed to promote the transcriptions of BDNF and Arc involved in memory control, and also have a protective function against Alzheimer's disease (NPLs12 and 13). Additionally, based on such findings, an attempt has been made to apply PKC activators such as bryostatin in the treatment of Alzheimer's disease. However, it is also reported that an excessive activation of PKC, on the other hand, impairs working memory (NPL 14).

Furthermore, it is also suggested that the phosphorylation of MARCKS by PKC dissociates this protein from the cell membrane (PIP2 and actins) and, as a result, induces amyloid β production (NPL 15). Moreover, phosphorylated MARCKS is observed in dystrophic neurites and microglia within senile plaques. Nevertheless, it has also been revealed that the phosphorylation level of MARCKS in the brains of Al disease patients is lower than that of healthy subjects (NPL 16).

As described above, it has been suggested that phosphorylation signal transductions are involved in a pathology of Alzheimer's disease. If this involvement can be elucidated in more details, it is expected to greatly contribute to establishments of early-stage diagnosis and treatment methods against this disease.

Nonetheless, in a phosphorylation signal transduction, particularly, in a wide variety of phosphorylation signal transductions in Alzheimer's disease, what protein phosphorylations play a central role in a pre-onset stage of Alzheimer's disease has not been elucidated at all yet.

Meanwhile, frontotemporal lobar degeneration (FTLD) is known as a disease that exhibits progressive neurodegenerative disorders like Alzheimer's disease. Frontotemporal lobar degeneration is the second or third most frequent early-onset neurodegenerative dementia after Alzheimer's disease. The symptoms to be exhibited include drastic changes in behavior and personality. A language function disorder occurs together with FTLD in many cases, and gradually develops into a cognitive disorder and dementia. In addition, the studies have been conducted as in the case of Alzheimer's disease, but the full onset mechanism of FTLD has not been revealed yet.

For example, it is known that one cause of genetic frontotemporal lobar degeneration is a mutation in the PGRN gene. Moreover, there is a report that the PGRN protein exhibits an antagonistic action against TNF in binding to TNF receptors, suggesting that this antagonism is involved in the onset of frontotemporal lobar degeneration (NPL 17). However, on the other hand, contradictory results are also reported. The molecular mechanism in the onset of frontotemporal lobar degeneration, including the possibility of the involvement of the TNF signal transduction pathway (NPLs 18 to 21), has not been elucidated under current situations.

Additionally, for the elucidation of the molecular mechanism of frontotemporal lobar degeneration, PGRN gene knockout mice have been prepared as model animals. Moreover, findings (such as excessive inflammatory reaction, cellular ageing, synaptic dysfunction, ubiquitination promotion, increased caspase activation, decreased TDP-43 solubility) exhibited in frontotemporal lobar degeneration are actually observed in such knockout mice (NPLs 22 to 28). However, as has been pointed out in other neurodegenerative diseases such as Alzheimer's disease also (NPL 29), artificially reducing the amount of the PGRN protein in the model animals actually results in mere mimicking of symptoms caused by the expressions of mutated PGRN mRNA and the like, so that the effectiveness as model animals is questionable.

As has been described above, no effective model animal is developed against frontotemporal lobar degeneration, and the onset mechanism has not been elucidated as in the case of Alzheimer's disease. Hence, in the development of diagnosis and treatment methods against the disease, no useful target molecule has been found under current situations.

CITATION LIST

Non Patent Literatures

[NPL 1] Masliah, E. et al., Am. J. Pathol., 1992, Vol. 140, pp. 263 to 268
[NPL 2] Shoji, M. et al., Brain Res. Mol. Brain Res., 2000, Vol. 85, pp. 221 to 233
[NPL 3] Zhu, X. et al., J. Neurochem., 2003, Vol. 85, pp. 87 to 93
[NPL 4] Takashima, A. et al., Proc. Natl. Acad. Sci. U.S.A., 1993, Vol. 90, pp. 7789 to 7793
[NPL 5] Hanger, D. P. et al., J. Biol. Chem., 2007, Vol. 282, pp. 23645 to 23654
[NPL 6] Wang, J. Z. et al., Eur. J. Neurosci., 2007, Vol. 25, pp. 59 to 68
[NPL 7] Piedrahita, D. et al., J. Neurosci., 2010, Vol. 30, pp. 13966 to 13976
[NPL 8] Alonso, A. C. et al., Proc. Natl. Acad. Sci. U.S.A., 1994, Vol. 91, pp. 5562 to 5566
[NPL 9] Iqbal, K. et al., Lancet, 1986, Vol. 2, pp. 421 to 426
[NPL 10] Abeliovich, A. et al., Cell, 1993, Vol. 75, pp. 1253 to 1262
[NPL 11] Abeliovich, A. et al., Cell, 1993, Vol. 75, pp. 1263 to 1271
[NPL 12] Orsini, C. A. et al., Neurosci. Biobehay. Rev., Vol. 36, 2012, pp. 1773 to 1802
[NPL 13] Alkon, D. L. et al., Trends Pharmacol. Sci., 2007, Vol. 28, pp. 51 to 60
[NPL 14] Birnbaum, S. G. et al., Science., 2004, Vol. 29, pp. 882 to 884
[NPL 15] Rui S U et al., Neurosci Bull, 2010, Vol. 26, pp. 338 to 344
[NPL 16] Kimura T. et al., Neuroreport., 2000, Vol. 11, pp. 869 to 73
[NPL 17] Tang, W. et al., Science, 2011, Vol. 332, pp. 478 to 484
[NPL 18] Chen, X. et al., J. Neurosci., 2013, Vol. 33, pp. 9202 to 9213,
[NPL 19] Jian, J. et al., FEBS Lett., 2013, Vol. 587, pp. 3428 to 3436,
[NPL 20] Etemadi, N. et al., Immunol. Cell Biol., 2013, Vol. 91, pp. 661 to 664
[NPL 21] Hu, Y. et al., Immunology, 2014, Vol. 142, pp. 193 to 201
[NPL 22] Martens, L. H. et al., J. Clin. Invest., 2012, Vol. 122, pp. 3955 to 3959
[NPL 23] Yin, F. et al., FASEB J., 2010, Vol. 24, pp. 4639 to 4647
[NPL 24] Yin, F. et al., J. Exp. Med., 2010, Vol. 207, pp. 117 to 128
[NPL 25] Wils, H. et al., J. Pathol., 2012, Vol. 228, pp. 67 to 76
[NPL 26] Petkau, T. L. et al., Neurobiol. Dis., 2012, Vol. 45, pp. 711 to 722
[NPL 27] Ahmed, Z. et al., Am. J. Pathol., 2010, Vol. 177, pp. 311 to 324
[NPL 28] Ghoshal, N. et al., Neurobiol. Dis., 2012, Vol. 45, pp. 395 to 408
[NPL 29] Saito, T. et al., Nat. Neurosci., 2014, Vol. 17, pp. 661 to 663

SUMMARY OF INVENTION

Technical Problem

The present invention has been made in view of the problems of the above-described conventional techniques. An object of the present invention is to identify phosphoproteins and kinase proteins which play central roles in a pre-onset stage of Alzheimer's disease, as well as a network composed of these proteins, and consequently to provide target molecules useful in the diagnosis and treatment of Alzheimer's disease.

In addition, another object of the present invention is to identify a signal transduction pathway which plays a central role in a pre-onset stage of frontotemporal lobar degeneration, and consequently to provide target molecules useful in the diagnosis and treatment of frontotemporal lobar degeneration.

Solution to Problem

In order to provide target molecules useful in the diagnosis and treatment of Alzheimer's disease, the present inventor first employed an analysis according to a mass spectrometry method (2D LC MS/MS analysis) targeting brains at the pre-onset stage of tau model mice and four types of Alzheimer's disease (AD) model mice and on postmortem brains of AD patients, and searched 1100 or more phosphoproteins and 30000 or more phosphopolypeptides for proteins whose expression amounts changed in comparison with the respective wild-type mice and healthy subjects, for example.

As a result, phosphoproteins whose expressions changed immediately before or immediately after amyloid β started aggregating were successfully identified in the brains of multiple AD model mice. Further, it was revealed that the phosphorylations of most of these phosphoproteins also changed commonly in the AD patients or the tau model mice. In sum, MARCKS, Marcksl1, SRRM2, SPTA2, ADDB, NEUM, BASP1, SYT1, G3P, HS90A, CLH, NFH, NFL, GPRIN1, ACON, ATPA, and ATPB were successfully selected as proteins (AD core proteins) whose phosphorylation levels changed in brains affected with Alzheimer's disease, and which were presumed to play central roles in the pathology.

Further, these AD core proteins were incorporated into the experimentally verified protein-protein interaction (PPI) database for the analysis. Thus, an AD signaling network (AD core network) was identified which would serve as the core in the pathology of Alzheimer's disease.

The result surprisingly revealed that most of the AD core proteins directly interacted with each other, and further that their functions were focused on important functions in synapse such as spine formation, vesicle recycling, and energy metabolism. Particularly, it was revealed that the enhancement of the phosphorylations of the AD core proteins involved in nerve cell skeleton started from a non-symptomatic stage before amyloid β aggregation. Further, it was possible to categorize the changes in the AD core protein phosphorylations in a pre-onset stage of Alzheimer's disease into three patterns: one having a peak at an initial phase, one having a peak at a mid phase, and one having a peak at a late phase. In this manner, it was also revealed that the phosphorylation changed in each AD core protein in a time-specific manner.

Further, the analysis utilizing the protein-protein interaction database also enables the identifications of PKC, CaMK, CSK, and Lyn as kinases which controlled such time-specific changes in phosphorylations.

Meanwhile, it has been presumed that the transition from amyloid β aggregation (amyloid pathology) to tau phosphorylation and polymerization (tau pathology) by the aggregation plays an important role in the pathology of Alzheimer's disease. In this regard, the result of the mass spectrometry on the model mice also enabled the identification of b-RAF as a kinase which promoted the transition from amyloid pathology to tau pathology.

Furthermore, it was also verified that suppressing the expression of MARCKS or suppressing the kinase activity of PKC or CaMK enabled a recovery of Alzheimer's disease pathology (abnormal spine formation). These have led to the completion of the present invention.

Additionally, in order to provide target molecules useful in the diagnosis and treatment of frontotemporal lobar degeneration (FTLD), the present inventor first made efforts to prepare an animal which could be said as a true FTLD model in view of the current situation where the expressions of mutated mRNA and the like, which would cause the disease, had not been reproduced by the existing FTLD model animals as described above. To be more specific, efforts were made to prepare FTLD model mice by introducing a stop mutation, which was observed in FTLD patients, into the PGRN (progranulin) gene of mice. As a result, it was found out not only that the expressions of the mutated PGRN mRNA and a mutant protein encoded thereby were observed in the obtained PGRN-KI mice, but also that the introduction of the mutation enabled reproduction of both the pathological observations and the clinical symptoms of FTLD patients in the mice. Accordingly, it was revealed that the PGRN-KI mice were quite useful as FTLD model animals.

Next, using the PGRN-KI mice, efforts were made, as in the case of the above Alzheimer's disease analysis, to comprehensively analyze (phosphoproteome analysis) phosphorylation signal transductions in FTLD also to identify a phosphorylation signal transduction which played a central role in a pathology of the disease.

As a result, surprisingly, it was found that no protein had a change in phosphorylation in a TNF signal transduction pathway per se which had been heretofore suggested to be involved in the onset mechanism of FTLD. On the other hand, it was revealed that, in TNF-related signal transduction pathways such as a MAPK signal transduction pathway in the PGRN-KI mice, the phosphorylations of proteins belonging to such signal transduction pathways were remarkably changed. Particularly, a MAPK signal transduction pathway was apparently activated in the PGRN-KI mice from the pre-onset stage. During the period of symptom progression also, multiple proteins belonging to the signal transduction pathway were in high phosphorylation states all the time.

Hence, next, an analysis was performed for the therapeutic effect of targeting b-RAF, its phosphorylation substrate tau, and the like, which belonged to the MAPK signal transduction pathway, and which were revealed to be in high phosphorylation states in the PGRN-KI mice by the aforementioned analysis. To be more specific, first, analyzed was whether or not suppressing an abnormal activation in the MAPK signal transduction pathway by using a b-raf specific inhibitor or the like would recover the phenotype of the PGRN-KI mice.

The result revealed that administering the b-raf inhibitor alleviated the abnormal behavior observed in the PGRN-KI mice. Further, it was also revealed that administering the b-raf inhibitor or knocking down tau recovered the number of spines which was decreased in the PGRN-KI mice. These have led to the completion of the present invention.

To be more specific, the present invention relates to a diagnosis method, a diagnostic agent, a screening method for a candidate compound of the diagnostic agent, a therapeutic agent, and a screening method for a candidate compound of the therapeutic agent all of which are against Alzheimer's disease and target the above-described AD core proteins and kinases for phosphorylating the proteins. More specifically, the present invention provides the following.

<1> A method for diagnosing Alzheimer's disease, the method comprising:

(i) a step of detecting, in a test subject, a phosphorylation of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB;

(ii) a step of comparing the phosphorylation with a phosphorylation of a substrate protein in a normal subject; and (iii) a step of determining that the test subject is affected with Alzheimer's disease or has a risk of developing Alzheimer's disease if the phosphorylation of the substrate protein in the test subject is higher than the phosphorylation of the substrate protein in the normal subject as a result of the comparison.

<2> A method for diagnosing Alzheimer's disease, the method comprising:

(i) a step of detecting an activity or expression of a kinase protein in a test subject;

(ii) a step of comparing the activity or expression with an activity or expression of a kinase protein in a normal subject; and (iii) a step of determining that the test subject is affected with Alzheimer's disease or has a risk of developing Alzheimer's disease if the activity or expression of the kinase protein in the test subject is higher than the activity or expression of the kinase protein in the normal subject as a result of the comparison, wherein the kinase protein is at least one kinase protein selected from the group consisting of PKC, CaMK, CSK, Lyn, and b-RAF.

<3> An agent for diagnosing Alzheimer's disease, the agent comprising a compound having an activity of binding to a phosphorylation site of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB.

<4> An agent for diagnosing Alzheimer's disease, the agent comprising a compound having an activity of binding to at least one kinase protein selected from the group consisting of PKC, CaMK, CSK, Lyn, and b-RAF.

<5> A screening method for a candidate compound for diagnosing Alzheimer's disease, the method comprising the steps of:
bringing a test compound into contact with a phosphorylation site of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB; and
selecting the compound if the compound binds to the phosphorylation site.

<6> A screening method for a candidate compound for diagnosing Alzheimer's disease, the method comprising the steps of:
bringing a test compound into contact with at least one kinase protein selected from the group consisting of PKC, CaMK, CSK, Lyn, and b-RAF; and
selecting the compound if the compound binds to the kinase protein.

<7> An agent for treating Alzheimer's disease, the agent comprising a compound capable of suppressing a phosphorylation of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB.

<8> An agent for treating Alzheimer's disease, the agent comprising a compound capable of suppressing an activity or expression of at least one kinase protein selected from the group consisting of PKC, CaMK, CSK, Lyn, and b-RAF.

<9> The agent according to <8>, wherein the compound is capable of suppressing an activity or expression of b-RAF and is at least one compound selected from the group consisting of PLX-4720, sorafenib, GDC-0879, vemurafenib, dabrafenib, sorafenib tosylate, and LGX818.

<10> The agent according to <9>, wherein the compound is vemurafenib.

<11> An agent for treating Alzheimer's disease, the agent comprising a compound capable of suppressing a binding of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB to at least one kinase protein selected from the group consisting of PKC, CaMK, CSK, Lyn, and b-RAF.

<12> A screening method for a candidate compound for treating Alzheimer's disease, the method comprising:
(i) a step of applying a test compound to a system capable of detecting a phosphorylation of at least one substrate protein selected from the group consisting of MARCKS, Marcksl1, SRRM2, SPTA2, ADDS, NEUM, BASP1, SYT1, G3P, HS90A, CLH, NFH, NFL, GPRIN1, ACON, ATPA, and ATPB; and
(ii) a step of selecting the compound if the compound suppresses the phosphorylation of the substrate protein.

<13> A screening method for a candidate compound for treating Alzheimer's disease, the method comprising:
(i) a step of applying a test compound to a system capable of detecting an activity or expression of at least one kinase protein selected from the group consisting of PKC, CaMK, CSK, Lyn, and b-RAF; and
(ii) a step of selecting the compound if the compound suppresses the activity or expression of the protein.

<14> A screening method for a candidate compound for treating Alzheimer's disease, the method comprising the following steps (a) to (c):
(a) a step of bringing at least one kinase protein selected from the group consisting of PKC, CaMK, CSK, Lyn, and b-RAF into contact with at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB, in presence of a test compound;
(b) a step of detecting a binding between the kinase protein and the substrate protein; and
(c) a step of selecting the compound if the compound suppresses the binding.

In addition, the present invention relates to a therapeutic agent and a diagnostic agent which are against frontotemporal lobar degeneration and target b-RAF described above. More specifically, the present invention provides the following.

<15> An agent for treating frontotemporal lobar degeneration, the agent comprising a compound capable of suppressing an activity or expression of b-RAF.

<16> The agent according to <15>, wherein the compound is at least one compound selected from the group consisting of PLX-4720, sorafenib, GDC-0879, vemurafenib, dabrafenib, sorafenib tosylate, and LGX818.

<17> The agent according to <16>, wherein the compound is vemurafenib.

<18> An agent for diagnosing frontotemporal lobar degeneration, the agent comprising a compound having an activity of binding to b-RAF.

It should be noted that, in the present invention, "Alzheimer's disease" is a neurodegenerative disease also referred to as Alzheimer's dementia or AD, and includes "familial Alzheimer's disease" and "inherited Alzheimer's disease" attributable to gene mutation, and also "sporadic Alzheimer's disease" due to environmental factors such as lifestyle and stress. "Developing Alzheimer's disease" and related phrases mean an expression of symptoms such as memory disorder, higher brain function disorders (aphasia, apraxia, agnosia, constructional apraxia), and change in personality judged by clinical diagnosis, as well as appearance of atrophy in the brain judged by diagnostic imaging. "Affected with Alzheimer's disease" and related phrases mean to also include a state where the symptoms are not expressed, but a pathological change peculiar to Alzheimer's disease (for example, amyloid β aggregation) occurs.

In addition, in the present invention, "frontotemporal lobar degeneration" is a non-Alzheimer's disease type neurodegenerative disease also referred to as FTLD, by which atrophy occurs in the frontal lobe and temporal lobe at the early stage, and atrophy occurs throughout the brain at the late stage. To be more specific, frontotemporal lobar degeneration includes three diseases classified according to clinical characteristics: frontotemporal dementia (FTD), progressive nonfluent aphasia (PNFA), and semantic dementia (SD). Moreover, frontotemporal lobar degeneration includes four diseases pathologically classified into FTLD-Tau, FTLD-TDP, FTLD-UPS, and FTLD-FUS according to the type of proteins accumulated as abnormal proteins in cells.

Further, "FTLD-Tau" is classified into "3R Tau" type, "4R Tau" type, and "3/4R Tau" type according to the number of microtubule-binding regions repeated in tau proteins predominantly accumulated in cells. Moreover, the "3R Tau" type includes FTLD with Pick bodies (Pick's disease), FTLD with MAPT (microtubule-associated protein tau) gene mutation (FTLD-17), and the like. The "4R Tau" type includes corticobasal degeneration, progressive supranuclear palsy, multiple system tauopathy with dementia, argyrophilic grain dementia (argyrophilic grain disease), FTLD with MAPT gene mutation (FTLD-17), and the like. The "3/4R Tau" type includes dementia with neurofibrillary tangles, FTLD with MAPT gene mutation (FTLD-17), and the like. On the other hand, a FTLD group having tau-negative, ubiquitin-positive inclusions is called "FTLD-U", and includes FTLD-TDP, FTLD-UPS and FTLD-FUS described above.

Among FTLD-U, "FTLD-TDP" means a TDP-43-positive disease. This disease includes FTLD with PGRN (progranulin gene) mutation, sporadic FTLD-TDP/FTLD-U, FTLD with TARDBP (TDP-43 gene) mutation, FTLD with VCP (valosi-containing protein gene) mutation, FTLD linked to chromosome 9, and the like. Moreover, "FTLD-FUS" among FTLD-U means TDP-43-negative, FUS (fused in sarcoma)-positive disease. This disease includes neuronal intermediate filament inclusion disease, non-typical FTLD-U, basophilic inclusion body disease, FTLD with FUS mutation, and the like.

Further, "FTLD-UPS" is one of TDP-43-negative FTLD-U, This disease includes FTLD with CHMP2B (charged multivesicular body protein 2B gene) mutation, and the like.

"Developing frontotemporal lobar degeneration" and related phrases mean an expression of symptoms such as memory disorder, higher brain function disorders (aphasia, apraxia, agnosia, constructional apraxia), and change in personality judged by clinical diagnosis, as well as appearance of atrophy in the brain judged by diagnostic imaging. "Affected with frontotemporal lobar degeneration" and related phrases mean to also include a state where the symptoms are not expressed, but a pathological change peculiar to frontotemporal lobar degeneration (for example, accumulation of the abnormal proteins in cells) occurs.

The "test subject" is a subject of the diagnosis method of the present invention, and includes not only bodies of animals including human, but also body fluids, tissues, cells, and the like (for example, cerebrospinal fluid, cranial nerve tissues (particularly neurological bioptic tissues), blood, blood plasma, serous fluid, lymph, urine, saliva) isolated from the bodies.

The term "normal" in the normal subject means a state where the subject is not affected with at least the disease (Alzheimer's disease or frontotemporal lobar degeneration) to be targeted by the diagnosis method of the present invention. Additionally, in the diagnosis method of the present invention, a normal subject used as a comparison target of a test subject is preferably the same gender as the test subject and similar in age.

Furthermore, in the present invention, "MARCKS" is a protein also referred to as myristoylated alanine-rich C-kinase substrate. A typical human-derived example thereof includes a protein specified under RefSeq ID: NP_002347. Moreover, a typical example of a human-derived nucleic acid encoding MARCKS includes a nucleic acid containing a coding region (CDS) represented by RefSeq ID: NM_002358.

"Marcksl1" is a protein also referred to as MARCKS-like protein 1. A typical human-derived example thereof includes a protein specified under RefSeq ID: NP_075385. Moreover, a typical example of a human-derived nucleic acid encoding MARCKS includes a nucleic acid containing a CDS represented by RefSeq ID: NM_023009.

"SRRM2" is a protein also referred to as SRm300/serine-arginine repetitive matrix protein 2. A typical human-derived example thereof includes a protein specified under RefSeq ID: NP_057417. Moreover, atypical example of a human-derived nucleic acid encoding SRRM2 includes a nucleic acid containing a CDS represented by RefSeq ID: NM_016333.

"SPTA2" is a protein also referred to as α-II spectrin. Typical human-derived examples thereof include a protein specified under RefSeq NP_001123910, a protein specified under RefSeq NP_001182461, and a protein specified under RefSeq NP_003118. Moreover, typical examples of a human-derived nucleic ac id encoding SPTA2 include a nucleic acid containing a CDS represented by RefSeq NM_001130438, a nucleic acid containing a CDS represented by RefSeq NM_001195532, and a nucleic acid containing a CDS represented by RefSeq NM_003127.

"ADDB" is a protein also referred to as β adducin. Typical human-derived examples thereof include a protein specified under RefSeq NP_001171983, a protein specified under RefSeq NP_001171984, a protein specified under RefSeq NP_001608, a protein specified under RefSeq NP_059516, and a protein specified under RefSeq NP_059522. Moreover, typical examples of a human-derived nucleic acid encoding ADDB include a nucleic acid containing a CDS represented by RefSeq NM_001185054, a nucleic acid containing a CDS represented by RefSeq NM_001185055, a nucleic acid containing a CDS represented by RefSeq NM_001617, a nucleic acid containing a CDS represented by RefSeq NM_017482, and a nucleic acid containing a CDS represented by RefSeq NM_017488.

"NEUM" is a protein also referred to as neuromodulin or GAP43. Typical human-derived examples thereof include a protein specified under RefSeq NP_00112353 and a protein specified under RefSeq NP_002036. Moreover, typical examples of a human-derived nucleic acid encoding NEUM include a nucleic acid containing a CDS represented by RefSeq NM_001130064 and a nucleic acid containing a CDS represented by RefSeq NM_002045.

"BASP1" is a protein also referred to as NAP-22 or CAP23. Typical human-derived examples thereof include a protein specified under RefSeq NP_001258535 and a protein specified under RefSeq NP_006308. Moreover, typical examples of a human-derived nucleic acid encoding BASP1 include a nucleic acid containing a CDS represented by RefSeq NM_001271606 and a nucleic acid containing a CDS represented by RefSeq NM_006317.

"SYT1" is a protein also referred to as synaptotagmin 1. Typical human-derived examples thereof include a protein specified under RefSeq NP_00112927, a protein specified under RefSeq NP_001129278, and a protein specified under RefSeq NP_005630. Moreover, typical examples of a human-derived nucleic acid encoding SYT1 include a nucleic acid containing a CDS represented by RefSeq NM_001135805, a nucleic acid containing a CDS represented by RefSeq NM_001135806, and a nucleic acid containing a CDS represented by RefSeq NM_005639.

"G3P" is a protein also referred to as glyceraldehyde-3-phosphate dehydrogenase. Typical human-derived examples thereof include a protein specified under RefSeq NP_001243728 and a protein specified under RefSeq NP_002037. Moreover, typical examples of a human-derived nucleic acid encoding G3P include a nucleic acid containing a CDS represented by RefSeq NM_001256799 and a nucleic acid containing a CDS represented by RefSeq NM_002046.

"HS90A" is a protein also referred to as HSP90, HSP90a, or HSP86. Typical human-derived examples thereof include a protein specified under RefSeq NP_001017963 and a protein specified under RefSeq NP_005339. Moreover, typical examples of a human-derived nucleic acid encoding HS90A include a nucleic acid containing a CDS represented by RefSeq NM_001017963 and a nucleic acid containing a CDS represented by RefSeq NM_005348.

"CLH" is a protein also referred to as CLH1 or clathrin heavy chain 1. A typical human-derived example thereof includes a protein specified under NP_004850. Moreover, a typical example of a human-derived nucleic acid encoding CLH includes a nucleic acid containing a CDS represented by NM_004859.

"NFH" is a protein also referred to as neurofilament heavy polypeptide. A typical human-derived example thereof includes a protein specified under RefSeq NP_066554. Moreover, atypical example of a human-derived nucleic acid encoding NFH includes a nucleic acid containing a CDS represented by RefSeq NM_021076.

"NFL" is a protein also referred to as neurofilament light polypeptide. A typical human-derived example thereof includes a protein specified under RefSeq NP_00614. Moreover, a typical example of a human-derived nucleic acid encoding NFL includes a nucleic acid containing a CDS represented by RefSeq NM_006158.

"GPRIN1" is a protein also referred to as G protein regulated inducer 1. Typical human-derived examples thereof include a protein specified under RefSeq NP_443131.2 and a protein specified under RefSeq XP_005265863. Moreover, typical examples of a human-derived nucleic acid encoding GPRIN1 include a nucleic acid containing a CDS represented by RefSeq NM_052899 and a nucleic acid containing a CDS represented by RefSeq XM_005265806.

"ACON" is a protein also referred to as aconitate hydratase. A typical human-derived example thereof includes a protein specified under RefSeq NP_001089. Moreover, atypical example of a human-derived nucleic acid encoding ACON includes a nucleic acid containing a CDS represented by RefSeq NM_001098.

"ATPA" is a protein also referred to as ATP synthase subunit α, ATP5A1, ATP5A, ATP5AL2, or ATPM. Typical human-derived examples thereof include a protein specified under RefSeq NP_001001935, a protein specified under RefSeq NP_001001937, a protein specified under RefSeq NP_001244263, a protein specified under RefSeq NP_001244264, and a protein specified under RefSeq NP_004037. Moreover, typical examples of a human-derived nucleic acid encoding ATPA include a nucleic acid containing a CDS represented by RefSeq NM_001001935, a nucleic acid containing a CDS represented by RefSeq NM_001001937, a nucleic acid containing a CDS represented by RefSeq NM_001257334, a nucleic acid containing a CDS represented by RefSeq NM_001257335, and a nucleic acid containing a CDS represented by RefSeq NM_004046.

"ATPB" is a protein also referred to as ATP synthase subunit β, ATPMB, or ATPSB. A typical human-derived example thereof includes a protein specified under RefSeq NP_001677. Moreover, a typical example of a human-derived nucleic acid encoding ATPB includes a nucleic acid containing a CDS represented by RefSeq NM_001686. Further, in the present invention, "PKC" is a protein also referred to as protein kinase C. Examples thereof include PKCβ, PKCα, PKCλ/ι (lambda/iota), PKCσ (delta), and PKCζ (zeta).

Typical examples of human-derived "PKCβ" include a protein specified under RefSeq NP_002729 and a protein specified under RefSeq NP_997700. Moreover, a typical example of a human-derived nucleic acid encoding PKCβ includes a nucleic acid containing a CDS represented by RefSeq NM_002738 and a nucleic acid containing a CDS represented by RefSeq NM_212535.

A typical example of human-derived "PKCα" includes a protein specified under RefSeq NP_002728. Moreover, a typical example of a human-derived nucleic acid encoding PKCα includes a nucleic acid containing a CDS represented by RefSeq NM_002737.

Atypical example of human-derived "PKCλ/ι" includes a protein specified under RefSeq NP_002731. Moreover, a typical example of a human-derived nucleic acid encoding PKCλ/ι includes a nucleic acid containing a CDS represented by RefSeq NM_002740.

Typical examples of human-derived "PKCσ" include a protein specified under RefSeq NP_006245 and a protein specified under RefSeq NP_997704. Moreover, typical examples of a human-derived nucleic acid encoding PKCσ include a nucleic acid containing a CDS represented by RefSeq NM_006254 and a nucleic acid containing a CDS represented by RefSeq NM_212539.

Typical examples of human-derived "PKCζ" include a protein specified under RefSeq NP_001028753, a protein specified under RefSeq NP_001028754, a protein specified under RefSeq NP_001229803, and a protein specified under RefSeq NP_002735. Moreover, typical examples of a human-derived nucleic acid encoding PKC include a nucleic acid containing a CDS represented by RefSeq NM_001033581, a nucleic acid containing a CDS represented by RefSeq NM_001033582, a nucleic acid containing a CDS represented by RefSeq NM_001242874, and a nucleic acid containing a CDS represented by RefSeq NM_002744.

"CaMK" is a protein also referred to as calmodulin kinase or calmodulin-dependent protein kinase. Examples thereof include CaMKI, CaMKIIβ, CaMKIV, CaMKIIσ (delta), and CaMKIIα.

A typical example of human-derived "CaMKI" includes a protein specified under RefSeq NP_003647. Moreover, a typical example of a human-derived nucleic acid encoding CaMKI includes a nucleic acid containing a CDS represented by RefSeq NM_003656.

Typical human-derived examples of "CaMKIIβ" include a protein specified under RefSeq NP_001211, a protein specified under RefSeq NP_742075, a protein specified under RefSeq NP_742076, a protein specified under RefSeq NP_742077, a protein specified under RefSeq NP_742078, a protein specified under RefSeq NP_742079, a protein specified under RefSeq NP_742080, a protein specified under RefSeq NP_742081, and a protein specified under RefSeq XP_005249918. Moreover, typical examples of a human-derived nucleic acid encoding CaMKIIβ include a nucleic acid containing a CDS represented by RefSeq NM_001220, a nucleic acid containing a CDS represented by RefSeq NM_172078, a nucleic acid containing a CDS represented by RefSeq NM_172079, a nucleic acid containing a CDS represented by RefSeq NM_172080, a nucleic acid containing a CDS represented by RefSeq NM_172081, a nucleic acid containing a CDS represented by RefSeq NM_172082, a nucleic acid containing a CDS represented by RefSeq NM_172083, a nucleic acid containing a CDS represented by RefSeq NM_172084, and a nucleic acid containing a CDS represented by RefSeq XM_005249861.

A typical example of human-derived "CaMKIV" includes a protein specified under RefSeq NP_001735. Moreover, a typical example of a human-derived nucleic acid encoding CaMKIV includes a nucleic acid containing a CDS represented by RefSeq NM_001744.

Typical examples of human-derived "CaMKIIσ" include a protein specified under RefSeq NP_001212, a protein specified under RefSeq NP_742112, a protein specified under RefSeq NP_742113, a protein specified under RefSeq NP_742125, a protein specified under RefSeq NP_742126, a protein specified under RefSeq NP_742127, and a protein specified under RefSeq XP_005263312. Moreover, typical examples of a human-derived nucleic acid encoding CaMKIIσ include a nucleic acid containing a CDS represented by RefSeq NM_001221, a nucleic acid containing a CDS represented by RefSeq NM_172114, a nucleic acid containing a CDS represented by RefSeq NM_172115, a nucleic acid containing a CDS represented by RefSeq NM_172127, a nucleic acid containing a CDS represented by RefSeq NM_172128, a nucleic acid containing a CDS represented by RefSeq NM_172129, and a nucleic acid containing a CDS represented by RefSeq XM_005263255.

A typical example of human-derived "CaMKIIα" includes a protein specified under RefSeq NP_741960. Moreover, a typical example of a human-derived nucleic acid encoding CaMKIIα includes a nucleic acid containing a CDS represented by RefSeq NM_171825. "CSK" is a protein also referred to as casein kinase. Examples thereof include CSKIIα and CSKII subunit α.

Typical examples of human-derived "CSKIIα" include a protein specified under RefSeq NP_001886, a protein specified under RefSeq NP_808227, and a protein specified under RefSeq NP_808228. Moreover, typical examples of a human-derived nucleic acid encoding CSKIIα include a nucleic acid containing a CDS represented by RefSeq NM_001895, a nucleic acid containing a CDS represented by RefSeq NM_177559, and a nucleic acid containing a CDS represented by RefSeq NM_177560.

A typical example of human-derived "CSKII subunit a" includes a protein specified under RefSeq NP_001887. Moreover, a typical example of a human-derived nucleic acid encoding CSKII subunit α includes a nucleic acid containing a CDS represented by RefSeq NM_001896.

"Lyn" is a protein also referred to as Lyn tyrosine kinase. Typical human-derived examples thereof include a protein specified under RefSeq NP_001104567, a protein specified under RefSeq NP_002341, a protein specified under RefSeq XP_005251289, and a protein specified under RefSeq XP_005251290. Moreover, typical examples of a human-derived nucleic acid encoding Lyn include a nucleic acid containing a CDS represented by RefSeq NM_001111097, a nucleic acid containing a CDS represented by RefSeq NM_002350, a nucleic acid containing a CDS represented by RefSeq XM_005251232, and a nucleic acid containing a CDS represented by RefSeq XM_005251233.

"b-RAF" is a protein also referred to as b-RAF serine/threonine kinase. A typical human-derived example thereof includes a protein specified under RefSeq NP_004324.

Moreover, a typical example of a human-derived nucleic acid encoding b-RAF includes a nucleic acid containing a CDS represented by RefSeq NM_004333.4.

Advantageous Effects of Invention

The present invention makes it possible to diagnose before the onset of Alzheimer's disease, and further to provide agents and methods effective for treating the disease. Moreover, the present invention makes it possible to diagnose frontotemporal lobar degeneration before the onset, and further to provide agents and methods effective for treating the disease.

BRIEF DESCRIPTION OF DRAWINGS

The patent or application file of this patent contains at least one drawing executed in color. Copies of this patent with color drawing(s) will be provided by the Patent and Trademark Office upon request and payment of the necessary fee.

FIG. 34 shows the comparison results between 14 proteins selected from the AD model mice by the hypothesis free approach and phosphoproteins which changed in the Tau model mice. As a result, it was revealed that 10 phosphoproteins (ADDB, NFH, NFL, SPTA2, BASP1, CLH, MARCS, NEUM, SRRM2, and Marcksl1) were commonly changed between the AD model mice and the Tau model mice.

DESCRIPTION OF EMBODIMENTS

<Method 1 for Diagnosing Alzheimer's Disease>

Figure 1:
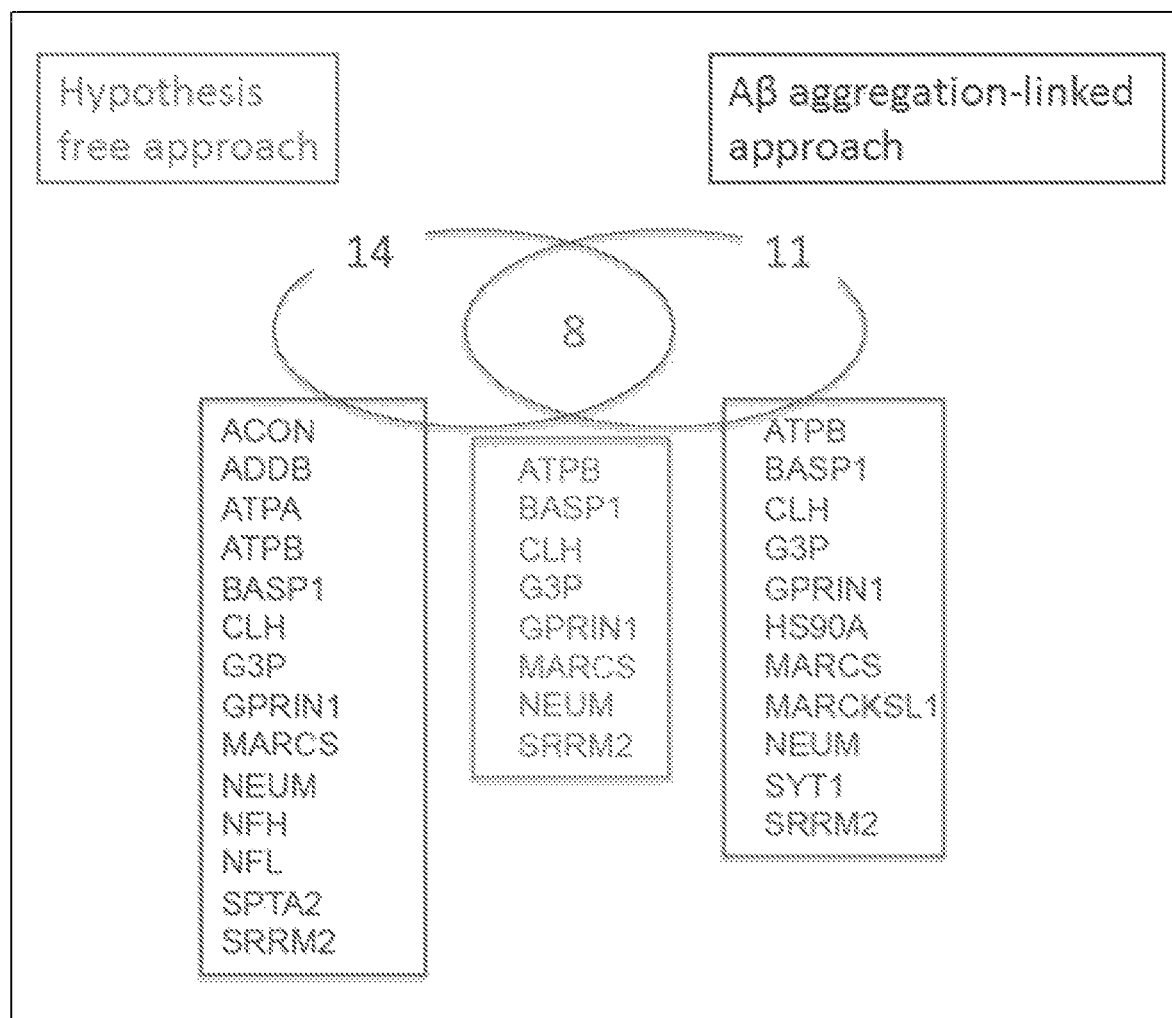
FIG. 1 is a diagram showing phosphoproteins which were identified by two different approaches (hypothesis free approach and Aβ aggregation-linked approach) and whose expression amounts were enhanced commonly in multiple Alzheimer's disease (AD) model mice. In the figure, "MARCS" and "MARCKSL1" respectively represent MARCKS and Marcksl1.

As will be described later in Examples, it has been revealed that phosphorylations of MARCKS Marcksl1, SRRM2, SPTA2, ADDB, NEUM, BASP1, SYT1, G3P, HS90A, CLH, NFH, NFL, GPRIN1, ACON, ATPA, and ATPB are commonly enhanced in multiple Alzheimer's disease model mice before the onset of the disease. Thus, the present invention provides a method for diagnosing Alzheimer's disease based on the phosphorylation of these proteins, the method comprising the following steps (i) to (iii):

(i) a step of detecting, in a test subject, a phosphorylation of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB;

(ii) a step of comparing the phosphorylation with a phosphorylation of a substrate protein in a normal subject; and (iii) a step of determining that the test subject is affected with Alzheimer's disease or has a risk of developing Alzheimer's disease if the phosphorylation of the substrate protein in the test subject is higher than the phosphorylation of the substrate protein in the normal subject as a result of the comparison.

In this diagnosis method, the substrate proteins such as MARCKS are not limited respectively to the proteins having the amino acid sequences listed as the typical examples described above, and naturally-occurring mutants thereof can also be targeted. Moreover, in a case where multiple sites (amino acid residues) are phosphorylated in one substrate protein, the phosphorylation of at least one site of the protein should be detected. Nevertheless, from the viewpoint of further increasing the diagnosis precision, it is preferable to detect all the phosphorylation sites of the protein.

In the case of human, examples of the phosphorylation site in MARCKS to be detected by the present invention include serine at position 26, serine at position 27, serine at position 29, serine at position 118, serine at position 128, serine at position 131, serine at position 132, serine at position 134, serine at position 135, serine at position 145, serine at position 147, threonine at position 150, serine at position 170, and serine at position 322. Examples thereof in Marcksl1 include serine at position 22, threonine at position 85, serine at position 104, threonine at position 148, serine at position 151, serine at position 180, and serine at position 184. Examples thereof in SRRM2 include serine at position 1102, serine at position 1320, serine at position 1348, serine at position 1383, serine at position 1403, serine at position 1404, serine at position 2398, serine at position 2132, serine at position 2449, serine at position 2581, threonine at position 1492, and threonine at position 2397. Examples thereof in SPTA2 include serine at position 1031 and serine at position 1217. Examples thereof in ADDB include serine at position 60, serine at position 62, serine at position 532, serine at position 592, serine at position 600, serine at position 617, serine at position 693, and serine at position 701. Examples thereof in NEUM include serine at position 151, threonine at position 181, and serine at position 203. Examples thereof in BASP1 include threonine at position 31, threonine at position 36, serine at position 132, serine at position 195, and serine at position 219. Examples thereof in SYT1 include threonine at position 126 and threonine at position 129. Examples thereof in G3P include threonine at position 184 and threonine at position 211. Examples thereof in HS90A include serine at position 231 and serine at position 263. Examples thereof in NFH include serine at position 503, serine at position 540, serine at position 660, serine at position 730, serine at position 769, serine at position 801, and serine at position 828. An example thereof in NFL includes serine at position 472. Examples thereof in GPRIN1 include serine at position 776, serine at position 799, serine at position 850, serine at position 853, and threonine at position 877.

Note that these phosphorylation sites are sites in Alzheimer's disease model mice where phosphorylation levels were changed and identified in Example 5 to be described later, and converted to corresponding human sites (regarding the correspondence between human and mouse at each phosphorylation site, see PhosphoSite Plus (www.phosphosite.org/homeAction.do)). Additionally, in the present invention, the term "phosphorylation site" means a site having at least 3 amino acids including one amino acid before and one amino acid after a phosphorylated amino acid in a phosphorylated protein such as the substrate protein.

In the diagnosis method, in a case where a test subject whose substrate protein phosphorylation is to be detected is a specimen (such as body fluid, tissue, cell) isolated from a body of an animal including human, that is, where the diagnosis method is an in vitro method, an example of the detection method in the step (i) includes a mass spectrometry method as will be described later in Examples, that is, a method in which phosphopolypeptides are extracted from the specimen, labeled, and analyzed by 2D LC MS/MS. Such a detection by a mass spectrometry method is preferable from the viewpoint that multiple phosphorylations of multiple substrate proteins can be comprehensively detected, consequently further increasing the diagnosis precision.

Moreover, the in vitro method includes a detection method using an antibody capable of specifically binding to a phosphorylation site of a substrate protein, for example, immunohistochemical staining, immunoelectron microscopy, and immunoassays (such as enzyme immunoassay (ELISA, EIA), fluorescent immunoassay, radioimmunoassay (RIA), immunochromatography, and western blot method). Further, the example also includes a method utilizing a detector (for example, BIAcore (manufactured by GE Healthcare)) based on the surface plasmon resonance phenomenon using a thin metal film on which a compound capable of specifically binding to a phosphorylation site of a substrate protein is immobilized. Regarding the antibody and the compound, see the description of <Diagnostic Agent Against Alzheimer's Disease> to be Described Later.

Meanwhile, in the diagnosis method, in a case where a test subject whose substrate protein phosphorylation is to be detected is a body of an animal including human, that is, where the diagnosis method is an in vivo method, examples of the detection method in the step (i) include bioimaging techniques (computerized axial tomographies (CAT, CT), magnetic resonance imaging (MRI), positron emission tomography (PET), single-photon emission computed tomography (SPECT)). More concretely, the detection can be performed with reference to the techniques described in International Application Japanese-Phase Publication Nos. 2004-513123, 2004-530408, and 2002-514610, Japanese Unexamined Patent Application Publication No. 2011-95273, International Application Japanese-Phase Publication Nos. 2001-527509, Hei 9-501419, Hei 9-505799, and Hei 8-509226. Nevertheless, the embodiment of the diagnosis method of the present invention is not limited thereto.

In the bioimaging techniques, a compound capable of specifically binding to a phosphorylation site of a substrate protein is introduced into the body of a test subject. The introduction method is not particularly limited, and examples thereof include intravenous administration, intraarterial administration, intraperitoneal administration, subcutaneous administration, intradermal administration, tracheobronchial administration, rectal administration and intramuscular administration, administration by transfusion, and direct administration into a target site (such as brain). The direct administration into a target site can be achieved by employing, for example, cannula (catheter), surgical incision, or the like. Regarding the compound, see the description of <Diagnostic Agent against Alzheimer's Disease> to be described later.

In addition, as will be described later in Examples, the substrate proteins to be detected in the method for diagnosing Alzheimer's disease are classified into three according to the pattern of the chronological change in phosphorylation. To be more specific, examples of the substrate protein whose phosphorylation is enhanced the most at an initial phase of a pre-onset stage of Alzheimer's disease include MARCKS, Marcksl1, and SRRM2; examples of the substrate protein whose phosphorylation is enhanced the most at a mid phase of the pre-onset stage of Alzheimer's disease include SPTA2, ADDB, NEUM, BASP1, SYT1, G3P, and HS90A; and examples of the substrate protein whose phosphorylation is enhanced the most at a late phase of the pre-onset stage of Alzheimer's disease include CLH, NFH, NFL, and GPRIN1. Thus, in the step (iii), if the phosphorylations of at least two substrate proteins among MARCKS, Marcksl1, and SRRM2 (more preferably the phosphorylations of all the three substrate proteins) are higher than those in a normal subject, the test subject can be determined to be at the initial phase before the onset of Alzheimer's disease. Moreover, if the phosphorylations of at least two substrate proteins among SPTA2, ADDB, NEUM, BASP1, SYT1, G3P, and HS90A (more preferably the phosphorylations of three substrate proteins, the phosphorylations of four substrate proteins, the phosphorylations of five substrate proteins, furthermore preferably the phosphorylations of six substrate proteins, and particularly preferably the phosphorylations of all the seven substrate proteins) are higher than those in a normal subject, the test subject can be determined to be at the mid phase before the onset of Alzheimer's disease. Further, if the phosphorylations of at least two substrate proteins among CLH, NFH, NFL, and GPRIN1 (more preferably the phosphorylations of three substrate proteins, furthermore preferably the phosphorylations of all the four substrate proteins) are higher than those in a normal subject, the test subject can be determined to be at the late phase before the onset of Alzheimer's disease.

<Method 2 for Diagnosing Alzheimer's Disease>

In addition, as will be described later in Examples, it has also been revealed that kinase proteins which phosphorylate the substrate proteins such as MARCKS are activated in the Alzheimer's disease model mice before the onset of the disease. Thus, the present invention also provides, as a second embodiment of the method for diagnosing Alzheimer's disease, a method comprising the following the steps (i) to (iii):

(i) a step of detecting an activity or expression of a kinase protein in a test subject;

(ii) a step of comparing the activity or expression with an activity or expression of a kinase protein in a normal subject; and (iii) a step of determining that the test subject is affected with Alzheimer's disease or has a risk of developing Alzheimer's disease if the activity or expression of the kinase protein in the test subject is higher than the activity or expression of the kinase protein in the normal subject as a result of the comparison, wherein the kinase protein is at least one kinase protein selected from the group consisting of PKC, CaMK, CSK, Lyn, and b-RAF.

In this diagnosis method, the kinase proteins such as PKC are not limited respectively to the proteins having the amino acid sequences listed as the typical examples described above, and naturally-occurring mutants thereof can also be targeted. Moreover, the "activity" of the kinase proteins to be detected means an activity (kinase activity) of directly or indirectly phosphorylating the substrate protein. Further, since a kinase activity correlates with an amount of a kinase protein expressed, particularly an amount of an activated kinase protein expressed, the amount of a kinase protein expressed, preferably the amount of an activated kinase protein expressed, can also be the target of the detection by the diagnosis method in place of the kinase activity.

In the present invention, the "activated kinase protein" means a kinase protein in a state where the kinase protein is capable of phosphorylating the substrate protein. An example thereof includes a phosphorylated kinase protein. More concretely, the examples of the activated kinase protein include PKCβ having threonine at position 642 phosphorylated, PKCα having threonine at position 638 phosphorylated, PKCλ/ι having threonine at position 403 phosphorylated, PKCζ having serine at position 643 phosphorylated, PKC having threonine at position 410 phosphorylated, PKC having tyrosine at position 417 phosphorylated, CaMKI having serine at position 177 phosphorylated, CaMKIIβ having threonine at position 287 phosphorylated, CaMKIV having threonine at position 200 phosphorylated, CaMKIIσ having threonine at position 287 phosphorylated, CaMKIIα having threonine at position 286 phosphorylated, CSKIIα having threonine at position 360 phosphorylated, CSKIIα having serine at position 362 phosphorylated, Lyn having tyrosine at position 397 phosphorylated, b-RAF having serine at position 365 phosphorylated, b-RAF having serine at position 446 phosphorylated, b-RAF having serine at position 579 phosphorylated, b-RAF having threonine at position 599 phosphorylated, b-RAF having serine at position 602 phosphorylated, b-RAF having serine at position 729 phosphorylated, and b-RAF having serine at position 732 phosphorylated.

In the case where the diagnosis method is an in vitro method, the detection of the activity can be performed, for example, by adding a substrate and a radiolabeled phosphate to the specimen or a protein liquid extract thereof, and detecting the incorporation of the phosphate into the substrate. The incorporation of the phosphate into the substrate can be detected with a scintillation counter, by autoradiography, or other means. Alternatively, without using a radioactive label, the activity can also be detected by treating the substrate with the specimen or a protein liquid extract thereof, and detecting an increase in the molecular weight of the substrate after the treatment. The detection of an increase in the molecular weight can be performed, for example, by detecting a change in mobility of the substrate in polyacrylamide gel electrophoresis. Further, the polyacrylamide gel after the electrophoresis may be transferred to a membrane such as PVDF for the detection by a western blot method using an antibody capable of specifically binding to a phosphorylation site of the substrate. Note that examples of the substrate include known substrate proteins of the targeted kinase proteins, and partial peptides thereof containing a site to be phosphorylated (phosphorylated site).

Examples of the known substrate proteins of PKC include MARCKS, Marcksl1, SPTA2, ADDB, NEUM, BASP1, SYT1, G3P, and HSP90A. More concretely, examples of the substrate proteins of PKCβ include SPTA2, MARCKS, and NEUM; examples of the substrate protein of PKCα include MARCKS and HSP90A; an example of the substrate protein of PKCζ includes Marcksl1; examples of the substrate protein of PKCλ/ι include G3P and HSP90A; and examples of the substrate protein of PKCδ include ADDB, NEUM, and HSP90A.

Examples of the known substrate proteins of CaMK include SPTA2 and G3P. More concretely, an example of the substrate protein of CaMKI includes G3P; an example of the substrate protein of CaMKIIβ includes G3P; an example of the substrate protein of CaMKIV includes G3P; and an example of the substrate protein of CaMKIIδ includes SPTA2.

Examples of the known substrate proteins of CSK include NEUM, SYT1, and HSP90A. More concretely, an example of the substrate protein of CSKII subunit α includes HSP90A; and examples of the substrate protein of CSKIIα include NEUM and HSP90A.

An example of the known substrate protein of Lyn includes G3P. Moreover, examples of the substrate protein of b-RAF include MEK1, ERK1, and tau.

Moreover, in the in vitro method, examples of the method for detecting the expression amount include, as in the case of the detection of substrate protein phosphorylation described above, a mass spectrometry method, a detection method using an antibody capable of specifically binding to a kinase protein (preferably, activated kinase protein), and a method utilizing a detector based on the surface plasmon resonance phenomenon using a thin metal film on which a compound capable of specifically binding to a kinase protein (preferably, activated kinase protein) is immobilized. Regarding the antibody and the compound, see the description of <Diagnostic Agent against Alzheimer's Disease> to be described later.

In the case where the diagnosis method is an in vivo method, the detection of the activity can be performed by detecting the substrate protein phosphorylation attributable to the activity. To be more specific, bioimaging techniques aiming at the detection of substrate protein phosphorylation described above can be suitably used.

Moreover, in the case where the diagnosis method is an in vivo method, the detection of the expression amount can be performed as in the case of the detection of substrate protein phosphorylation described above, for example, by utilizing bioimaging techniques using a compound capable of specifically binding to a kinase protein (preferably, activated kinase protein). Regarding the compound, see the description of <Diagnostic Agent against Alzheimer's Disease> to be described later.

Hereinabove, preferred embodiments of the diagnosis method of the present invention have been described. In addition, such a diagnosis is normally conducted by a doctor (including one instructed by a doctor). The data on the phosphorylation of the substrate protein or the activity or expression of the kinase protein in the test subject obtained by the diagnosis method of the present invention is useful in the diagnosis by a doctor. Thus, the method of the present invention can also be described as a method for collecting and presenting such data useful in a diagnosis by a doctor.

Moreover, the present invention makes it possible to determine that one is affected with Alzheimer's disease or has a risk of developing Alzheimer's disease. In this manner, enabling judgment of Alzheimer's disease affection or the like at an early stage leads to an expectation that treatment methods for suppressing a pathology of Alzheimer's disease (immunotherapy, a method for administering an agent for suppressing a pathology of Alzheimer's disease) will be effective.

Thus, the present invention also makes it possible to provide a method for treating Alzheimer's disease, the method comprising: a step of administering an agent for suppressing a pathology of Alzheimer's disease to a test subject determined to be affected with Alzheimer's disease or have a risk of developing Alzheimer's disease by the method for diagnosing Alzheimer's disease of the present invention, and/or a step of conducting an immunotherapy for the test subject.

Examples of the immunotherapy include active immunotherapy (vaccine therapy) using a partial peptide of amyloid to suppress amyloid β aggregation, and passive immunotherapy in which an antibody against amyloid β is administered.

Additionally, examples of the agent administered to suppress a pathology of Alzheimer's disease include agents for suppressing amyloid β production (such as γ-secretase modulators (GSM), γ-secretase modulator inhibitors (GSI), nonsteroidal anti-inflammatory drugs), agents for suppressing amyloid β aggregation (such as curcumin, polysulfuric acid compound, clioquinol), agents for suppressing tau aggregation (such as aminothienopyridazine, cyanine dye, methylene blue), neuroprotective drugs (such as dimebon), cholinesterase inhibitors (such as donepezil), acetylcholinesterase inhibitors (such as galantamine), and NMDA glutamate receptor inhibitors (such as memantine).

Further, as will be described later, it is also possible to suitably use, as the agent for suppressing a pathology of Alzheimer's disease, an agent for treating Alzheimer's disease, the agent comprising any one of: a compound capable of suppressing a phosphorylation of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB; a compound capable of suppressing an activity or expression of at least one kinase protein selected from the group consisting of PKC, CaMK, CSK, Lyn, and b-RAF; a compound capable of activating Lyn; and a compound capable of suppressing a binding of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB to at least one kinase protein selected from the group consisting of PKC, CaMK, CSK, Lyn, and b-RAF.

<Diagnostic Agent Against Alzheimer's Disease>

As described above, it has been revealed that the phosphorylations of MARCKS and the like are commonly enhanced in the multiple Alzheimer's disease model mice before the onset of the disease. Thus, the present invention provides an agent for diagnosing Alzheimer's disease, the agent comprising a compound having an activity of binding to a phosphorylation site of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB (hereinafter, the agent for diagnosing Alzheimer's disease may also be referred to as "Alzheimer's disease diagnostic agent").

As described above, it has been revealed that the kinase proteins which phosphorylate the substrate proteins such as MARCKS are also activated in the Alzheimer's disease model mice before the onset of the disease. Thus, the present invention provides an agent for diagnosing Alzheimer's disease, the agent comprising a compound having an activity of binding to at least one kinase protein selected from the group consisting of PKC, CaMK, CSK, Lyn, and b-RAF. Further, an example of a preferred embodiment of the agent includes an agent for diagnosing Alzheimer's disease, the agent comprising a compound having an activity of binding to at least one activated kinase protein selected from the group consisting of PKC, CaMK, CSK, Lyn, and b-RAF.

As in the diagnosis method described above, the substrate proteins and the kinase proteins targeted by the diagnostic agents of the present invention are not limited respectively to the proteins having the amino acid sequences listed as the typical examples described above, and naturally-occurring mutants thereof can also be targeted.

The "compound having an activity of binding to the phosphorylation site of the substrate protein" and the "compound having an activity of binding to the kinase protein" are not particularly limited, and may be known compounds or may be ones identified by screening to be described later. Examples of such compounds include antibodies capable of binding to the phosphorylation site of the substrate protein or the kinase protein, and low-molecular-weight compounds capable of binding to the phosphorylation site of the substrate protein or the kina se protein.

An "antibody" in the present invention may be a polyclonal antibody, a monoclonal antibody, or a functional fragment of an antibody. The antibody includes all classes and subclasses of immunoglobulins. The "functional fragment" of an antibody means a part (partial fragment) of an antibody and capable of specifically recognizing an antigen thereof. Concretely, examples thereof include Fab, Fab', F(ab')2, a variable region fragment (Fv), a disulfide bonded Fv, a single chain Fv (scFv), a sc(Fv)2, a diabody, a polyspecific antibody, polymers thereof, and the like. Moreover, the antibody includes a chimeric antibody, a humanized antibody, a human antibody, and functional fragments of these antibodies. Further, the amino acid sequences of these antibodies may undergo alteration, modification, or the like as necessary. Those skilled in the art can prepare such antibodies as appropriate by known antibody preparation methods. Furthermore, in a case where the agents for diagnosing Alzheimer's disease of the present invention or agents for treating the disease to be described later are to be introduced into human, preferable among these antibodies are a humanized antibody, a human antibody, and functional fragments of these antibodies, from the viewpoint that an immunoreaction hardly occurs with the introduced antibody.

In addition, the "compound having an activity of binding to the phosphorylation site of the substrate protein" and the "compound having an activity of binding to the kina se protein" preferably have a labeling substance bound thereto for the detection by the above-described detection methods using an antibody, bioimaging techniques, and the like. The labeling substance is selected as appropriate in accordance with the type of the detection method employed and the like. Examples thereof include radioactive labeling substances, fluorescent labeling substances, paramagnetic labeling substances, superparamagnetic labeling substances, and enzyme labeling substances. Moreover, such labeling substances may be bound to the molecules directly or indirectly. Examples of the indirect binding include bindings utilizing a secondary antibody to which a labeling substance is bound, or a polymer (such as Protein A, Protein B) to which a labeling substance is bound.

The agents of the present invention may comprise, in addition to the compounds, other pharmacologically acceptable ingredients. Examples of such other ingredients include a carrier, an excipient, a disintegrator, a buffer, an emulsifier, a suspension, a stabilizer, a preservative, an antiseptic, and a physiological salt. As the excipient, lactose, starch, sorbitol, D-mannitol, white sugar, or the like can be used.

As the disintegrator, starch, carboxymethyl cellulose, calcium carbonate, or the like can be used. As the buffer, a phosphate, a citrate, an acetate, or the like can be used. As the emulsifier, gum arabic, sodium alginate, traganth, or the like can be used. As the suspension, glyceryl monostearate, aluminium monostearate, methyl cellulose, carboxymethyl cellulose, hydroxymethyl cellulose, sodium lauryl sulfate, or the like can be used. As the stabilizer, propylene glycol, diethylin sulfite, ascorbic acid, or the like can be used. As the preservative, phenol, benzalkonium chloride, benzyl alcohol, chlorobutanol, methylparaben, or the like can be used. As the antiseptic, sodium azide, benzalkonium chloride, para-oxybenzoic acid, chlorobutanol, or the like can be used.

When the diagnostic agents of the present invention are used in vivo, the administration method into the body of a test subject is as described above in the description of <Method for diagnosing Alzheimer's disease>. Moreover, those skilled in the art can adjust an amount of the diagnostic agents of the present invention administered and the number of administrations as appropriate depending on the type of the compounds, the body weight of a test subject, and the like. The number of administrations can be adjusted as appropriate depending on the administration amount, the administration route, and the like.

A product of the diagnostic agents of the present invention or a manual thereof may be provided with an indication stating that the product is used for diagnosing the target disease. Herein, "a product or a manual provided with an indication" means that the indication is provided to a main body, a container, a package, or the like of the product, or the indication is provided to a manual, a package insert, an advertisement, other printed matters, or the like in which information on the product is disclosed.

<Screening Method for Alzheimer's Disease Diagnostic Agent Candidate Compound>

As described above, it has been revealed that the phosphorylations of the substrate proteins such as MARCKS are commonly enhanced in the multiple Alzheimer's disease model mice before the onset of the disease. Further, it has also been revealed that the kinase proteins which phosphorylate these substrate proteins are activated in the Alzheimer's disease model mice before the onset of the disease. Thus, based on such findings, the present invention makes it possible to provide two embodiments of a screening method for a candidate compound for diagnosing Alzheimer's disease described below.

(1) A method comprising the steps of:

bringing a test compound into contact with a phosphorylation site of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB; and selecting the compound if the compound binds to the phosphorylation site.

(2) A method comprising the steps of:
bringing a test compound into contact with at least one kinase protein selected from the group consisting of PKC, CaMK, CSK, Lyn, and b-RAF; and
selecting the compound if the compound binds to the kinase protein.

The test compound used in the screening methods of the present invention is not particularly limited. Examples thereof include expression products of gene libraries, synthetic low-molecular-weight compound libraries, peptide libraries, antibodies, substances released from bacteria; liquid extracts and culture supernants of cells (microorganisms, plant cells, animal cells), purified or partially purified polypeptides, extracts derived from marine organisms, plants, or animals, soils, and random phage peptide display libraries.

The substrate proteins such as MARCKS and the kinase proteins such as PKC used in these screening methods are as described above in the description of <Diagnostic Agent against Alzheimer's Disease>. Nevertheless, the kinase protein is preferably an activated kinase protein. Moreover, from the viewpoint of the easiness of the detection of the binding, a reporter protein (for example, GFP, luciferase), a tag protein for purification (for example, histidine tag, FLAG tag, GST tag), or the like may be added to these proteins. Further, these proteins may be partial peptides, but the substrate proteins and the activated kinase protein need to contain at least a phosphorylation site(s).

Moreover, the detection of the binding to these proteins is not particularly limited, and can be performed by selecting a known method as appropriate. Examples of the known method include a co-immunoprecipitation method, an ELISA method, a method using a detector based on the surface plasmon resonance phenomenon, and a method based on FRET (fluorescence resonance energy transfer).

<Alzheimer's Disease Therapeutic Agent 1>

As will be described later in Examples, it has been revealed that the phosphorylations of the substrate proteins such as MARCKS are commonly enhanced in the multiple Alzheimer's disease model mice before the onset of the disease. Further, it has also been found that suppressing expressions of the substrate proteins using shRNA successfully suppresses a pathology (abnormal spine formation) in the Alzheimer's disease model mice.

Thus, the present invention provides an agent for treating Alzheimer's disease, the agent comprising a compound capable of suppressing a phosphorylation of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB (hereinafter, the agent for treating Alzheimer's disease may also be referred to as simply "therapeutic agent").

The substrate proteins such as MARCKS targeted by the therapeutic agent of the present invention are as described above in the description of <Diagnostic Agent against Alzheimer's Disease>. In addition, "suppressing" of a phosphorylation of a substrate protein and related terms mean to include not only complete suppression (inhibition) but also partial suppression of the phosphorylation.

Moreover, the suppression of the phosphorylation of the substrate protein can also be achieved by suppressing the expression of the substrate protein per se. Thus, the "compound capable of suppressing the phosphorylation of the substrate protein" also includes a "compound capable of suppressing the expression of the substrate protein."

The "compound capable of suppressing the phosphorylation of the substrate protein" is not particularly limited, and may be a known compound or may be one identified by the screening to be described later. Examples of such a compound include antibodies capable of binding to a phosphorylated site of the substrate protein, low-molecular-weight compounds capable of binding to a phosphorylated site of the substrate protein, RNAs capable of binding to a transcription product of a gene encoding the substrate protein, and peptides having a dominant negative phenotype against the substrate protein. Regarding the antibodies, see <Diagnostic Agent against Alzheimer's Disease>. Regarding such "RNAs capable of binding to a transcription product of a gene encoding a protein" and "peptides having a dominant negative phenotype against a protein," see the description to be described later.

Note that, in the present invention, the term "phosphorylated site" means a site having at least 3 amino acids including one amino acid before and one amino acid after a phosphorylated amino acid in a protein obtained as a result of phosphorylation such as the substrate protein.

<Alzheimer's Disease Therapeutic Agent 2>

As will be described later in Examples, it has also been revealed that the kinase proteins which phosphorylate the substrate proteins are activated in the Alzheimer's disease model mice before the onset of the disease. Further, it has also been found that suppressing the activations of the kinase proteins by using an inhibitor against the proteins successfully suppresses the pathology in the Alzheimer's disease model mice.

Thus, the present invention also provides, as a second embodiment of the therapeutic agent against Alzheimer's disease, an agent comprising a compound capable of suppressing an activity or expression of at least one kinase protein selected from the group consisting of PKC, CaMK, CSK, Lyn, and b-RAF.

The kinase proteins such as PKC targeted by the therapeutic agent of the present invention are as described above in the description of <Diagnostic Agent against Alzheimer's Disease>. In addition, "suppressing" of an activity or expression of a kinase protein and related terms mean to include not only complete suppression (inhibition) but also partial suppression of the activity or expression.

The "compound capable of suppressing the expression or activity of the kinase protein" is not particularly limited, and may be a known compound or may be one identified by the screening to be described later. Examples of such a compound include low-molecular-weight compounds capable of binding to the kinase protein, RNAs capable of binding to a transcription product of a gene encoding the kinase protein, antibodies against the kinase protein, and peptides having a dominant negative phenotype against the kinase protein.

Examples of the low-molecular-weight compound for PKC include PKC inhibitors such as Go6976, UCN-01, BAY43-9006, RO318220, RO320432, Isis3521, LY333531, LY379196, bisindolylmaleimide, sphingosine, staurosporine, midosutaurin, tyrphostin 51, hypericin, enzastaurin, rottlerin, safingol, bryostatin 1, perifosine, and llmofosine. Examples thereof for CaMK include CaMK inhibitors such as KN-93, KN-62, AIP, CaM kinase II inhibitor 281-301, lavendustin C, K252a, rottlerin, ML-7, ML-9, STO-609, W-7, and W-5. Examples thereof for CSK include CSK inhibitors such as TBCA, IQA, TMCB, quinalizarin, quercetin, and apigenin. Moreover, an example thereof for Lyn includes INNO-406 (NS-187). Examples thereof for b-RAF include b-raf inhibitors such as PLX-4720 (N-[3-[(5-chloro-1H-pyrrolo[2,3-b]pyridin-3-yl)carbonyl]-2,4-difluorophenyl]-1-propanesulfonamide), sorafenib (4-[4-[3-[4-chloro-3-(trifluoromethyl)phenyl]ureido]phenoxy]-N- methylpyridine-2-carboxamide), GDC-0879 (2-{4-[(1E)-1-(hydroxyimino)-2,3-dihydro-1H-inden-5-yl]-3-(pyridine-4-yl)-1H-pyrazol-1-yl)ethan-1-ol), vemurafenib (PLX4032, RG7204, N-{3-[5-(4-chlorophenyl)-1H-pyrrolo[2,3-b]pyridine-3-carbonyl]-2,4-difluorophenyl}propane-1-sulfonamide), dabrafenib (N-[3-[5-(2-aminopyridin-4-yl)-2-tert-butyl-1,3-thiazol-4-yl]-2-fluorophenyl]-2,6-difluorobenzenesulfonamide sorafenib tosylate (4-(4-{3-[4-chloro-3-(trifluoromethyl)phenyl]ureido}phenoxy)-$N^2$-methylpyridine-2-carboxamide mono(4-methylbenzenesulfonate), and LGX818 (methyl[(2S)-1-{[4-(3-{5-chloro-2-fluoro-3-[(methylsul fonyl)amino]phenyl}-1-isopropyl-1H-pyrazol-4-yl)-2-pyrimidinyl]amino}-2-propanyl]carbamate).

In the present invention, examples of the "RNAs capable of binding to a transcription product of a gene encoding a protein" include dsRNAs (double-stranded RNAs), such as siRNAs and shRNAs (short haipin RNAs), complementary to the transcription product of the gene encoding the substrate protein or the kinase protein. The length of such a dsRNA is not particularly limited, as long as the expression of the target gene can be suppressed and no toxicity is demonstrated. The length is, for example, 15 to 49 base pairs, preferably 15 to 35 base pairs, and furthermore preferably 21 to 30 base pairs. The dsRNA does not necessarily have to have completely the same base sequence as that of the target gene, but the homology of the sequences is at least 70% or more, preferably 80% or more, and furthermore preferably 90% or more (for example, 95%, 96%, 97%, 98%, 99% or more). The homology of the sequences can be determined with a BLAST program.

Examples of other forms of the "RNAs capable of binding to a transcription product of a gene encoding a protein" include antisense RNAs complementary to the transcription product of the gene encoding the substrate protein or the kinase protein; and RNAs (ribozymes) having a ribozyme activity of specifically cleaving the transcription product.

The above-described RNAs may have some or all of RNAs substituted by an artificial nucleic acid such as PNA, LNA, or ENA. Moreover, in order to express these RNAs in a target to which the agent of the present invention is administered, each of the RNAs may be in the form of an expression vector carrying a DNA encoding the RNA. Additionally, those skilled in the art can prepare such RNAs by chemical synthesis using a commercially-available synthesizer or the like.

Examples of the "peptides having a dominant negative phenotype against a protein" for the substrate protein include polypeptides (for example, partial peptides and decoy peptides containing a phosphorylated site of the substrate protein) which compete with a kinase protein in binding to a binding site on a substrate protein, and the like. Moreover, examples thereof for the kinase protein include polypeptides (for example, partial peptides containing a phosphorylated site of the kinase protein) which competitively inhibit the activation of the kinase protein, and the like.

<Alzheimer's Disease Therapeutic Agent 3>

As described above, it has been revealed that suppressing the phosphorylations of the substrate proteins such as MARCKS successfully suppresses the pathology in the Alzheimer's disease model mice. Thus, the pathology can also be suppressed by suppressing bindings, which are required for the phosphorylations, between the substrate proteins such as MARCKS and the kinase proteins such as PKC.

Based on such findings, the present invention also provides, as a third embodiment of the therapeutic agent against Alzheimer's disease, an agent comprising a compound capable of suppressing a binding of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB to at least one kinase protein selected from the group consisting of PKC, CaMK, CSK, Lyn, and b-RAF.

The substrate proteins such as MARCKS and the kinase proteins such as PKC targeted by the therapeutic agent of the present invention are as described above in the description of <Diagnostic Agent against Alzheimer's Disease>. Nevertheless, the substrate proteins are preferably not phosphorylated, while the kinase proteins are preferably activated kinase proteins. In addition, "suppressing" of a binding between these proteins and related terms mean to include not only complete suppression (inhibition) but also partial suppression of the binding. The "compound capable of suppressing the binding" is not particularly limited, and may be a known compound or may be one identified by the screening to be described later. Examples of such a compound include polypeptides, antibodies, and low-molecular-weight compounds all of which compete with the substrate proteins and the kinase proteins in binding to a binding site on the substrate proteins or the kinase proteins. Note that the low-molecular-weight compounds of the present invention also include physiologically acceptable salt or solvate forms of the low-molecular-weight compounds.

<Alzheimer's Disease Therapeutic Agent 4>

As will be described later in Examples, it has been revealed that activating Lyn also successfully suppresses the pathology in the Alzheimer's disease model mice. Thus, the present invention also provides, as a therapeutic agent against Alzheimer's disease, an agent comprising a compound capable of activating Lyn. Lyn targeted by the therapeutic agent of the present invention is as described above in the description of <Diagnostic Agent against Alzheimer's Disease>.

The "compound capable of activating Lyn" is not particularly limited, and may be a known compound. Examples of such a compound include low-molecular-weight compounds capable of binding to Lyn. More concretely, examples thereof include Lyn kinase activators described in International Publication No. WO2008/103692 (MLR-1023 and the like).

In addition, increasing an amount of Lyn expressed can also increase the activity of Lyn. Thus, the "compound capable of activating Lyn" also includes: nucleic acids (DNA, RNA) encoding Lyn; DNA constructs (for example, plasmid DNA, viral vector) capable of expressing Lyn, which is encoded by the nucleic acids, in target cells; and Lyn proteins.

Hereinabove, preferred embodiments of the therapeutic agent of the present invention have been described. In addition, the therapeutic agent of the present invention may comprise, besides the above-described compounds, the aforementioned other pharmacologically acceptable ingredients, as in the case of the diagnostic agents described above. Further, the therapeutic agent of the present invention may also comprise a carrier for introducing a nucleic acid, a protein, or the like into cells. Examples of the carrier include substances having a positive charge such as cationic liposome, and lipophilic substances (cholesterols and derivatives thereof, lipids (such as, for example, glycolipids, phospholipids, sphingolipids), vitamins such as vitamin E (tocopherols)). Additionally, the therapeutic agent of the present invention may be used in combination with known pharmaceutical drugs which are used in the treatment of Alzheimer's disease.

The mode of administering the therapeutic agent of the present invention is not particularly limited, and examples thereof include intravenous administration, intraarterial administration, intraperitoneal administration, subcutaneous administration, intradermal administration, tracheobronchial administration, rectal administration and intramuscular administration, administration by transfusion, and direct administration into a target site (such as brain). From the viewpoints that the therapeutic effect is high and that an amount of the agent to be administered is small, the direct administration into a target site is preferable. The administration to a target site can be achieved by employing, for example, cannula (catheter), surgical incision, drug delivery system, injection, or the like. More concretely, examples thereof include a method in which a cannula or the like is inserted by stereotactic surgery to administer the agent into the brain through the cannula; a method in which after a craniotomy, a sustained-release drug delivery system (for example, ALZET osmotic pump) with the agent is implanted into the brain; and a method in which the agent is introduced into cells in the brain by electropolation. Meanwhile, in the case where the agent of the present invention is not directly administered into the brain, it is possible to utilize a method in which a brain barrier-permeable substance is bound to the compound and administered. Note that an example of the brain barrier-permeable substance includes a 29-amino-acid glycoprotein derived from rabies virus (see Nature, 2007 July 5, Vol. 448, pp. 39 to 43), but is not limited thereto.

An amount of the therapeutic agent of the present invention administered and the number of administrations can be adjusted as appropriate depending on the type of the compounds, the body weight and symptom of a test subject, and the like. The number of administrations can be adjusted as appropriate depending on the administration amount, the administration route, and the like.

A product of the therapeutic agent of the present invention or a manual thereof may be provided with an indication stating that the product is used for treating Alzheimer's disease. "A product or a manual provided with an indication" is as described above in the description of <Diagnostic Agent against Alzheimer's Disease>. The indication may include information on an action mechanism of the agent of the present invention such as information that administering the agent of the present invention suppresses phosphorylations of the substrate proteins such as MARCKS, thereby suppressing abnormal spine formation or the like, and alleviating a pathology of Alzheimer's disease.

Moreover, the present invention also makes it possible to treat Alzheimer's disease by administering the compound to a subject as described above. Thus, the present invention also provides a method for treating Alzheimer's disease, the method characterized by comprising administering to a subject any one of: a compound capable of suppressing a phosphorylation of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB; a compound capable of suppressing an activity or expression of at least one kinase protein selected from the group consisting of PKC, CaMK, CSK, Lyn, and b-RAF; a compound capable of suppressing a binding of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB to at least one kinase protein selected from the group consisting of PKC, CaMK, CSK, Lyn, and b-RAF; and a compound capable of activating Lyn.

<Screening Method 1 for Alzheimer's Disease Therapeutic Agent Candidate Compound>

As described above, it has been found that suppressing the expressions of the substrate proteins such as MARCKS in the Alzheimer's disease model mice suppresses the phosphorylations of the protein, thereby successfully suppressing the pathology in the mice. Thus, based on such findings, the present invention al so provides the following screening method for a candidate compound for treating Alzheimer's disease, the method comprising:

(i) a step of applying a test compound to a system capable of detecting a phosphorylation of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB; and (ii) a step of selecting the compound if the compound suppresses the phosphorylation of the substrate protein.

The "substrate proteins such as MARCKS" used in this screening method are as described above in the description of <Screening Method for Alzheimer's Disease Diagnostic Agent Candidate Compound>. These proteins may be partial peptides, but need to contain at least a phosphorylated site(s). Moreover, other proteins such as a tag protein for purification may be added to these proteins.

Further, the "test compound" used in this screening method is not particularly limited. Examples thereof include the compounds described above in <Screening Method for Alzheimer's Disease Diagnostic Agent Candidate Compound>.

The "system capable of detecting the phosphorylation of the substrate protein" is not particularly limited. An example thereof includes a mixture solution of the substrate proteins such as MARCKS and the kinase proteins (such as PKC) which phosphorylate the substrate proteins. Moreover, a radiolabeled phosphate is added together with a test compound to this mixture solution, followed by incubation to detect the incorporation of the phosphate into the substrate protein with a scintillation counter, by autoradiography, or other means. Then, if an amount of the phosphate incorporated into the substrate protein detected in the presence of the test compound is small in comparison with that detected in the absence of the test compound, the test compound is evaluated as a compound which suppresses the phosphorylation of the substrate protein, and selected as a candidate compound for treating Alzheimer's disease.

Additionally, an example of another embodiment of the "system capable of detecting the phosphorylation of the substrate protein" includes a system capable of directly detecting the phosphorylation of the substrate protein such as MARCKS. Regarding this system, a test compound is applied to cells expressing the substrate protein or cells in which the protein is forcibly expressed, and the phosphorylation of the substrate protein in the cells is detected. Then, if an amount of the phosphorylated substrate protein detected is small in comparison with that detected in the absence of the test compound, the test compound is evaluated as a compound which suppresses the phosphorylation of the substrate protein. In the case where the phosphorylation of the substrate protein is directly detected, it is suitable to employ a detection method using an antibody capable of specifically binding to a phosphorylation site of a substrate protein, a method utilizing a detector based on the surface plasmon resonance phenomenon using a thin metal film on which a compound capable of specifically binding to a phosphorylation site of a substrate protein is immobilized, and the like as in <Method 1 for Diagnosing Alzheimer's Disease> described above.

<Screening Method 2 for Alzheimer's Disease Therapeutic Agent Candidate Compound>

As described above, it has been found that suppressing activations of the kinase proteins such as PKC in the Alzheimer's disease model mice also successfully suppresses the pathology in the mice. Thus, based on such a finding, the present invention also provides the following method as a second embodiment of the screening method for a candidate compound for treating Alzheimer's disease, the method comprising:

(i) a step of applying a test compound to a system capable of detecting an activity or expression of at least one kinase protein selected from the group consisting of PKC, CaMK, CSK, Lyn, and b-RAF; and (ii) a step of selecting the compound if the compound suppresses the activity or expression of the protein.

As in <Method for Diagnosing Alzheimer's Disease> described above, the "kinase proteins such as PKC" used in this screening method are not limited respectively to the proteins having the amino acid sequences listed as the typical examples described above, and naturally-occurring mutants thereof can also be targeted.

The "system capable of detecting the activity of the kinase protein such as PKC" should be a system capable of detecting the activity of the kinase protein, that is, the phosphorylation of the substrate protein. It is suitable to use the systems described above in <Screening Method 1 for Alzheimer's Disease Therapeutic Agent Candidate Compound>. Moreover, since a phosphorylation of a substrate protein requires the activation (such as phosphorylation) of a kinase protein per se, a "system capable of detecting a phosphorylation of a kinase protein such as PKC" may also be used. Note that this system is constructed using the kinase proteins such as PKC in place of the substrate proteins such as MARCKS in the "system capable of detecting the phosphorylation of the substrate protein" described above.

Examples of the "system capable of detecting the expression of the kinase protein such as PKC" include cells having a DNA in which a reporter gene is operably linked downstream of a promoter region of a gene encoding the each kinase protein, or liquid extracts from the cells. Herein, the phrase "operably linked" refers to linking of the reporter gene to the promoter region of each gene such that the expression of the reporter gene is induced by binding of a transcription factor to the promoter region of the gene. Moreover, a test compound is applied to this system to measure an activity of a protein encoded by the reporter gene. If the detected activity is low in comparison with that detected in the absence of the test compound, the test compound is evaluated as having an activity of suppressing the expression of each kinase protein.

An example of another embodiment of the "system capable of detecting the expression of the kinase protein such as PKC" besides the above-described reporter system includes a system capable of directly detecting the expression of the kinase protein such as PKC. Regarding this system, a test compound is applied to cells expressing each protein, and the expression of each protein in the cells is detected. Then, if an detected amount of each protein expressed is small in comparison with that detected in the absence of the test compound, the test compound is evaluated as having an activity of suppressing the expression of the protein. In detecting the expression of the protein, in the case where the expression of the protein per se is to be detected, it is suitable to employ a detection method using an antibody capable of specifically binding to a kinase protein (preferably, activated kinase protein), a method utilizing a detector based on the surface plasmon resonance phenomenon using a thin metal film on which a compound capable of specifically binding to a kinase protein (preferably, activated kinase protein) is immobilized, and the like as in <Method 2 for Diagnosing Alzheimer's Disease> described above. Meanwhile, in a case of detecting the expression of the kinase protein through the gene expression at a transcription level, a northern blotting method, an RT-PCR method, a dot blotting method, or the like can be employed.

<Screening Method 3 for Alzheimer's Disease Therapeutic Agent Candidate Compound>

As described above, it has been revealed that suppressing the phosphorylations of the substrate proteins such as MARCKS successfully suppresses the pathology in the Alzheimer's disease model mice. Thus, the pathology can also be suppressed by suppressing bindings, which are required for the phosphorylations, between the substrate proteins such as MARCKS and the kinase proteins such as PKC.

Based on such findings, the present invention also provides the following method as a third embodiment of the screening method for a candidate compound for treating Alzheimer's disease.

A screening method for a candidate compound for treating Alzheimer's disease, the method comprising the following steps (a) to (c):

(a) a step of bringing at least one kinase protein selected from the group consisting of PKC, CaMK, CSK, Lyn, and b-RAF into contact with at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB, in presence of a test compound;

(b) a step of detecting a binding between the kinase protein and the substrate protein; and (c) a step of selecting the compound if the compound suppresses the binding.

The "kinase proteins such as PKC," the "substrate proteins such as MARCKS," and the "test compound" used in this screening method are as described above in the description of <Screening Method for Alzheimer's Disease Diagnostic Agent Candidate Compound>. Nevertheless, the substrate proteins are preferably not phosphorylated, while the kinase proteins are preferably activated kinase proteins.

In the step (a), the kinase protein and the substrate protein are brought into contact with each other in the presence of the test compound. The contact should be conducted under conditions that would not inhibit the binding in the absence of the test compound.

In the step (b), the binding between the kinase protein and the substrate protein is detected. This binding detection is not particularly limited, and a known method can be employed as appropriate. For example, it is possible to employ a co-immunoprecipitation method, an ELISA method, a method using a detector based on the surface plasmon resonance phenomenon, or a method based on FRET.

In the step (c), the compound is selected if the compound suppresses the binding. For example, when the co-immunoprecipitation method is employed, the evaluation is possible by comparison between an amount of the substrate protein coprecipirated when the kinase protein is precipitated by an antibody specific thereto in the presence of the test compound and an amount (control value) of the substrate protein in the absence of the test compound. To be more specific, if the amount of the substrate protein in the presence of the test compound is small in comparison with the amount in the absence of the test compound, the test compound can be evaluated as a candidate compound for treating Alzheimer's disease. When a method other than the immunoprecipitation method is employed in the detection of the binding, a similar evaluation is possible by using the degree of the binding in the absence of the test compound as a control value.

Hereinabove, preferred embodiments of the screening method for a candidate compound for treating Alzheimer's disease of the present invention have been described. In addition, in the screening method of the present invention, it is possible to further narrow down a candidate compound on the basis of a recovery from a symptom of an Alzheimer's disease model animal in which the compound selected according to the above-described methods has been administered.

Examples of the "Alzheimer's disease model animals" include, as described later in Examples, animals (such as mice, rats, marmosets) in which an Alzheimer's disease responsible gene (such as PS1 exon 9 deletion mutant; PS2 mutant (N141I); human double-mutant APP695 (KM670/671NL, Swedish type); quintuple mutant (human APP695 triple mutant with Swedish type (KM670/671NL), Florida type (1716V), and London type (V717I), as well as human PS1 double mutant (M146L and L285V)); human tau mutant; or a combination of these mutants) is introduced.

The "recovery from a symptom of a model animal" can be detected, for example, as described later in Examples, by performing in vivo imaging with a two-photon microscope on the degree of a recovery from abnormal spine formation caused by Alzheimer's disease. Moreover, the detection is also possible by conducting a behavioral test described later in Examples and evaluating the degree of a recovery from an abnormal behavior of the model animal.

Hereinabove, preferred embodiments of the diagnosis method, the diagnostic agent, and the therapeutic agent against Alzheimer's disease, the screening methods for candidate compounds of these agents of the present invention, and so forth have been described. Hereinafter, description will be given of a diagnostic agent, a therapeutic agent, and so forth against frontotemporal lobar degeneration.

<Method for Diagnosing Frontotemporal Lobar Degeneration>

As will be described later in Examples, it has been revealed that a b-RAF protein which is a kinase protein phosphorylating substrate proteins such as tau protein is activated in frontotemporal lobar degeneration model mice before the onset of the disease. Thus, the present invention also provides a method for diagnosing frontotemporal lobar degeneration, the method comprising the following steps (i) to (iii):

(i) a step of detecting an activity or expression of a b-RAF protein in a test subject;

(ii) a step of comparing the activity or expression with an activity or expression of a b-RAF protein in a normal subject; and (iii) a step of determining that the test subject is affected with frontotemporal lobar degeneration or has a risk of developing frontotemporal lobar degeneration if the activity or expression of the b-RAF protein in the test subject is higher than the activity or expression of the b-RAF protein in the normal subject as a result of the comparison.

This diagnosis method is a method similar to <Method for Diagnosing Alzheimer's Disease> described above. In addition, examples of the "activated kinase protein" to be detected include, as described above, b-RAF having serine at position 365 phosphorylated, b-RAF having serine at position 446 phosphorylated, b-RAF having serine at position 579 phosphorylated, b-RAF having threonine at position 599 phosphorylated, b-RAF having serine at position 602 phosphorylated, b-RAF having serine at position 729 phosphorylated, and b-RAF having serine at position 732 phosphorylated. From the viewpoint of having a larger difference between a subject affected with frontotemporal lobar degeneration or having a risk of developing and a normal subject, the detection target in the method for diagnosing frontotemporal lobar degeneration of the present invention is preferably b-RAF having serine at position 365 phosphorylated, b-RAF having serine at position 729 phosphorylated, and b-RAF having serine at position 732 phosphorylated, and the detection target is more preferably b-RAF having serine at position 729 phosphorylated.

Moreover, the present invention makes it possible to determine that one is affected with frontotemporal lobar degeneration or has a risk of developing frontotemporal lobar degeneration. In this manner, enabling judgment of frontotemporal lobar degeneration affection or the like at an early stage leads to an expectation that treatment methods for suppressing a pathology of frontotemporal lobar degeneration (such a method for administering an agent for suppressing a pathology of frontotemporal lobar degeneration) will be effective.

Thus, the present invention also makes it possible to provide, as in the case of <Method for Diagnosing Alzheimer's Disease> described above, a method for treating frontotemporal lobar degeneration, the method comprising a step of administering an agent for suppressing a pathology of frontotemporal lobar degeneration to a test subject determined to be affected with frontotemporal lobar degeneration or have a risk of developing frontotemporal lobar degeneration by the diagnosis method of the present invention.

Additionally, examples of the agent administered to suppress a pathology of frontotemporal lobar degeneration include serotonin-specific reuptate inhibitors (SSRI), cholinesterase inhibitors (ChEI), agents for suppressing tau aggregation (such as aminothienopyridazine, cyanine dye, methylene blue), and neuroprotective drugs (such as dimebon).

Further, as will be described later, it is also possible to suitably use, as the agent for suppressing a pathology of frontotemporal lobar degeneration, an agent for treating frontotemporal lobar degeneration, the agent comprising a compound capable of suppressing an activity or expression of a b-RAF protein.

<Diagnostic Agent Against Frontotemporal Lobar Degeneration>

As described above, it has been revealed that the kinase protein b-RAF which phosphorylates the substrate proteins such as tau protein is activated before the onset of the disease. Thus, the present invention provides an agent for diagnosing frontotemporal lobar degeneration, the agent comprising a compound having an activity of binding to b-RAF.

As in the case of <Method for Diagnosing Alzheimer's Disease> described above, the b-RAF protein targeted by the diagnostic agent against frontotemporal lobar degeneration of the present invention is not limited to the proteins having the amino acid sequences listed as the typical examples described above, and naturally-occurring mutants can also be targeted. Moreover, the "compound having an activity of binding to b-RAF" is not particularly limited, and it is possible to similarly use the compounds described above in <Diagnostic Agent against Alzheimer's Disease>.

<Therapeutic Agent Against Frontotemporal Lobar Degeneration>

As will be described later in Examples, it has also been revealed that the b-RAF protein which phosphorylates the substrate proteins such as tau protein is activated in the frontotemporal lobar degeneration model mice before the onset of the disease. Further, it has also been found that suppressing the activation of the b-RAF protein by using an inhibitor against the protein successfully suppresses the pathology in the frontotemporal lobar degeneration model mice.

Thus, the present invention also provides, as a therapeutic agent against frontotemporal lobar degeneration, an agent comprising a compound capable of suppressing an activity or expression of b-RAF.

The frontotemporal lobar degeneration therapeutic agent of the present invention is similar to <Alzheimer's disease therapeutic agent> described above. Moreover, the targeted b-RAF protein is as described above in the description of <Diagnostic Agent against Frontotemporal Lobar Degeneration>.

As in the case of <Alzheimer's disease therapeutic agent> described above, a product of the frontotemporal lobar degeneration therapeutic agent of the present invention or a manual thereof may be provided with an indication stating that the therapeutic agent is used for treating frontotemporal lobar degeneration. "A product or a manual provided with an indication" is as described above in the description of <Diagnostic Agent against Alzheimer's Disease>. The indication may include information on an action mechanism of the agent of the present invention such as information that administering the agent of the present invention suppresses b-RAF activity, thereby suppressing a decrease in the number of spines and so forth, and alleviating a pathology of frontotemporal lobar degeneration.

Moreover, the present invention also makes it possible to treat frontotemporal lobar degeneration by administering the compound to a subject as described above. Thus, the present invention also provides a method for treating frontotemporal lobar degeneration, the method characterized by comprising administering to a subject a compound capable of suppressing an activity or expression of b-RAF.

EXAMPLES

Hereinafter, the present invention will be more specifically described on the basis of Examples. However, the present invention is not limited to the following Examples.

—Alzheimer's Disease—

In the present Examples, first, experimental methods and so forth described below were carried out to identify phosphoproteins and kinase proteins which played central roles in a pre-onset stage of Alzheimer's disease, as well as a network composed of these proteins, and consequently to provide target molecules useful in the diagnosis and treatment of Alzheimer's disease.

<Experiments Using Model Mice>

The following five types of Alzheimer's disease model mice were used in the present Examples.
(1) PS1 transgenic mice (mice expressing exon 9 deletion mutant (PSEN1dE9) under the control of the mouse PrP promoter; see Jankowsky, J. L. et al., Hum. Mol. Genet., 2004, Vol. 13, pp. 159 to 170)
(2) PS2 transgenic mice (mice expressing human PS2 mutant (N141I) under the control of the ubiquitous CMV early enhancer and the chicken β actin promoter; see Oyama, F. et al., J. Neurochem., 1998, Vol. 71, pp. 313 to 322)
(3) Human double-mutant APP695 (KM670/671NL, Swedish type) transgenic mice (the mice were prepared by substituting a mutant for the PrP gene in a hamster PrP cosmid vector (see Hsiao, K. et al., Science, 1996, Vol. 274, pp. 99 to 102))
(4) 5xFAD mice (transgenic mice expressing human APP695 having Swedish type (KM670/671NL), Florida type (I716V), and London type (V717I) triple mutations, as well as human PS1 having double mutations (M146L and L285V) under the control of mouse Thy1) (see Oakley, H. et al., J. Neurosci., 2006, Vol. 26, pp. 10129 to 10140)
(5) Transgenic mice expressing a human tau mutant protein under the control of the mouse PrP promoter (see Yoshiyama, Y. et al., Neuron, 2007, Vol. 53, pp. 337 to 351).

Note that the genetic backgrounds of the transgenic mice were C57BL/6J, C57BL/6J, C57/B6XSJL, C57/B6XSJL, and B6C3H/F1, respectively.

In the mass spectrometry to be described later, brain tissues were isolated from male transgenic mice described above at the age in months shown in figures and descriptions thereof, and subjected to the analysis.

In the immunohistochemical analysis, the brain samples were fixed with 4% paraformaldehyde, and paraffin sections were prepared (the thickness of each section: 5 μm) using a microtome (manufactured by Yamato Kohki Industrial Co., Ltd.). Meanwhile, the following antibodies were each diluted to 1/1000 and used as primary antibodies.

Anti-Aβ antibody (82E1), manufactured by IBL Co., Ltd., Code No: 10323
Anti-Aβ antibody (6E10), manufactured by Covance Inc., Product Code: SIG-39300
Anti-human PHF-tau antibody (AT-8), manufactured by Innogenetics N.V., Catalog No: BR-03.

Then, the tissue samples reacted with each antibody were treated with VECTASTAIN Elite ABC Kit and DAB Peroxidase Substrate Kit (manufactured by Vector Laboratories) to visualize the expressions of proteins recognized by the antibodies.

Moreover, although unillustrated, male transgenic mice described above were subjected to six behavioral tests described below. Based on detected abnormal behaviors, whether or not these mice developed Alzheimer's disease was evaluated.
(1) Morris Water Maze Test In this test, the mice received a 60-second trial four times a day for 5 days. The time until each mouse reached the platform was measured.
(2) Rotarod Test In this test, a trial was conducted four times a day for 3 days in which a mouse was allowed to grab on a rotating rod (rotation speed: 3.5 to 35 rpm) with the speed being gradually increased. The average time until the mouse fell from the rotating rod was recorded.
(3) Fear-Conditioning Test In this test, first, a mouse received a sound stimulus (65-dB white noise, 30 seconds) together with an electrical stimulus (0.4 mA, 2 seconds) on the foot. Then, after 24 hours, the mouse was measured for the frequency of the freezing reaction when the mouse received a sound stimulus but no electrical stimulus in the same chamber.

(4) Open-Field Test

In this test, the time during which a mouse stayed in a central region of an open field was measured.

(5) Light-Dark Box Test

In this test, the time during which a mouse stayed in a light box was measured.

(6) Elevated Plus Maze Test

In this test, the time during which a mouse stayed on arms with no walls in an elevated plus maze set 60 cm above the floor was measured.

<Human Brain>

For a proteome analysis to be described later, brain samples were isolated from AD (Alzheimer's disease) patients, DLB (dementia with lewy bodies) patient, and healthy control persons and frozen at −80° C. within 1 hour after death. Moreover, temporal pole and occipital pole tissues were dissected from five brains in each group.

Note that a neuropathologist pathologically diagnosed each brain sample based on the immunohistochemistry. As a result, in the brains of the AD patients, other pathologies such as lewy bodies, TDP43 cytoplasmic aggregates, and argyrophilic grains were not observed. Moreover, in the brains of the DLB patients, the disease-specific pathological observation was confirmed.

<Preparation of Phosphoproteins and Phosphopeptides>

In preparing phosphoproteins and phosphopeptides from the transgenic mice and so forth, first, mice were euthanized using ethyle ether. Within 5 minutes thereafter, the cerebral cortexes were collected. The obtained cerebral cortexes were immediately frozen with liquid nitrogen and stored until phosphoproteins were extracted. In the protein extraction, first, the cortical tissues were lysed with a cold lysis buffer containing 2% SDS, 1 mM DTT, and 100 mM Tris-HCl (pH 7.5). The cells were disrupted with 20 strokes of a glass Dounce homogenizer on ice. The ratio of the lysis buffer to the tissue was 10 µL to 1 mg. After the cells were disrupted, the lysate was incubated at 100° C. for 15 minutes. Then, the crude extract was obtained by centrifugation at 4° C. at 16000×g for 10 minutes. The collected supernant was diluted to a 1/10 concentration with water, and filtered through a filter having a pore diameter of 0.22 µm. The resulting flow-through fraction was concentrated to a 10-fold concentration using an Ami con Ultra 3K filter (manufactured by Millipore Corporation). Further, the concentrations of proteins thus prepared were measured using the BCA Protein Assay Reagent (manufactured by Thermo Fisher Scientific Inc.).

Subsequently, a solution of 100 µL of 1 M triethylammonium bicarbonate (TEAB) (pH 8.5), 3 µL of 10% SDS, and 30 µL of 50 mM tris-2-carboxyethyl phosphine (TCEP) was added to sample aliquots (200 µL) containing 15 mg of the proteins, and incubated at 60° C. for 1 hour. Moreover, to protect cysteine residues, 10 mM methyl methanethiosulfonate (MMTS) was added and treated at 25° C. for 10 minutes. Thereafter, the obtained sample was treated at 37° C. for 24 hours with 80 mM $CaCl_2$ and trypsin (mass spectrometry grade) (10:1 protein/enzyme, w/w). Then, phosphopeptides were concentrated using TITANSPHERE (registered trademark) Phos-Tio Kit (manufactured by GL Sciences Inc.) according to the instruction, and desalted using a Sep-Pak Light C18 cartridge column (manufactured by Waters Corporation) according to the instruction. The sample aliquots were dried and then dissolved in 25 µL of 100 mM TEAB (pH 8.5). Further, the phosphopeptide in each sample were labeled separately us in the iTRAQ (registered trademark) multiplex assay kit (manufactured by AB SCIEX Ins.) at 25° C. for 2 hours according to the instruction. Subsequently, the labeled phosphopeptide pools were mixed together. The obtained aliquots were dried and then re-dissolved in 1 mL of 0.1% formic acid.

<2D LC MS/MS Analysis>

The phosphopeptide samples labeled as described above were subjected to strong cation exchange (SCX)chromatography using a TSK gel SP-5PW column (manufactured by TOSHO Corporation) and a Prominence UFLC system (manufactured by Shimadzu Corporation). Note that the flow rate was 10 mL/minute with solution A (10 mM $KH_2PO_4$ (pH 3.0), 25% acetonitrile). Thereafter, elution was performed using solution B (10 mM $KH_2PO_4$ (pH 3.0), 25% acetonitrile, 1 M KCl) in a gradient range of 0 to 50%. The collected elution fractions were dried and then re-dissolved in 100 µL of 0.1% formic acid.

Subsequently, each fraction thus prepared was analyzed using a DiNa Nano-Flow LC system (manufactured by KYA Technologies Corporation) and Triple TOF 5600 System (manufactured by AB SCIEX Ins.). In the liquid chromatography, samples were loaded onto a 0.1 mm×100 mm C18 column together with solution C (2% acetonitrile and 0.1% formic acid) and eluted using solution D (80% acetonitrile and 0.1% formic acid) in a gradient range of 0 to 50%. Note that the flow rate was set at 300 nL/minute, and the ion spray voltage was set at 2.3 kV. The information-dependent acquisition (IDA) was performed in a range of 400 to 1250 m/z with 2 to 5 charges. Moreover, to identify each peptide, the Analyst TF1.5 software (manufactured by AB SCIEX Ins.) was used. Further, each peptide was quantified based on the TOF-MS current detected during the LC-separated peptide peak, and adjusted to the charge/peptide ratio. In addition, the obtained signals were analyzed using Analyst TF (version 1.5) (manufactured by AB SCIEX Ins.). Then, the signals were processed by ProteinPilot software (version 4).

<Data Analysis>

As described above, in the 2D LC MS/MS analysis, the mass spectra of the peptides were acquired and analyzed using Analyst TF (version 1.5) (manufactured by AB SCIEX Ins.). Then, based on the obtained result, corresponding proteins were searched using human and mouse protein sequence database (UniProtKB/Swiss-Prot, data downloaded from UniProt (www.uniprot.org) on 2010 Jun. 22, with ProteinPilot software (version 4) including Paragon algorithm (manufactured by AB SCIEX Ins., see Shilov, I. V. et al., Mol. Cell. Proteomics, 2007, Vol. 6, pp. 1638 to 1655) as described above. Note that the tolerance for the searched of the peptides by ProteinPilot was set to 0.05 Da for the MS analysis and 0.10 Da for the MS/MS analysis. Moreover, in ProteinPilot, "phosphorylation emphasis" was set at the sample description, and "biological modifications" was set at the processing specification. Further, the confidence score was utilized to evaluate the quality of the peptide identification. Furthermore, the identified proteins were grouped by the ProGroup algorithm (manufactured by AB SCIEX Ins.) to exclude redundancy. Additionally, the threshold value for the protein detection was set at 95% confidence in ProteinPilot. Then, if the confidence was 95% or more, the protein was determined to be identified.

Moreover, an MS/MS spectrum was prepared upon a fragmentation in the mass spectrometer. Further, the proteins were quantified through iTRAQ reporter group analysis in the MS/MS spectrum. In the peptide and protein quantification, bias correction option was used to normalize signals of different iTRAQ reporters. In addition, peptide ratios, that is, ratios between reporter signals in the AD patients and those in control samples, were calculated after the bias correction. A protein ratio (average ratio) was deduced from a weighted average of peptide ratios corresponding to proteins. Moreover, the deduction used peptide ratios differently weighted based on error factors after the bias correction. Note that detailed formulas used to calculate these values were described in the manual from ABSCIEX. Further, using the peptide ratios, amounts of the proteins in the AD patients were compared with those in the control samples. Student's t-value was calculated from weighted average of log peptide ratio, its standard error, and log bias. Furthermore, P-value was calculated together with a post hoc test in ProteinPilot to exclude multiple hypothesis testing-related problem. The P-values of three samples obtained in this test were integrated by inverse normal method. Then, if the integrated P-value was smaller than 0.05, it was determined that the phosphorylations of the proteins were changed.

The peptide summary and protein summary in ProteinPilot were inputted into Excel for further data analyses. Moreover, a geometric mean of signal intensities derived from multiple MS/MS fragments containing the phosphorylation site was calculated as an amount of phosphopeptide fragment. Further, a difference between the AD patient group and the control group was evaluated by Student's t-test (n=3). Then, the changed phosphoproteins were compared among different AD models, and proteins were selected which commonly changed in a hypothesis free approach or an Aβ aggregation-linked approach.

<Systems Biology>

ProteinPilot software was used to identify proteins expressed in the occipital lobe and the temporal lobe of the human brain (see Shilov, I. V. et al., Mol. Cell. Proteomics, 2007, Vol. 6, pp. 1638 to 1655). To be more specific, ProteinPilot automatically added Uniprot ID to each observed protein. Then, the observed proteins were searched for proteins belonging to common Homologene Group ID, and the Taxonomy IDs and Gene IDs of the collected proteins were obtained. Note that the number of the Taxonomy IDs was limited to 9606 for human, 10090 for mouse, and 10116 for rat. Moreover, Uniprot IDs of newly added proteins were also attached. Next, from the list of the collected proteins, proteins having Uniprot IDs not listed in the GNP database (http://genomenetwork.nig.ac.jp/index_e.html) were excluded. Subsequently, a database was created from information collected from the GNP by utilizing a super computer system at the Human Genome Center in the University of Tokyo. As a result, remaining proteins were determined as analyzed proteins. Moreover, the GNP database was searched for proteins linked to the analyzed proteins, so that an edge file was created (redundant edges were excluded). Based on the created edge file, a protein network was obtained and visualized using Cell Illustrator (see Nagasaki, M. et al., Appl. Bioinformatics, 2003, Vol. 2, pp. 181 to 184).

<In Vivo Imaging with Two-Photon Microscope>

Two-photon imaging of dendritic spine was performed using a laser-scanning microscope system FV1000MPE2 (manufactured by Olympus Corporation) equipped with an upright microscope (BX61WI, manufactured by Olympus Corporation, a water-immersion objective lens (XLPlanN25xW; numerical aperture, 1.05), and a pulsed laser (MaiTai HP DeepSee, manufactured by Spectra Physics). In the imaging, EGFP was excited by light at a wavelength of 890 nm, and scanned in a range of 500 to 550 nm. Moreover, the scanned region for three-dimensional imaging was 100×100 µm (1 µm Z-axis steps, 1024×1024 pixels).

Additionally, two weeks before the imaging, adeno-associated virus 1 (AAV1)-EGFP with the synapsin 1 promoter (titer: $1\times10^{10}$ vector genomes/mL, 1 µL) was injected into the retrosplenial cortex (−2.0 mm anteroposterior and 0.6 mm mediolateral from the bregma, depth 1 mm) of mice under anesthesia with 2.5% isoflurane. Then, two weeks thereafter, the dendritic spines of the first layer (layer 1) of the cerebral cortex were observed through a thinned skull window according to the method described in "Yang, G. et al., Nat. Protoc., 2010, Vol. 5, pp. 201 to 208."

Moreover, when the influence of kinase inhibition on dendritic spines was imaged, Alzet micro-osmotic pumps (model: 1003D, manufactured by Durect Corporation) filled with PBS/1% DMSO containing 1 µM Go6976 (manufactured by Calbiochem), 0.4 mM KN-93 (manufactured by Cayman Chemical), or 1 µM MLR1023 (manufactured by Glixx Laboratories) were implanted into mice under anesthesia with $O_2$/isoflurane. Then, 30 hours or 60 hours elapsed after the osmotic pumps were implanted, dendritic spines were observed. Note that, regarding the PKC inhibitor Go6976, see Yan, Z. et al., Proc. Natl. Acad. Sci. U.S.A, 1999, Vol. 96, pp. 11607 to 11612. Regarding the CaMK inhibitor KN-93, see Galan, A. et al., Pain., 2004, Vol. 112, pp. 315 to 323. Regarding the Lyn activator MLR1023, see Saporito, M. S. et al., J. Pharmacol. Exp. Ther., 2012, Vol. 342, pp. 15 to 22.

Meanwhile, when the influence of shRNA-lentiviral vector introduction on dendritic spines was imaged, 3 µL of a lentiviral vector encoding shRNA against MARCKS (sc-35858-V, manufactured by Santa Cruz Biotechnology Inc., $1\times10^6$TU) or scrambled shRNA(RHS4348, $1\times10^6$TU) was injected into the same region as in the case of the AAV1-EGFP.

In addition, the spine density, spine length, spine maximum diameter, and spine neck minimum diameter were measured from the obtained images using image analysis software IMARIS 7.2.2 (manufactured by Bitplane).

<Statistical Analysis>

Mass spectrometry data on the disease model mice or human patients were evaluated by inverse normal method in comparison with data on the respective background mice or human control samples. The amount of each peptide in the mass spectrometry was based on multiple peaks, and the amount of each protein was based on multiple peptide values. In consideration of these, P-values were obtained for these amounts. Moreover, together with the P-values, differential gene expression analysis was performed on each peptide or protein without replication. Further, to guarantee the result quality, biologically replicated data were also obtained which could increase the number of identified proteins. As a result, it was determined that appropriate sample sizes of human and mouse brains were respectively N=5 and N=3.

Note that whether or not all the samples formed normal distribution was not confirmed. Nevertheless, in the process of calculating the P-value with a computer, low-quality measurement results producing abnormal values were excluded in the present analysis using the commercially-available program (ProteinPilot).

Additionally, the results obtained by the animal behavioral tests and two-photon microscope observation were basically analyzed by Student's independent t-test (two-sided test) in the sample sizes shown in figures and descriptions thereof.

Moreover, brain tissue sampling, data collection in the mass spectrometry, and the systems biology analysis were performed by independent researchers without assigning the tasks to groups who knew the circumstances.

Example 1

<Phosphoproteome Analysis on Alzheimer's Disease>

It has been suggested that various phosphorylation signal transductions including tau phosphorylation are involved in a pathology of Alzheimer's disease.

Accordingly, identifying phosphorylation signal transductions in Alzheimer's disease, particularly, a phosphorylation signal transduction which played a central role in a pre-onset stage of Alzheimer's disease, makes it possible to provide very effective target molecules in early-stage diagnosis and treatment of this disease. Hence, the present inventor made efforts to comprehensively analyze (phosphoproteome analysis) phosphorylation signal transductions in Alzheimer's disease to identify a phosphorylation signal transduction which played a central roles in the pathology.

However, a postmortem change in protein phosphorylations basically quite hinders a phosphoproteome analysis targeting human postmortem brain samples. In fact, the present inventor and other researchers have heretofore performed proteome-wide analyses, in the postmortem human brain analysis, on the change in phosphoproteins of mouse brains stored at room temperature or 4° C. for different durations to determine a period during which the brain would reflect the living state before death. As a result, the present inventor and other researchers have revealed that various phosphoproteins had already changed at a time point 12 hours after the preservation was started (Oka, T., Tagawa, K., Ito, H. & Okazawa, H. "Dynamic changes of the phosphoproteome in post mortem mouse brains," PLoS One, 2011, 6, e21405).

Hence, in view of this result, it was considered risky to conduct a phosphoproteome analysis based solely on human samples. Thus, efforts were made to identify phosphoproteins whose expression amounts changed in Alzheimer's disease, by the following stepwise approach: first, analyzing Alzheimer's disease model mice; and then analyzing brain samples of Alzheimer's disease patients. To be more specific, first, the following five types of transgenic mice (four types of AD model mice and one type of Tau model mice) were dissected at the ages of 1, 3, and 6 months (4, 12, and 24 weeks old). Then, the cerebral cortex, hippocampus, and striatum were quickly separated under a microscope and frozen immediately. Note that all of these processes were completed within 5 minutes, as assessed by measuring the time with a stopwatch.

(1) PS1 transgenic mice
(2) PS2 transgenic mice
(3) Human double-mutant APP695 transgenic mice
(4) 5×FAD mice
(5) Tau transgenic mice.

Additionally, the background of the APP-Tg2576 mice and the 5×FAD mice was B6/SJL, the background of the PS1 transgenic mice and the PS2 transgenic mice was C57BL6, and the background of the Tau transgenic mice was C57BL6/C3H. Hence, these background mice were utilized as control mice in the following experiment.

Note that, in the phosphoproteome analysis, preliminary tests by AB SCIEX Triple TOF 5600 mass spectrometry were repeated to determine the optimal conditions allowing the detection of the largest number of phosphoproteins. Moreover, samples were fractionated in multiple stages using cation exchange columns and reverse-phase columns. Data obtained by combined analyses on the same samples were merged. As a result, conditions (appropriate amount, run time) for mass spectrometry allowing such quite a high detection score of confidence 95% were obtained.

Next, using these conditions, a phosphoproteome analysis was performed on the Alzheimer's disease model mice. To be more specific, phosphoproteins were purified from the five types of transgenic mice and the three types of background mice corresponding thereto using TITANSPHERE (registered trademark) Phos-Tio Kit. Then, after labeling with eight different probes using the iTRAQ reagent, the analysis was performed by a single run of the mass spectrometry. Subsequently, the systems biology analysis was performed based on the experimental results of three mass spectrometry analyses. As a result, with 95% confidence, 744 to 1128 phosphoproteins were identified, and 13017 to 29995 phosphopeptides were identified.

Thereafter, the proteins identified by nine mass spectrometry analyses were mapped on the integrated protein-protein interaction (PPI) database using a super computer. The utilized integrated database was the genome network platform (http://genomenetwork.nig.ac.jp/index_e.html) provided by National Institute of Genetics. The integrated database includes the experimentally-supported PPI database of the Human Genome Project (GNP), BIND (www-.bind.ca/), BioGrid (www.thebiogrid.org/), HPRD (www.h-prd.org/), IntAct (www.ebi.ac.uk/intact/site/index.jsf), and MINT (http://mint.bio.uniroma2.it/mint/Welcome.do).

After that, the mapped phosphoproteins were designated as nodes. Further, proteins linked to significantly changed phosphoproteins were attached as accessory nodes. Moreover, links between the proteins were connected by lines (edges). Thus, a mouse default network was prepared. Note that, in this network, proteins indirectly linked to the identified proteins via two or more edges were excluded from the network.

Next, although one protein had multiple P-values of multiple peptides derived therefrom, these P-values were integrated by the inverse normal method, and the integrated P-value was compared between the model mice group and the control mouse group (n=3). Then, as a result of the comparison between the AD model mice or Tau model mice at the ages of 1 to 6 months and their control mice, changed phosphoproteins were selected as nodes (p<0.05). Thus, although unillustrated, networks of the phosphoproteins changed at each time point of each model mouse were constructed.

Next, based on the constructed network of each model mouse thus obtained, phosphorylation signal transductions commonly changed in these model mice were identified using two different approaches described below.

(1) The First Approach

This is a selection approach based on a result of a simple comparison of phosphoproteome data from multiple model mice at the same time point (hypothesis free approach)

(2) The Second Approach

This is a selection approach based on an assumption that an abnormal phosphorylation signal is generated in some process of amyloid aggregation or before the aggregation (Aβ aggregation-linked approach).

Note that, in the first approach, the number of common nodes among the different models decreased with an increase in the number of AD models compared. To be more specific, the number of common nodes among the four types of AD models was only one (only MAP1B at the age of 1 month), while no node was included at the ages of 3 and 6 months. Thus, for further analyses, although unillustrated, 65 nodes were selected which were common between two types of the AD model mice one or more times. Among the 65 proteins, there were 51 proteins whose phosphorylations changed commonly in one combination of two types of the AD model mice at a certain single time point, while 14 proteins were phosphoproteins commonly changed at multiple time points and phosphoproteins commonly changed in multiple combinations of two types of the AD model mice (regarding the 14 proteins, see FIG. 1).

Meanwhile, in the second approach, an immunohistological analysis was performed on the four types of the AD model mice. Then, pathological differences were confirmed among these model mice. To be more specific, although unillustrated, in each of the 5×FAD mice and the APP mice, amyloid deposition started at the ages of 3 and 6 months. On the other hand, in the PS1 mice and the PS2 mice, no amyloid deposition was confirmed even at the age of 6 months.

Thus, based on such a result, it was presumed that the 5×ADD mice and the APP mice should share the pathological signal transduction at the time when the Aβ deposition started. Hence, significantly changed phosphoproteins were compared between the 1-month-old 5×FAD mice and the 3-month-old APP mice, or between the 3-month-old 5×FAD mice and the 6-month-old APP mice.

Then, from this comparison result, 11 nodes common in the 5×FAD mice and the APP mice were selected as phosphoproteins deduced to be linked to Aβ aggregation in the brain (regarding the 11 nodes (proteins), see FIG. 1). Surprisingly, as apparent from the result shown in FIG. 1, collating the results obtained by the different approaches showed that eight of the 11 proteins selected by the Aβ aggregation-linked approach were proteins also selected by the hypothesis free approach. On the other hand, more than a half of the 14 proteins whose phosphorylation states were observed to be commonly changed at multiple time points between two types of the AD model mice were also selected by the Aβ aggregation-linked approach.

Moreover, all of these phosphoproteins changed before the onset. To be more specific, although unillustrated, the four types of the AD model mice (PS1, PS2, APP, and 5×FAD) were subjected to the behavioral tests (Morris water maze test, rotarod test, open-field test, elevated plus maze test, light-dark box test, and fear-conditioning test), but any abnormal behavior was not detected at the age of 6 months.

As described above, in this phosphoproteomics analysis, the two independent approaches arrived at the similar conclusion, and 17 phosphoproteins were identified as factors involved in a pre-onset stage of Alzheimer's disease and composing a network (AD core network) which played a central role in the pathology.

Example 2

<AD Core Network Analysis in Tau Model Animals>

Although no conclusion has been drawn yet regarding the Alzheimer causative factor and onset mechanism, the most likely mechanism is such that when amyloid β molecules aggregate (amyloid pathology), the aggregation promotes tau phosphorylation and polymerization (tau pathology), consequently leading to nerve cell death and so forth (amyloid cascade hypothesis). Hence, regarding the transition from amyloid pathology to tau pathology presumed in this hypothesis, the 17 proteins selected from the amyloid-pathology-induced AD model mice were re-analyzed targeting tau-pathology-induced AD model mice.

Figure 34:
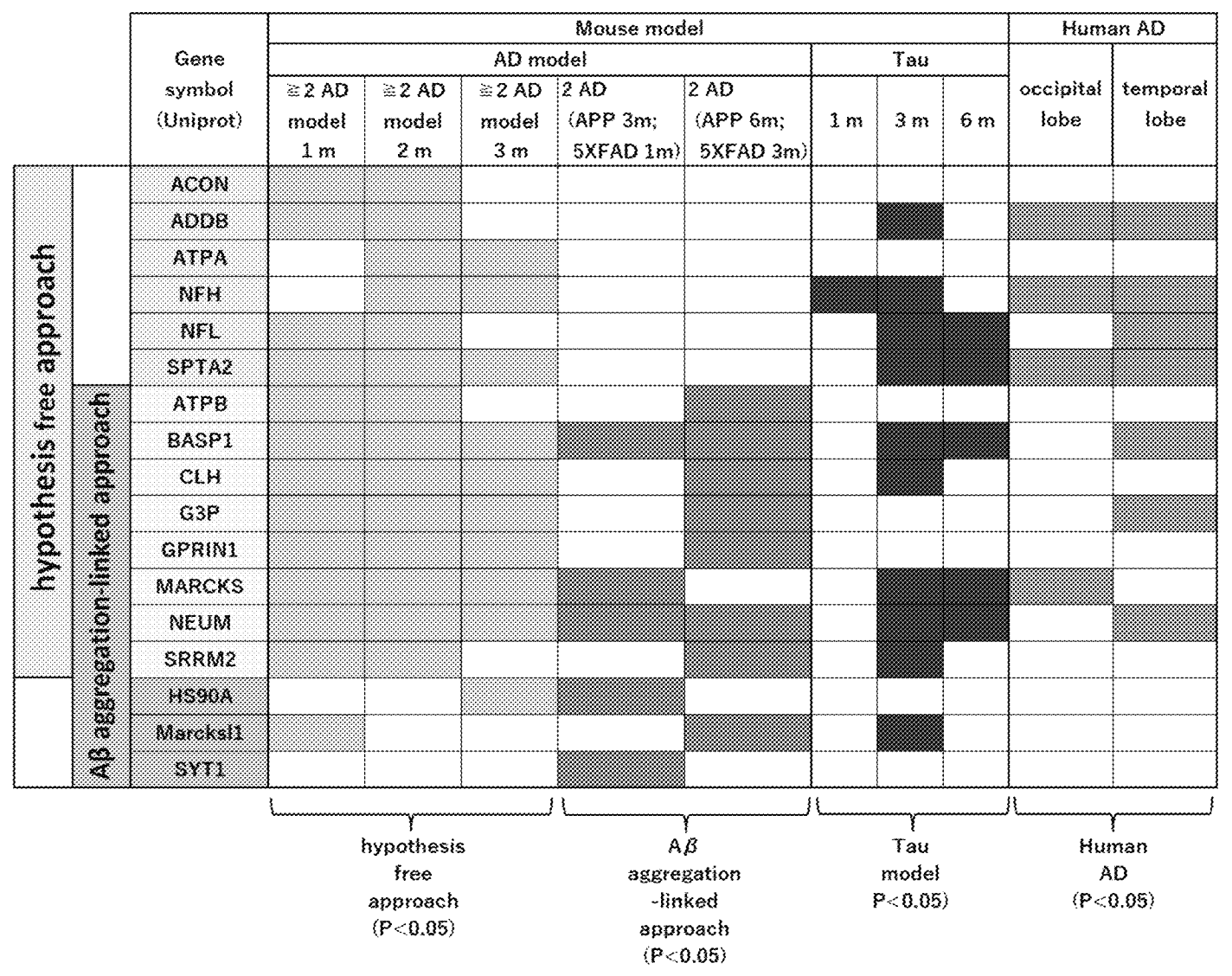

To be more specific, the 14 proteins also selected from the AD model mice by the hypothesis free approach were compared with phosphoproteins which changed in the Tau model mice. As a result, it was revealed as shown in FIG. 34 that 10 phosphoproteins (ADDB, NFH, NFL, SPTA2, BASP1, CLH, MARCS, NEUM, SRRM2, and Marcksl1) were commonly changed between the AD model mice and the Tau model mice.

Moreover, although unillustrated, tau was not included in the 17 proteins but included in the 65 proteins detected by the hypothesis free approach. To be more specific, the amount of the phosphorylated tau protein was enhanced commonly in severe AD model mice (5×FAD and APP) and tau model mice at the age of 1 month, supporting that the phosphorylation of the tau protein linked amyloid pathology to tau pathology.

Example 3

<AD Core Network Analysis in Human AD Patients>

Next, the 17 proteins selected from the result of the AD model mice described above were evaluated based on phosphoproteome data on the brains of human AD patients.

To be more specific, first, in order to obtain phosphoproteome data on the brains of human AD patients, mass spectrometry was performed using five brains of human AD patients as in the case of the mice. Note that the brain samples used in this analysis were isolated, frozen, and stored within 1 hour after death. The temporal lobe (temporal pole) and occipital lobe (occipital pole) samples of the brains were subjected to the analysis. Normally, these brain regions are remarkably affected regions in AD patients. In addition, these brain samples were analyzed after confirmed by a pathological examination that the samples were not contaminated with tissues exhibiting no AD pathology, such as lewy bodies and argyrophilic grains. Further, five brains derived from healthy subjects matching with the AD patients in age and five brains derived from patients having dementia with lewy bodies were also used as controls in the analysis.

Although unillustrated, based on phosphoproteins detected in all the human brains as a result of the analysis, a human default network was prepared. Note that, in this case, edges and accessory nodes were added to nodes based on not only the human PPI database but also mouse and rat PPI databases so as not to miss important molecules such as kinases and phosphatases in comparing the human and mouse networks in the subsequent analysis stage.

Then, each of the temporal lobe and occipital lobe was compared between the AD patient brains and the normal brains or DLB patient brains, and changed phosphoproteins were selected as "human (AD)-(normal) nodes" or "human (AD)-(DLB) nodes". It was noteworthy that all the disease-specific nodes in the "human (AD)-(DLB) nodes" were also detected in the "human (AD)-(normal) node" network. Subsequently, networks were prepared based on the "human (AD)-(normal) nodes" in the temporal lobe and occipital lobe, and compared with the above-described 17 proteins based on the mouse phosphoproteome. The result revealed as shown in FIG. 34 that ADDB, NFH, NFL, SPTA2, BASP1, G3P, MARCKS, and NEUM among the 17 proteins composing the AD core network were changed commonly in the human AD patients.

Moreover, these nine phosphoproteins commonly changed also in the human AD patients were identified as the phosphoproteins having been changed in the Tau model mice, except for G3P.

Thus, the above analysis results of the Tau model animals and the human AD patients verified that the 17 proteins or at least most of them were involved in a pre-onset stage of Alzheimer's disease and were components of a network which played a central role in the pathology.

Example 4

<Functional Analysis on AD Core Network>

Figure 2:
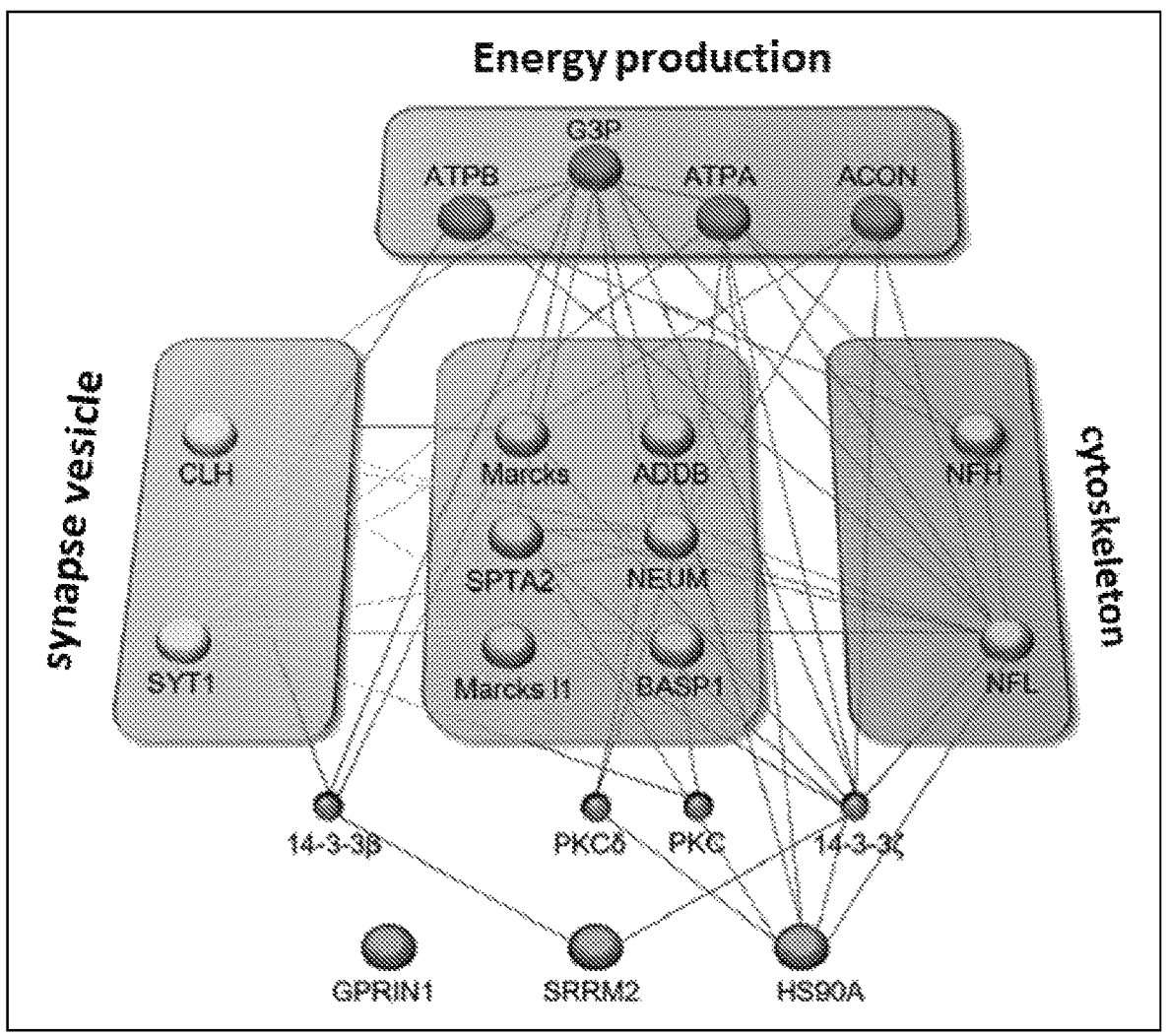
FIG. 2 is a schematic diagram showing a network constructed of the 17 proteins shown in FIG. 1. Note that the 17 proteins are proteins (AD core proteins) revealed to have phosphorylation levels enhanced in the brains affected with Alzheimer's disease identified in the present invention and to play central roles in a pathology of the disease. Moreover, in the figure, lines (edges) connecting the proteins (nodes) represent interactions therebetween.

Based on the integrated human-mouse PPI database described above, the AD core network composed of the 17 proteins was prepared. FIG. 2 shows the obtained result.

As apparent from the result shown in FIG. 2, surprisingly, 12 proteins in the 17 proteins were directly linked, and three proteins (SRRM2, BASP1, and ADDB) were linked via one independent protein. Note that, in the PPI database, Marcksl1 was a protein not directly linked to the other 16 proteins but exhibiting a high homology with MARCKS. This revealed that at least 15 proteins formed a single functional network.

Further surprisingly, their functions were mainly directly related to synapse functions such as spine formation, vesicle recycling, and energy production.

SPTA2 (brain a spectrin) is a protein cross-liked to actin and expressed at a high level in the brain (see Leto, T. L. et al., Mol. Cell. Biol., 1988, Vol. 8, pp. 1 to 9). It is known that SPTA2 interacts with SHANK at the postsynaptic density (see Bockers, T. M. et al., J. Biol. Chem., 2001, Vol. 276, pp. 40104 to 40112), and interacts with ADDB/aducin-b, one of the 17 proteins identified this time, forming spectrin/adducin/actin complexes (see Li, X. et al., J. Biol. Chem., 1996, Vol. 271, pp. 15695 to 15702). Moreover, it has also been revealed that these proteins are substrates of protein kinase C (PKC), and after the phosphorylation of these proteins, the complex becomes unstable, decreasing the membrane stability, too.

It is known that ADDB contains a MARCKS-related domain, and that the phosphorylation by PKC controls the postsynaptic localization and inhibits actin/spectrin complex formation as described above (see Matsuoka, Y. et al., J. Cell Biol., 1998, Vol. 142, pp. 485 to 497). Additionally, this system has been shown to control synapse production and removal, although the result was at the neuromuscular junction (NMJ) in *Drosophila* (see Pielage, J. et al., Neuron, 2011, Vol. 69, pp. 1114 to 1131).

MARCKS, BASP1, and NEUM are known to be greatly involved in signals originating from lipid rafts. Additionally, MARCKS is a PKC-specific substrate and normally localized at the cell membrane. However, it is known that after phosphorylated or bound to calmodulin, MARCKS is released from the cell membrane and transferred to the cytoplasm, inhibiting F-actin cross-linking (see Hartwig, J. H. et al., Nature, 1992, Vol. 356, pp. 618 to 622). Further, various morphological and functional abnormalities have been observed in mouse brains having mutant MARCKS (see Stumpo, D. J. et al., Proc. Natl. Acad. Sci. U.S.A, 1995, Vol. 92, pp. 944 to 948).

MRP/Marcksl1 is a member of the MARCKS family, and involved in PKC signal transduction. Additionally, it is known that Marcksl1 is phosphorylated by JNK and controls the actin stability and the filopodium formation of neurons (see Bjorkblom, B. et al., Mol. Cell. Biol., 2012, Vol. 32, pp. 3513 to 3526).

NEUM/neuromodulin/GAP43 is an important component of growth cone/axon presynaptic terminals and is known as a main substrate of PKC (see Benowitz, L. I. et al., Trends Neurosci., 1997, Vol. 20, pp. 84 to 91). Additionally, it is known that NEUM interacts with various molecules. For example, there is a report that NEUM interacts with PIP2 and palmitate, or cytoskeletal proteins such as actin, spectrin, synaptophysin, and tau. As in the case of MARCKS and SPTA2, it has been shown that NEUM is also controlled by calmodulin and moves between the membrane and cytoplasm (see Gamby, C. et al., J. Biol. Chem., 1996, Vol. 271, pp. 26698 to 26705). As described above, NEUM is an adaptor protein which controls presynaptic terminal functions via cytoskeletal regulation, and is suggested to be involved in memory and LTP formation (see Routtenberg, A. et al., Proc. Natl. Acad. Sci. U.S.A, 2000, Vol. 97, pp. 7657 to 7662).

BASP1/NAP-22/CAP23 is myristoylated protein having a PEST motif, and is abundant in axonal terminals (see Mosevitsky, M. I. et al., Biochimie, 1997, Vol. 79, pp. 373 to 384). Although the function has not been sufficiently elucidated, BASP1/NAP-22/CAP23 exists at the inner surface of a lipid raft in the cell membrane. In addition, BASP, MARCKS, and NEUM seem to regulate PI (4, 5) P2 by a common mechanism. Further, it is suggested that the phosphorylation-dependent interaction between calmodulin and BASP, MARCKS, or NEUM promotes actin network formation (see Laux, T. et al., J. Cell Biol., 2000, Vol. 149, pp. 1455 to 1472).

As described above, it is suggested that the proteins composing the AD core network form a network which controls presynaptic and postsynaptoc morphologies.

Meanwhile, phosphoproteomic changes of SYT1/synaptotagmin 1 and GPRIN1/G protein regulated inducer of neurite outgrowth 1 were not detected in the brains of both the Tau model mice and the human AD patients. Nevertheless, these proteins might also be involved in a pre-onset stage of AD. Particularly, SYT1/synaptotagmin 1 is important because it controls vesicle recycling at synaptic terminals. Note that SYT1 is known to form a complex at synaptic terminals with a vesicle cargo molecule CLH/clathrin heavy chain selected by both of the hypothesis free approach and the Aβ aggregation-linked approach (see Schwarz, T. L., Proc. Natl. Acad. Sci. U.S.A, 2004, Vol. 101, pp. 16401 to 16402). Additionally, GPRIN1 is a Gαo effector enriched in the growth cone membrane fraction which induces neurite outgrowth (see Chen, L. T., J. Biol. Chem., 1999, Vol. 274, pp. 26931 to 26938). However, the detailed functions have not been elucidated yet.

Further, interestingly, molecules involved in energy production were also selected. To be more specific, ATPA and ATPB are mitochondrial ATP synthase subunits A and B, respectively. ACON is mitochondrial aconitase 2 which catalyzes citrate isomerization in TCA cycle. Moreover, G3P/GAPDH/glyceraldehyde-3-phosphate dehydrogenase is an important enzyme in glycolysis, also plays a nuclear function through the nitrosylase activity, and affects microtubule assembly by the same mechanism. Thus, the enzyme is also related to cytoskeleton.

SRRM2 is involved in splicing together with SRm160 (see Blencowe, B. J., Genes Dev., 1998, Vol. 12, pp. 996 to 1009), and is functionally different from the other core network proteins.

HS90A/HSP90 is a chaperon molecule involved in quality control and folding of various proteins. Because of the general roles, HS90A/HSP90 is linked to various proteins in the core network.

As described above, it was revealed that the phosphoproteomic changes in the pre-onset stage of Alzheimer's disease were selectively focused on two or three networks which controlled synapse function and energy metabolism.

<Changes in Phosphoproteins Due to Aging in AD Model Animals>

Further analyzed was how chronological changes in phosphoproteins (changes in phosphoproteins by pathological aging) in AD model mice were related to those (chronological changes in phosphoproteins in the background mice) in normal aging (physiological aging). Note that proteins from which data were not obtained with a high confidence at any time point of the 5×FAD mice were excluded from this analysis.

In this analysis, three sets of new samples including the 5×FAD mice and the background mice at the ages of various time points from 1 to 12 months were analyzed by the mass spectrometry. Moreover, based on values of the 1-month-old background mice obtained regarding the 17 phosphoproteins, values of the 5×FAD mice and the background mice at the ages of each month were corrected and plotted on a graph to analyze the chronological changes in these phosphoproteins.

As a result, although unillustrated, the patterns of changes in most of the phosphoproteins composing the AD core network were qualitatively similar between the physiological aging and the ageing due to the pathological aging. However, the patterns were quantitatively different. It was revealed that each phosphoprotein had a time point when a difference in the expression amount thereof was remarkably large between the 5×FAD mice and the background mice.

For example, regarding MARCKS, Marcksl1, and SRRM2, amounts of these phosphoproteins in the 1-month-old 5×FAD mice were remarkably large in comparison with those of the background mice. Note that the difference was diminished over time. Moreover, regarding SPTA2, G3P, ADDS, SYT1, BASP1, HSP90A, and NEUM, amounts of these phosphoproteins in the 3-month-old 5×FAD mice were remarkably large in comparison with those of the background mice. Further, regarding NFH, NFL, CLH, and GPRIN1, amounts of these phosphoproteins in the 12-month-old 5×FAD mice were remarkably different from those of the background mice.

Figure 3:
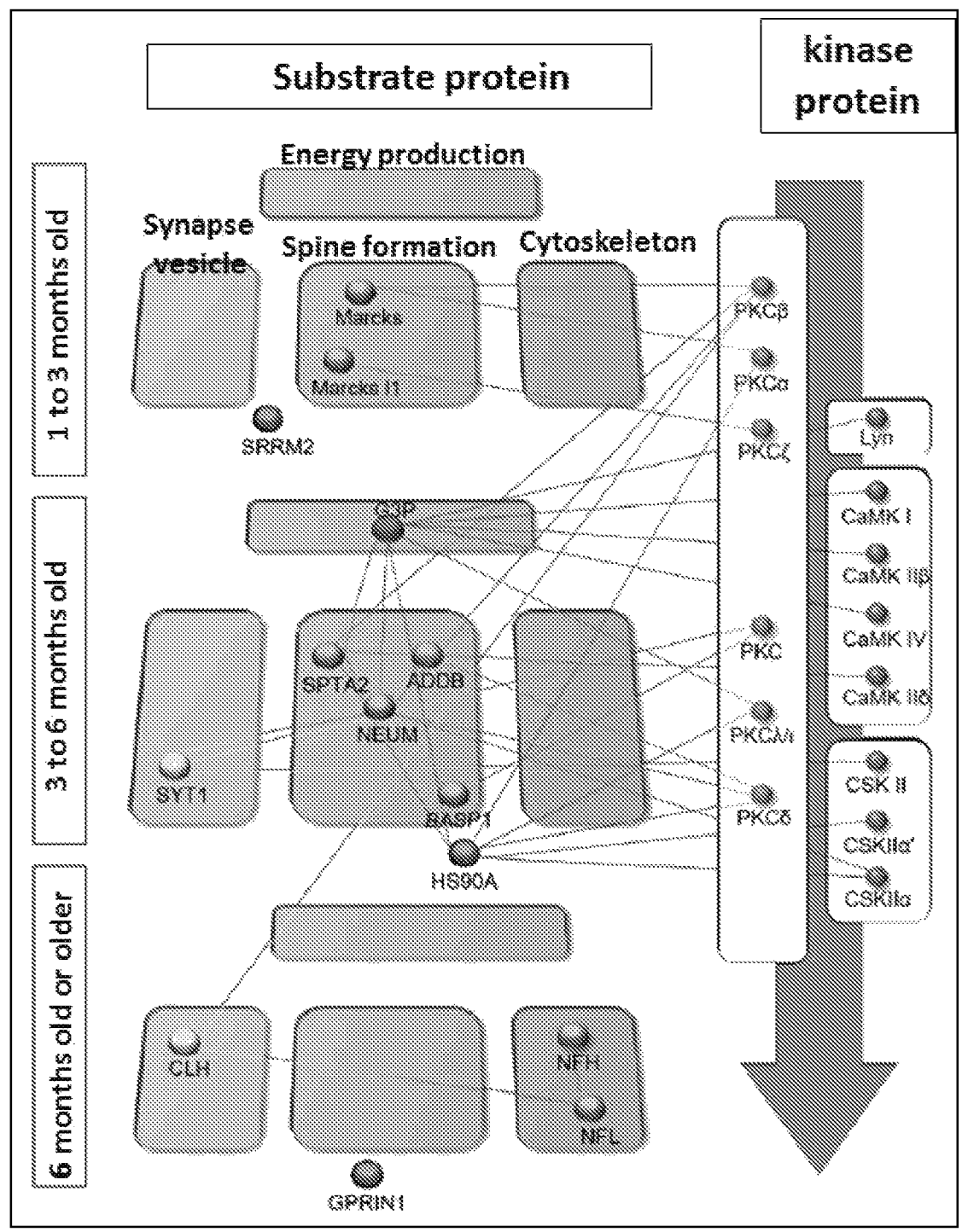
FIG. 3 is a schematic diagram showing chronological changes in phosphorylations of kinases and substrate proteins thereof in a pre-onset stage of Alzheimer's disease. To be more specific, it is shown that: at the ages of 1 to 3 months, the phosphorylations of MARCKS, MARCKSL1, and SRRM2 in AD model mice (5×FAD mice) are remarkably high in comparison with those of the wild type; at the ages of 3 to 6 months, the phosphorylations of G3P, SYT1, SPTA2, ADDB, NEUM, BASP1, and HSP90A in the AD model mice are remarkably high in comparison with those of the wild type; and at the age of 6 months or later, the phosphorylations of CLH, NFH, NFL, and GPRIN1 in the AD model mice are remarkably high in comparison with those of the wild type. Note that, in the 12-month-old AD model mice, no onset (such as abnormal behavior) is observed. Moreover, in the figure, lines (edges) connecting the proteins (nodes) represent interactions therebetween. In the figure, regarding "PKC", see J Biol Chem., 1994, Vol. 269, No. 30, pp. 19462 to 19465 and J Neurochem., 1999, Vol. 73, Iss. 3, pp. 921 to 932. In addition, regarding "CSKII", see J Biol Chem., 1993, Vol. 268, No. 9, pp. 6816 to 6822.

Furthermore, based on the result of analyzing the above chronological changes in the phosphoproteins, the core protein network was reconstructed. FIG. 3 shows the obtained result.

As described above, the phosphorylations of MARCKS and its homolog Marcksl1 changed at the initial phase. Moreover, it was revealed as shown in FIG. 3 that the changes of these were followed by those of the other core phosphoproteins belonging to the same functional domain or related functional domains.

Example 5

<Search for Kinases/Phosphatases Involved in Change in AD Core Network>

As shown in FIG. 3, the chronological changes in the phosphorylations of the proteins composing the AD core network in the pre-onset stage of Alzheimer's disease can be categorized into three patterns: one having a peak at the initial phase, one having a peak at the mid phase, and one having a peak at the late phase. Moreover, in view of these categories, it is presumed that the phosphorylations of the proteins composing the AD core network are controlled by particular kinases and the like in a time-specific manner.

Hence, in order to search for kinases and the like involved in this AD core network control, first, kinases and phosphatases were selected among the proteins directly linked to the proteins composing the AD core network. Then, among these kinases and phosphatases, PKC was considered as the most important enzyme involved in the change in the AD core network from the viewpoint that it could phosphorylate the largest number of the core protein. Note that, as having been already revealed from various reports in the past regarding AD pathology, MAPK and MAPKKK were identified after PKC.

Moreover, as the second group following these three kinases, identified were casein kinase (CSKII), receptor-interacting protein serine/threonine kinase 1/3 (RIP1/3), cyclin-dependent kinase 5/6 (CDK5/6), and protein kinase C-like protein 1 (PKN1). Further, as the third group, identified were Ca2+/calmodulin-dependent kinase (CaMKI/II), protein kinase D (PKD), and the like. Moreover, Lck/Yes-related novel protein tyrosine kinase (Lyn) and other 20 kinases were identified as candidates to control the core network, although these were linked to just one core protein.

FIG. 3 shows the enzyme-substrate relation obtained by comparing the result of analyzing the above kinases linked to the core phosphoproteins with the result of the chronological changes in the core phosphoproteins in the 5×FAD mice described above.

As apparent from the result shown in FIG. 3, the initial phase (at the age of 1 month), the mid phase (at the age of 3 months), and the late phase (at the age of 6 months) patterns of the core phosphoproteins were observed to have correlations with PKC, Lyn, CamK, and CASK.

It seemed that the PKC family among these activated various kinases earliest, and that the activation continued until the late phase. To be more specific, it was revealed that first the PKC family phosphorylated MARCKS and Marcksl1, and next the kinase family phosphorylated G3P, NEUM, BASP1, and SPTA2.

Further, in order to identify target sequences of the kinases which controlled 18 proteins composing the AD core network, the data on the peptide phosphorylations obtained from the mass spectrometry were examined again, and a phosphorylation level at one site of each protein was individually analyzed. To be more specific, identified were polypeptides containing one phosphorylation site whose amount changed in comparison with the wild type at $P<0.05$ at one or more time points in at least one model among the five types of transgenic mice (the four types of AD model mice and one type of Tau model mice).

As a result, although unillustrated, significant changes in the phosphorylation levels were observed in ADDB at serine at position 60, serine at position 62, serine at position 532, serine at position 594, serine at position 602, serine at position 618, serine at position 692, and serine at position 700. Significant changes in the phosphorylation levels were observed in NFH at serine at position 500, serine at position 535, serine at position 583, serine at position 673, serine at position 721, serine at position 763, serine at position 795, serine at position 834, threonine at position 839, serine at position 867, and serine at position 888. Significant changes in the phosphorylation levels were observed in NFL at serine at position 473, serine at position 523, and serine at position 532. Significant changes in the phosphorylation levels were observed in SPTA2 at serine at position 1031 and serine at position 1217. Significant changes in the phosphorylation levels were observed in ATPB at threonine at position 262 and threonine at position 453. Significant changes in the phosphorylation levels were observed in BASP1 at threonine at position 31, threonine at position 36, serine at position 92, serine at position 131, serine at position 192, and serine at position 218. Significant changes in the phosphorylation levels were observed in G3P at threonine at position 182 and threonine at position 209. Significant changes in the phosphorylation levels were observed in GPRIN1 at serine at position 182, serine at position 219, serine at position 495, serine at position 576, serine at position 691, serine at position 693, serine at position 714, serine at position 764, serine at position 771, serine at position 816, and threonine at position 795. Significant changes in the phosphorylation levels were observed in MARCKS at serine at position 26, serine at position 27, serine at position 29, serine at position 113, serine at position 122, serine at position 124, serine at position 125, serine at position 127, serine at position 128, serine at position 138, serine at position 140, serine at position 141, threonine at position 143, serine at position 163, serine at position 171, and serine at position 299. Significant changes in the phosphorylation levels were observed in NEUM at serine at position 86, threonine at position 89, serine at position 96, serine at position 142, threonine at position 172, and serine at position 193. Significant changes in the phosphorylation levels were observed in SRRM2 at serine at position 1067, serine at position 1278, serine at position 1305, serine at position 1339, serine at position 1359, serine at position 1360, serine at position 2351, serine at position 2084, serine at position 2404, serine at position 2535, threonine at position 1448, and threonine at position 2350. Significant changes in the phosphorylation levels were observed in Marcksl1 at serine at position 22, threonine at position 85, serine at position 104, threonine at position 148, serine at position 189, serine at position 151, and serine at position 185. Significant changes in the phosphorylation levels were observed in HS90A at serine at position 231 and serine at position 263. Significant changes in the phosphorylation levels were observed in SYT1 at threonine at position 125 and threonine at position 128.

<Involvement of Kinases in Alzheimer's Disease Pathology>

The significance of the AD core network, which was constructed based on the above-described analysis result, in the pathology of Alzheimer's disease was verified using in vivo and in vitro experimental systems.

The functions of the core factors revealed by the phosphoproteome analysis suggested that specific phosphorylation signals linking presynaptic cytoskeleton to postsynaptoc cytoskeleton were perturbed at the earliest stage before the onset of Alzheimer's disease.

Particularly, it has been suggested that the cytoskeleton network composed of actin binding proteins such as actin and spectrin mainly controls dendritic spine formation (see Matus, A., Science, 2000, Vol. 290, pp. 754 to 758, Tada, T. et al., Curr. Opin. Neurobiol., 2006, Vol. 16, pp. 95 to 101). Hence, it was presumed that the link from MARCKS to actin polymerization and the link from SPTA2 to actin-spectrin cross-linking became abnormal at the initial phase of Alzheimer's disease, and that these cytoskeleton network activations affected the dendritic spine dynamics, and were consequently involved in the pathology of Alzheimer's disease.

Thus, the dendritic spine dynamics were analyzed with a two-photon microscope targeting the 5xFAD mice (12 weeks old) before the onset of Alzheimer's disease. FIGS. 4 to 9 show the obtained result.

Figure 4:
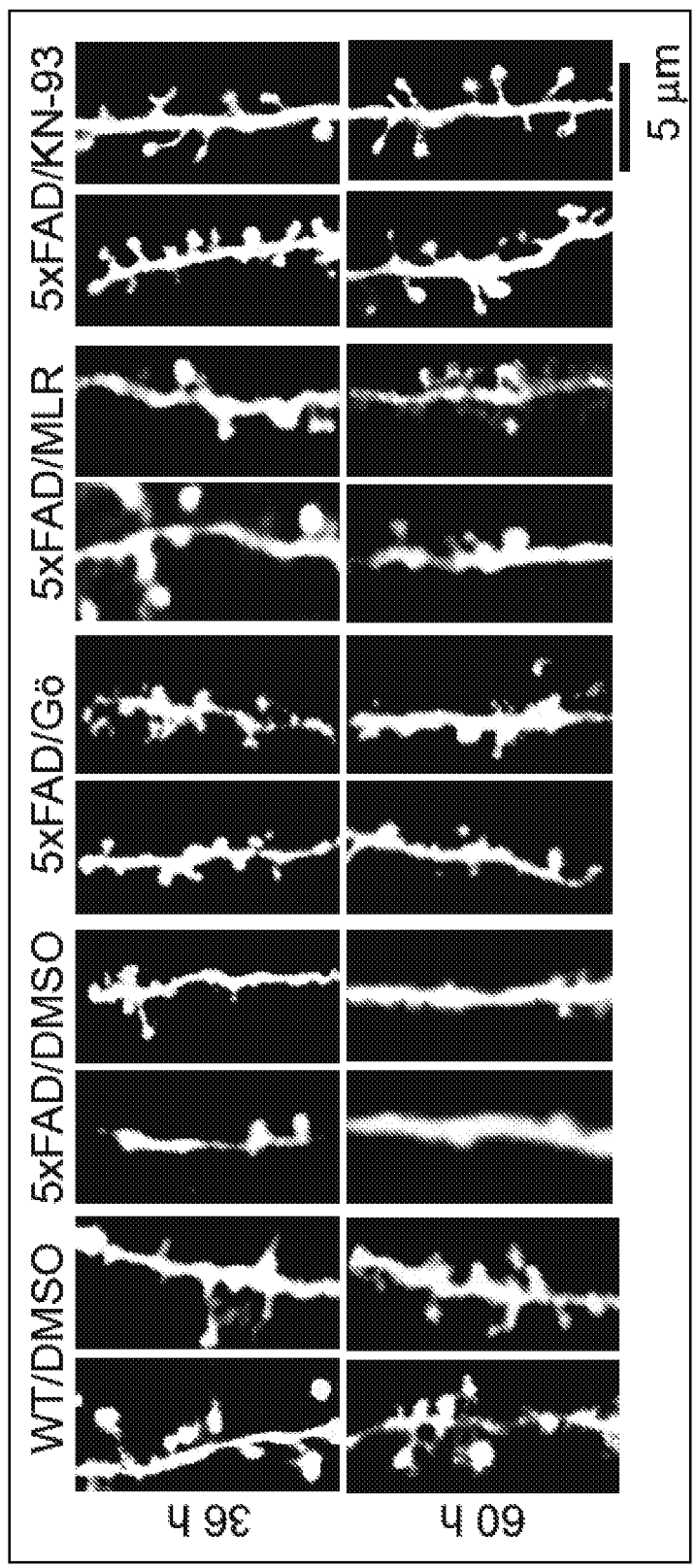
FIG. 4 shows photograph for illustrating the result of administering a kinase inhibitor (Go6976 or KN-93) or a Lyn kinase activator (MLR1023) into 5×FAD mice (12 weeks old), and observing dendritic spines/dendrites in layer 1 of the retrosplenial cortex 36 hours and 60 hours thereafter. Note that the observation results of administering DMSO (solvent alone) into 5×FAD mice and background mice thereof (36/SJL (WT)) as controls are also shown together.
Figure 5:
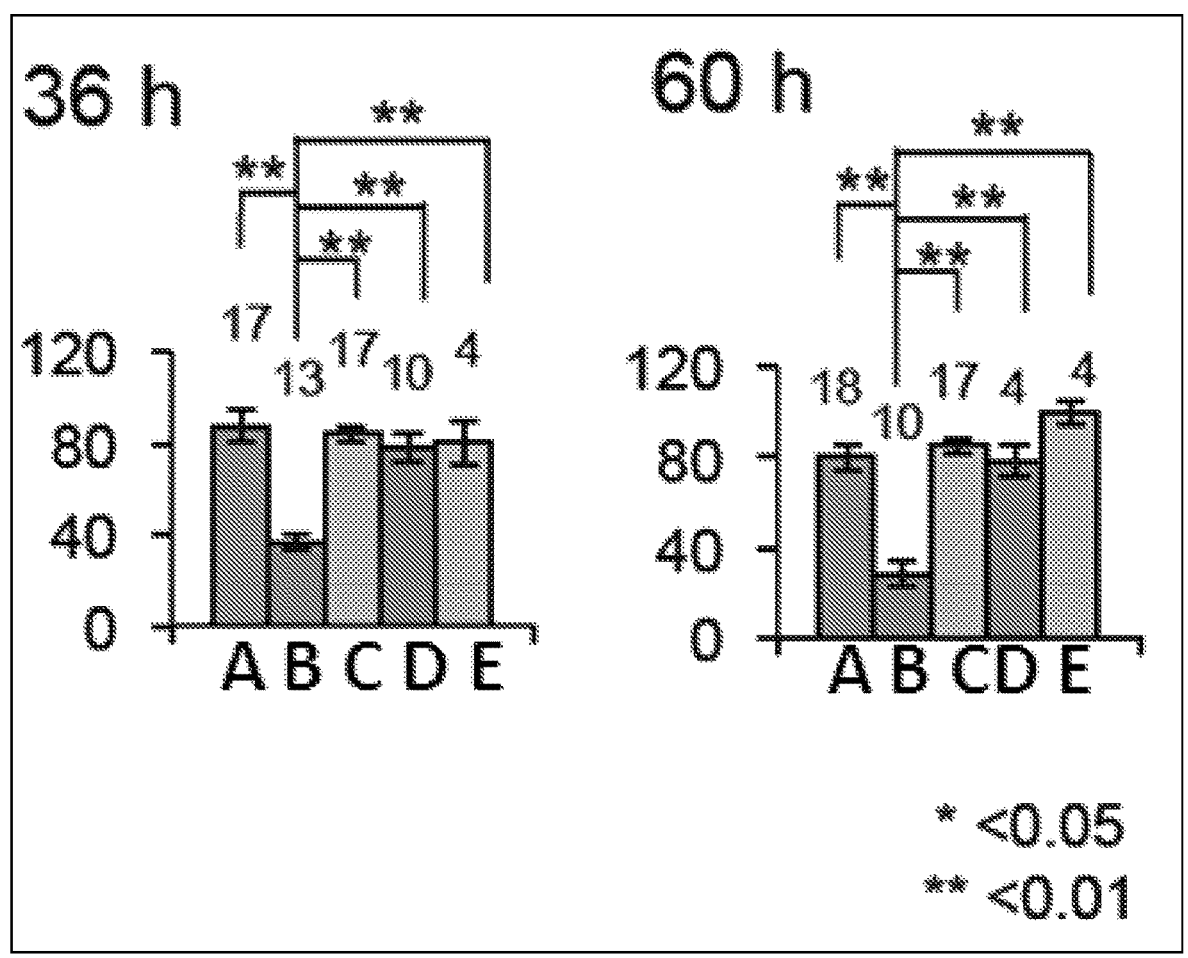
FIG. 5 shows graphs for illustrating the result of quantitatively analyzing the dendritic spine densities in the 5×FAD mice 36 hours and 60 hours after Go6976, KN-93 or MLR1023 was administered. To be more specific, the graphs show that clearly the number of protrusions was decreased in the 5×FAD mice, while the treatment with Go6976, KN-93, or MLR1023 recovered the decrease of spines in the 5×FAD mice. In the figure, A shows the result of administering DMSO (solvent alone) into the background (WT) mice, B shows the result of administering DMSO into the 5×FAD mice, C shows the result of administering Go6976 into the 5×FAD mice, D shows the result of administering MLR1023 into the 5×FAD mice, and E shows the result of administering KN-93 into the 5×FAD mice. Moreover, each bar graph shows the average value +/−the standard error, and is provided with numerical values indicating the number of samples in each administration group. One and two asterisks respectively indicate p<0.05 and p<0.01 Student's independent t-test (regarding the representations in the figure, the same shall apply to FIGS. 6, 8, 9, and 11).
Figure 6:
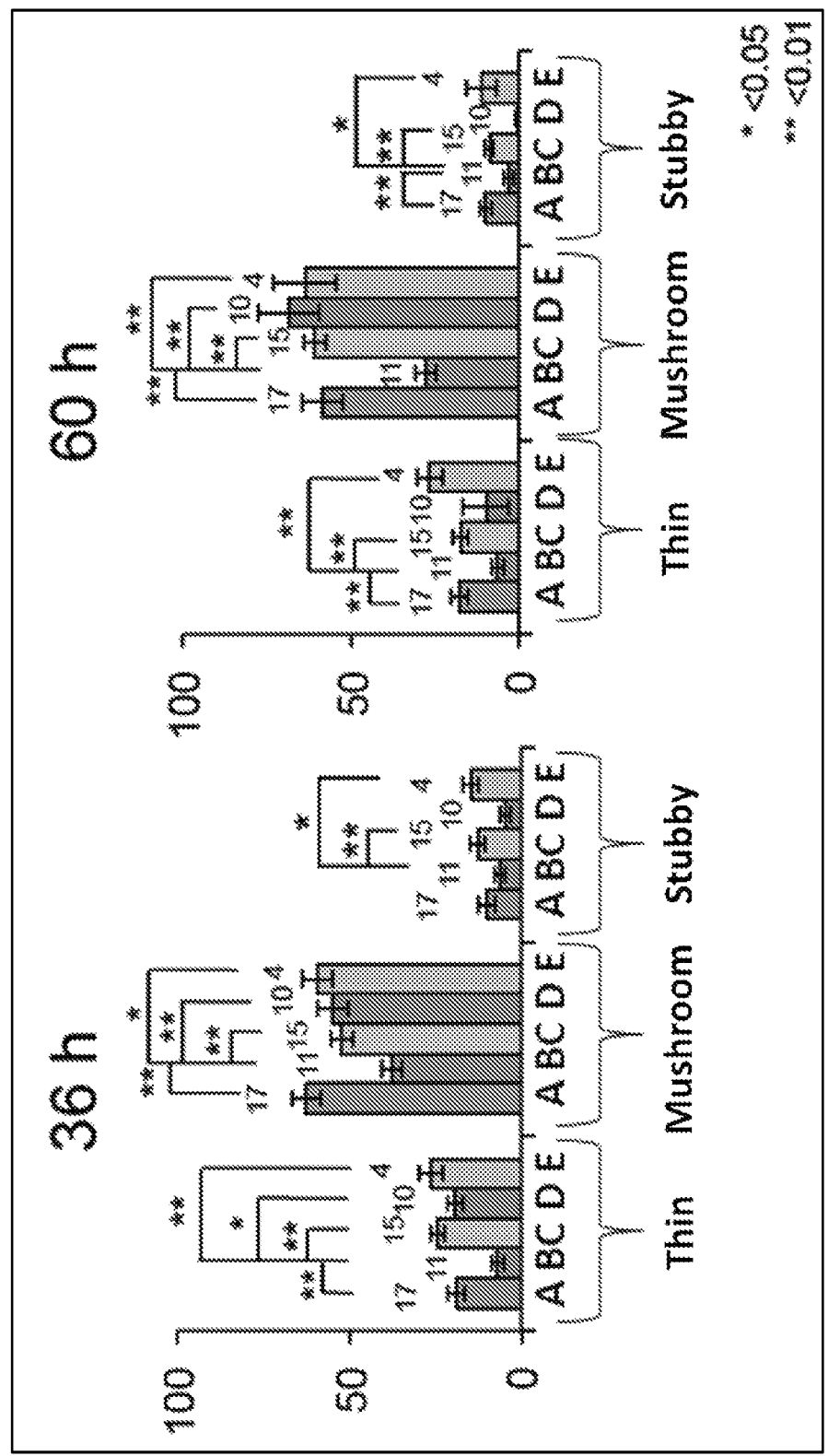
FIG. 6 shows graphs for illustrating the result of quantitatively analyzing the spine type 36 hours and 60 hours after Go6976, KN-93, or MLR1023 was administered. To be more specific, the graphs show that, regardless of the morphological type, the spine densities were decreased in the 5×FAD mice, and that the decreases were recovered by the treatment with Go6976, KN-93, or MLR1023.

Living cortical neurons of layer 1 of the 12-week-old 5xFAD mice were observed with a two-photon microscope. The result revealed as shown in FIGS. 4 and 5 that the dendritic spine densities of the cortical neurons were remarkably decreased. Moreover, decreases in the number of spines per dendritic shaft length were observed in all the spine types (thin, mushroom, and stubby) (see FIG. 6). Further, regarding absolute numbers of dendritic spines per 100 μm, all of the formed spines, eliminated spines, and stably remaining spines were decreased (see FIGS. 7 to 9). Moreover, regarding the percentages of three types of spine dynamics in the 5xFAD mice, the formed spines were decreased. On the other hand, no remarkable change was observed in the eliminated spines and the stably remaining spines (see FIG. 9). In sum, it was revealed that the spine format on in process was affected in the pathology of the 5xFAD mice. Note that these results basically agree with the findings in the past regarding AD model mice (see Palop, J. J. et al., Neurosci., 2010, Vol. 13, pp. 812 to 818, Wei, W. et al., Nat. Neurosci., 2010, Vol. 13, pp. 190 to 196, Wu, H. Y. et al., J. Neurosci., 2010, Vol. 30, pp. 2636 to 2649). Hence, next, kinases were analyzed which were suggested to affect the AD core network from the initial phase to the mid phase of the pre-onset stage of Alzheimer's disease. More concretely, the effect of the kinases on the synaptic pathology in the 5xFAD mice was analyzed by administering inhibitors and so forth against these kinases into the subarachnoid spaces of the mice. FIGS. 4 to 9 show the obtained result.

Administering a PKC inhibitor (Go6976) ameliorated spine abnormality in the 5xFAD mice and increased the total spine density (see FIGS. 4 and 5). Moreover, the numbers of spines of thin, mushroom, and stubby types were also increased (see FIG. 6). Further, regarding the spine dynamics, the Go6976 treatment enhanced the spine formation and stability (see FIGS. 7 to 9).

Moreover, it was revealed that the treatment with a CamKII inhibitor (KN-93) also had a therapeutic effect on the spine formation and stability. Further, it was also revealed that the numbers of all the types of dendritic spines that had been decreased in the 5xFAD mice were recovered by the treatment (see FIGS. 7 to 9).

Figure 7:
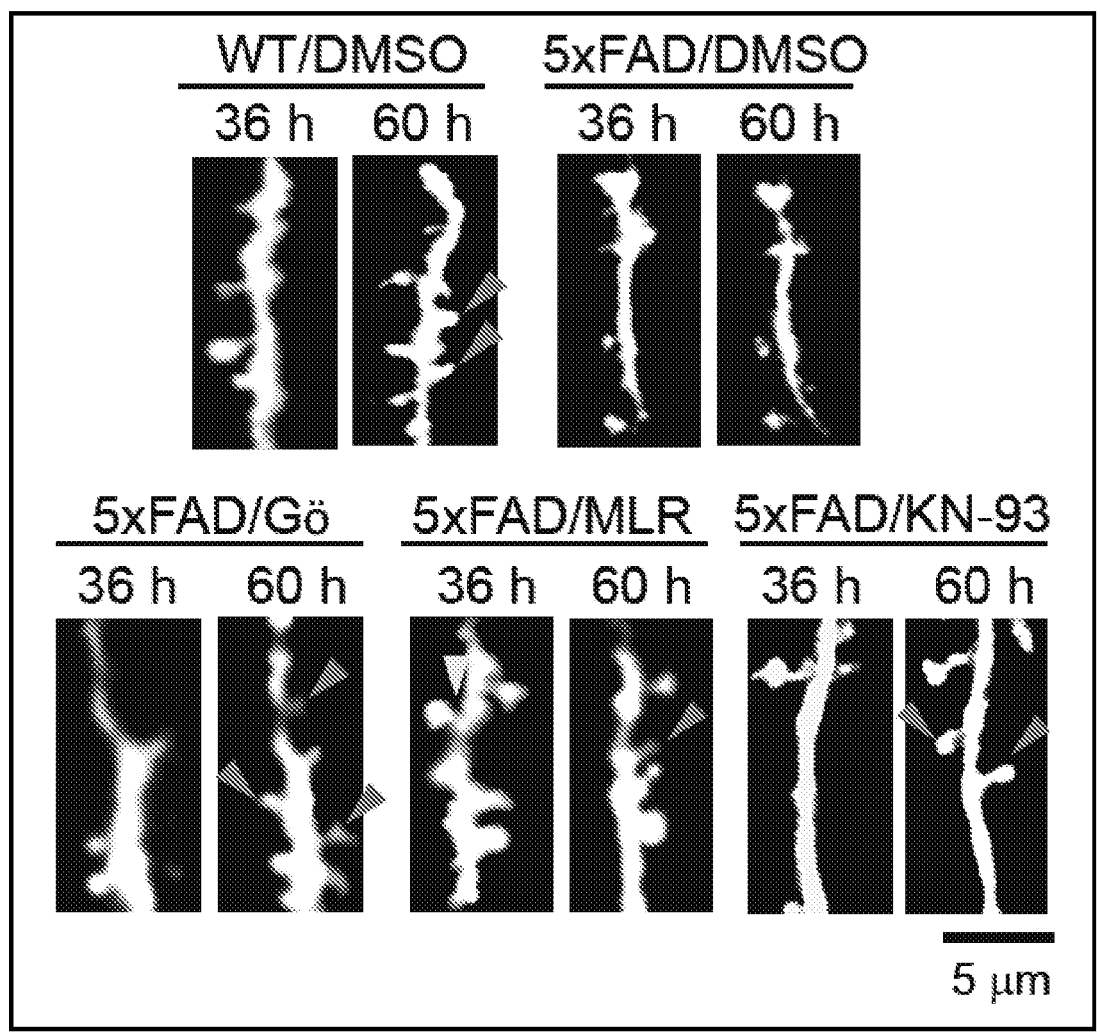
FIG. 7 shows photographs illustrating the spine formation and elimination in the 5×FAD mice 36 hours and 60 hours after Go6976, KN-93, or MLR1023 was administered. The arrow in the figure after 36 hours (36 h) indicates the spine to be eliminated. The arrows in the figure after 60 hours (60 h) indicate formed spines. Note that the observation results of administering DMSO (solvent alone) into the 5×FAD mice and the background mice (B6/SJL (WT)) as the controls are also shown together.
Figure 8:
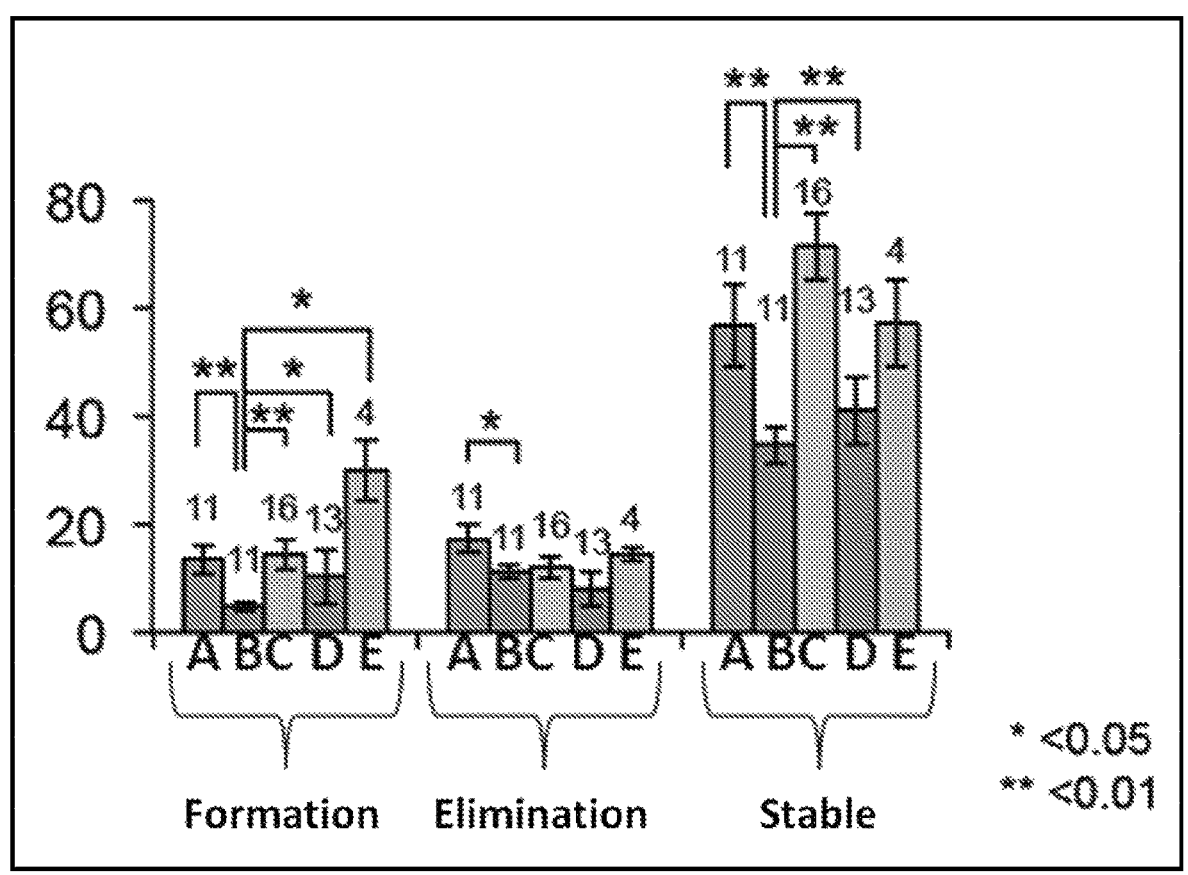
FIG. 8 shows graphs for illustrating the result of quantitatively analyzing the dendritic spine dynamics in the 5×FAD mice 36 hours and 60 hours after Go6976, KN-93, or MLR1023 was administered. In the figure, the vertical axis represents the number of formed spines, eliminated spines, or stably remaining spines per 100 μm of the dendritic shaft.
Figure 9:
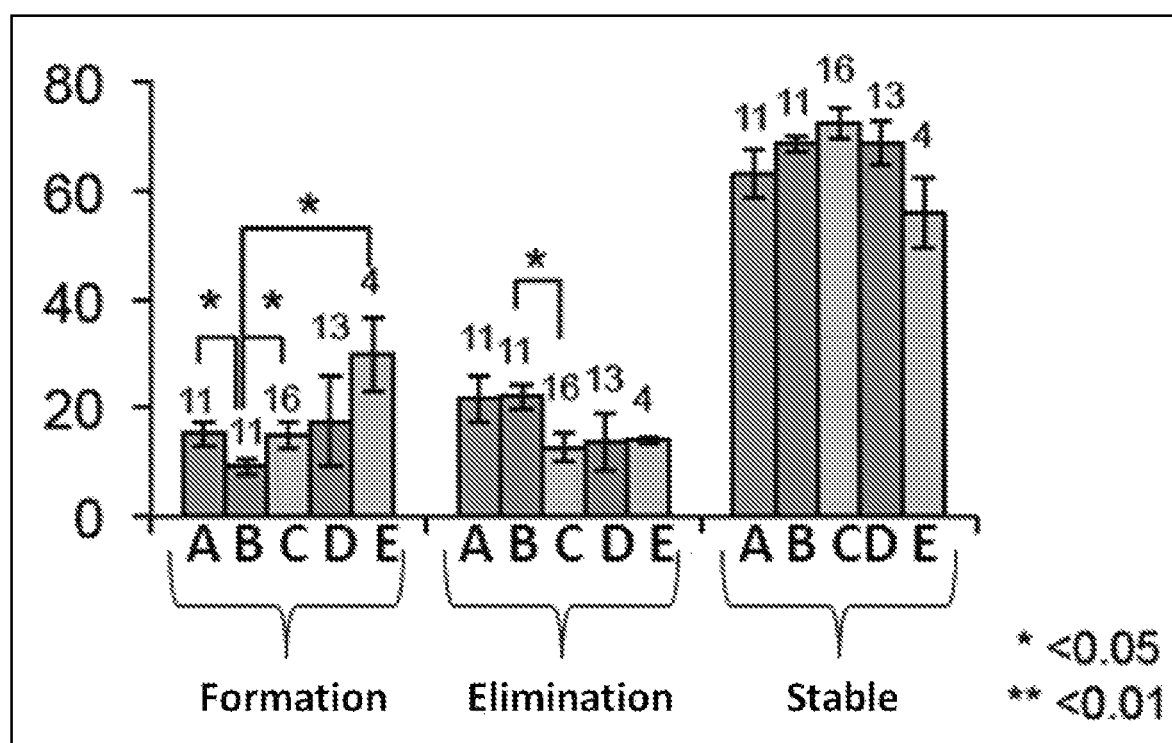
FIG. 9 shows graphs for illustrating the result of quantitatively analyzing the dendritic spine dynamics in the 5×FAD mice 36 hours and 60 hours after Go6976, KN-93, or MLR1023 was administered. In the figure, the vertical axis represents the relative percentage of formed spines, eliminated spines, or stably remaining spines.

Further, it was revealed that the treatment with a Lyn kinase activator (MLR1023) also had a therapeutic effect on the spine formation and stability as in the case of the treatment with the PKC inhibitor or CamKII inhibitor (see FIGS. 7 to 9). Note that MLR1023 found to be effective this time is also known as an insulin receptor potentiating agent. Hence, the therapeutic effect this time is presumably also an effect of alleviating the insulin resistance, which is observed in the brains of Alzheimer's disease patient (see Craft, S., Nat. Rev. Neurol., 2012, Vol. 8, pp. 360 to 362).

Figure 10:
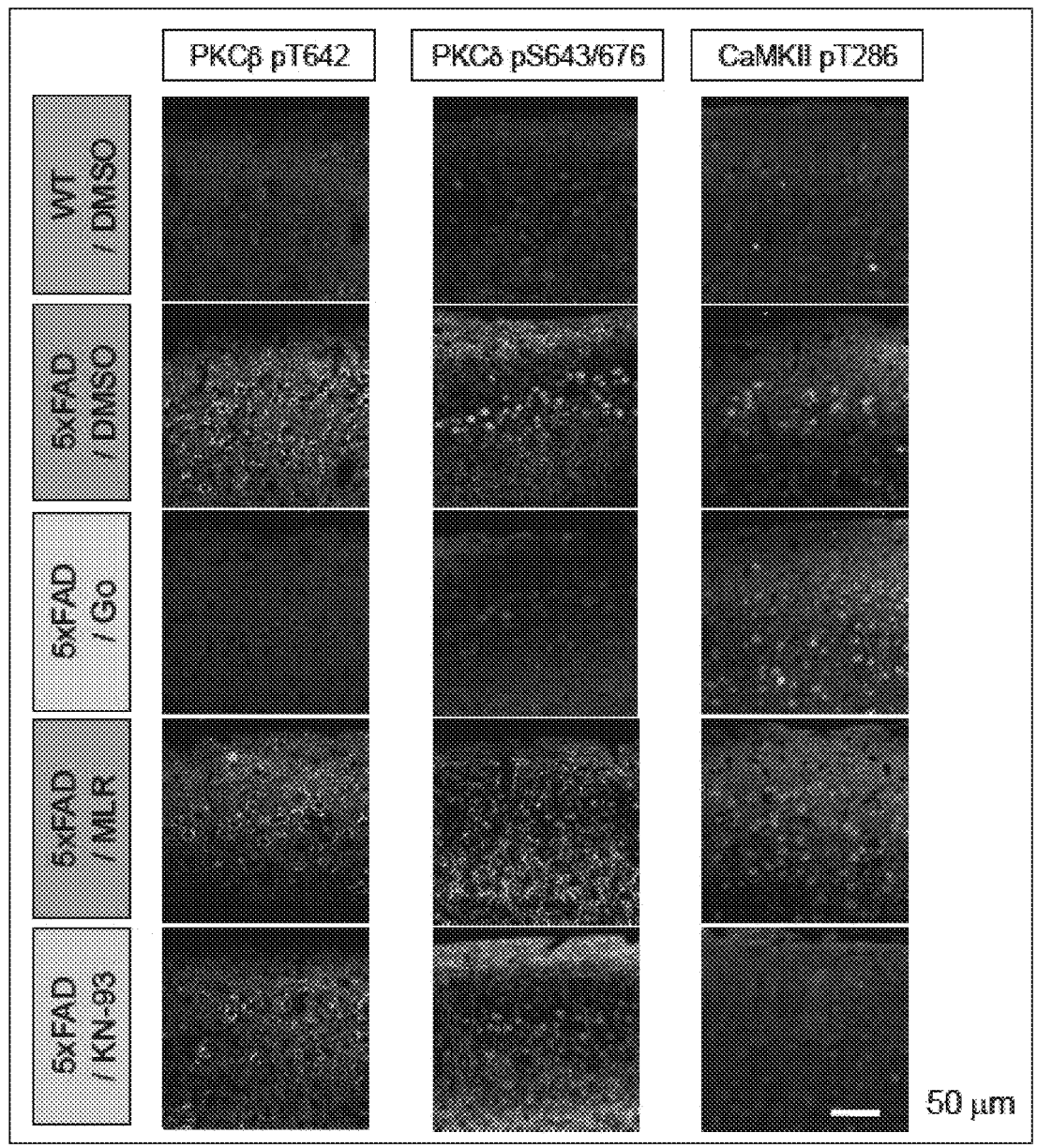
FIG. 10 shows micrographs for illustrating the result of analyzing the cerebral cortexes of WT/DMSO (the background mice treated with DMSO alone), 5×FAD/DMSO (the 5×FAD mice treated with DMSO alone), 5×FAD/Go (the 5×FAD mice treated with Go6976), 5×FAD/MLR (the 5×FAD mice treated with MLR1023) and 5×FAD/KN-93 (the 5×FAD mice treated with KN-93) by immunohistological staining using antibodies against activated PKCβ (PKCβ pT642), activated PKCδ (PKCδ pS643/676), and activated CamKII (CamKII pT286).
Figure 11:
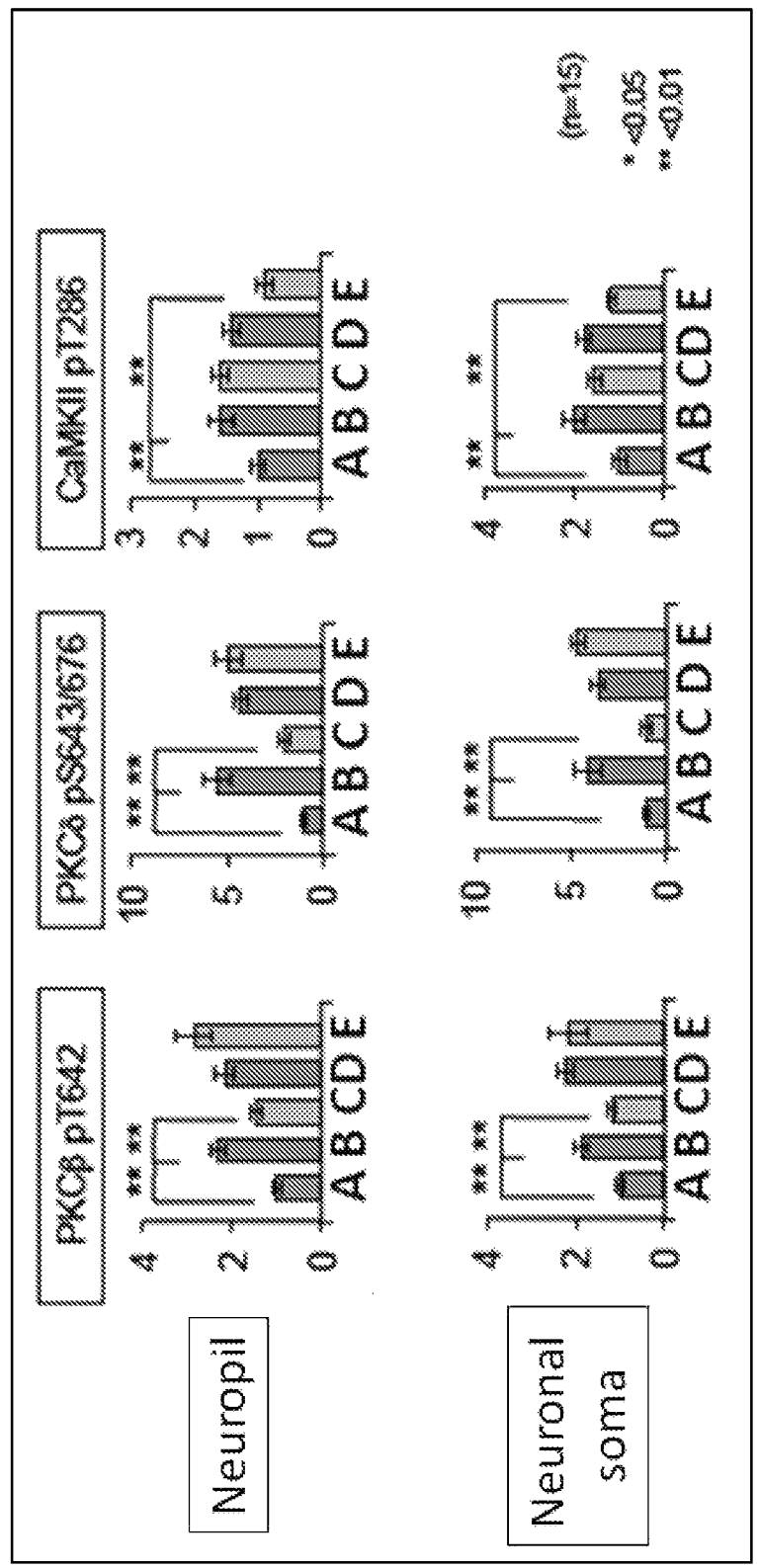
FIG. 11 shows graphs for illustrating the result of quantitatively analyzing signals from each activated kinase in neuronal somas or neuropils of the five types of mice shown in FIG. 10.
Figure 12:
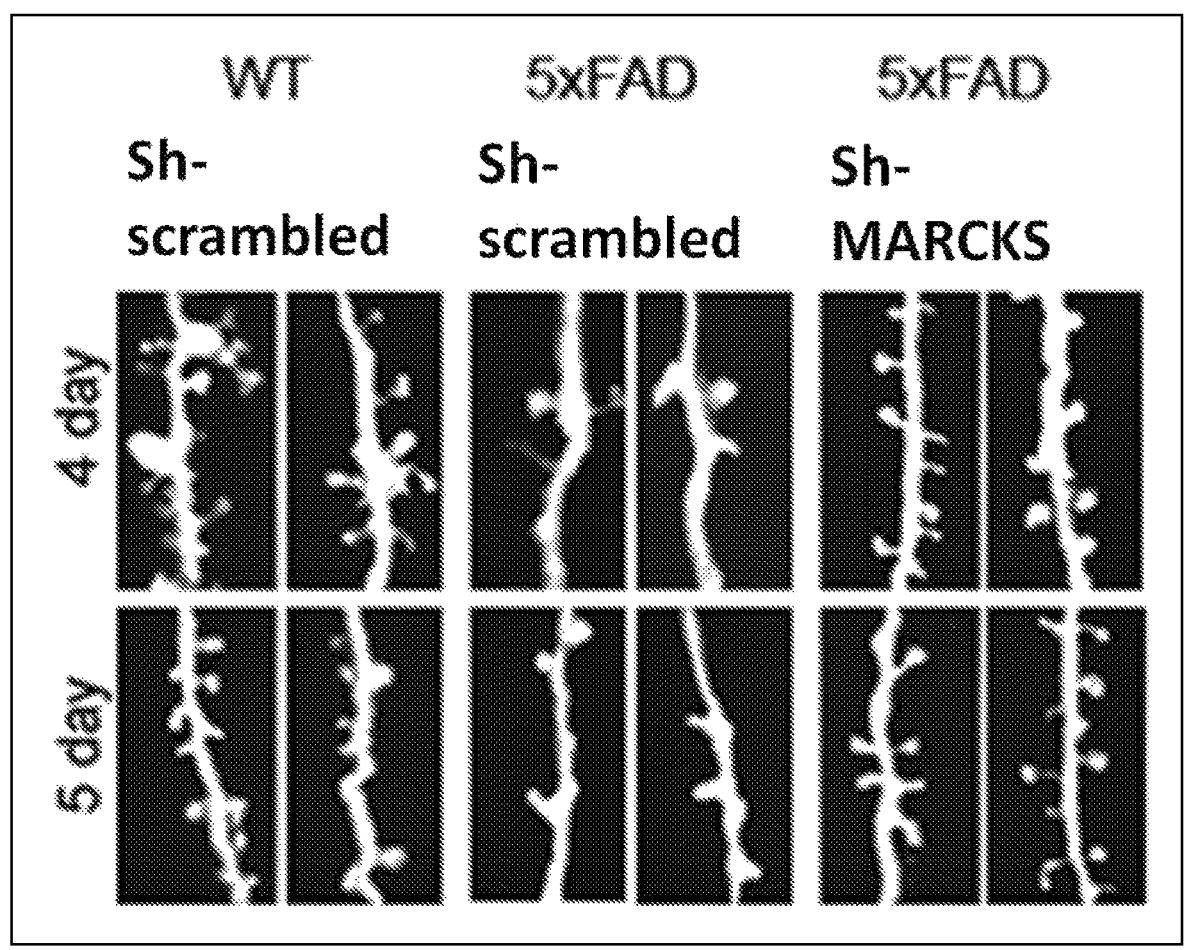
FIG. 12 shows photographs for illustrating the result of injecting a lentiviral vector encoding shRNA against MARCKS into layer 1 of the retrosplenial cortex, and observing dendritic spines/dendrites at the site 4 days and 5 days later. Note that the observation results of injecting scrambled shRNA into 5×FAD mice and background mice thereof (B6/SJL (WT)) as controls are also shown together.
Figure 13:
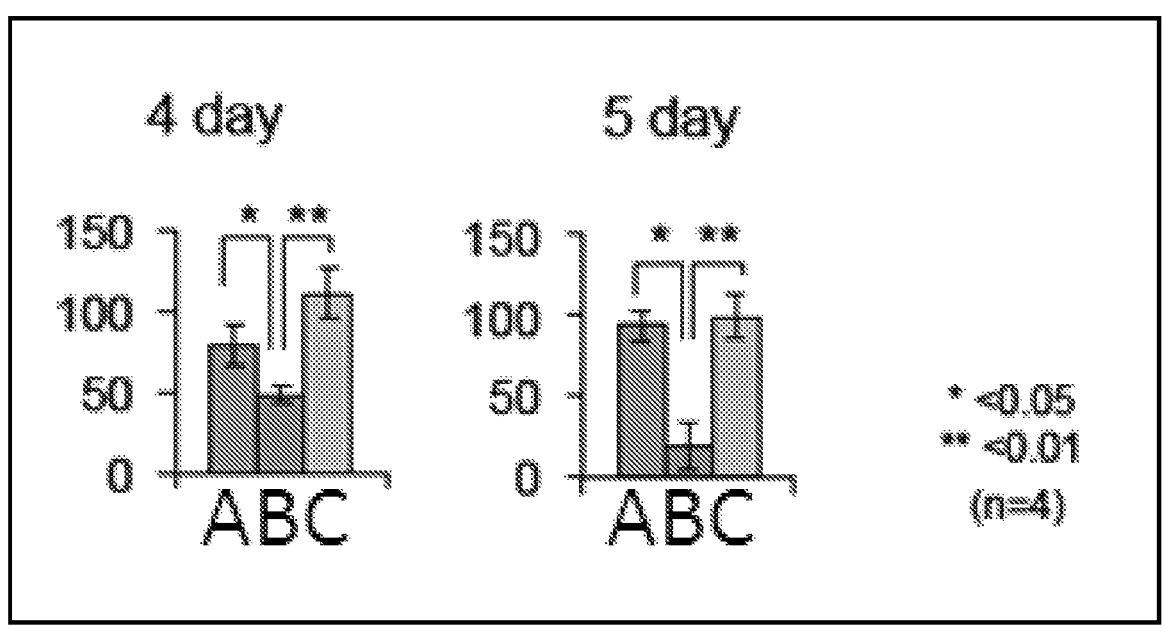
FIG. 13 shows graphs for illustrating the result of quantitatively analyzing the dendritic spine densities in the 5×FAD mice 4 days and 5 days after the shRNA against MARCKS was injected. In the figure, A shows the result of injecting the scrambled shRNA into the background (WT) mice, B shows the result of injecting the scrambled shRNA into the 5×FAD mice, and C shows the result of injecting the shRNA against MARCKS into the 5×FAD mice. Moreover, each bar graph shows the average value+/−the standard error, and is provided with numerical values (n=4) indicating the number of samples in each injection group. One and two asterisks respectively indicate p<0.05 and p<0.01 in Student's independent t-test (regarding the representations in the figure, the same shall apply to FIGS. 14, 15, 17, and 18).
Figure 14:
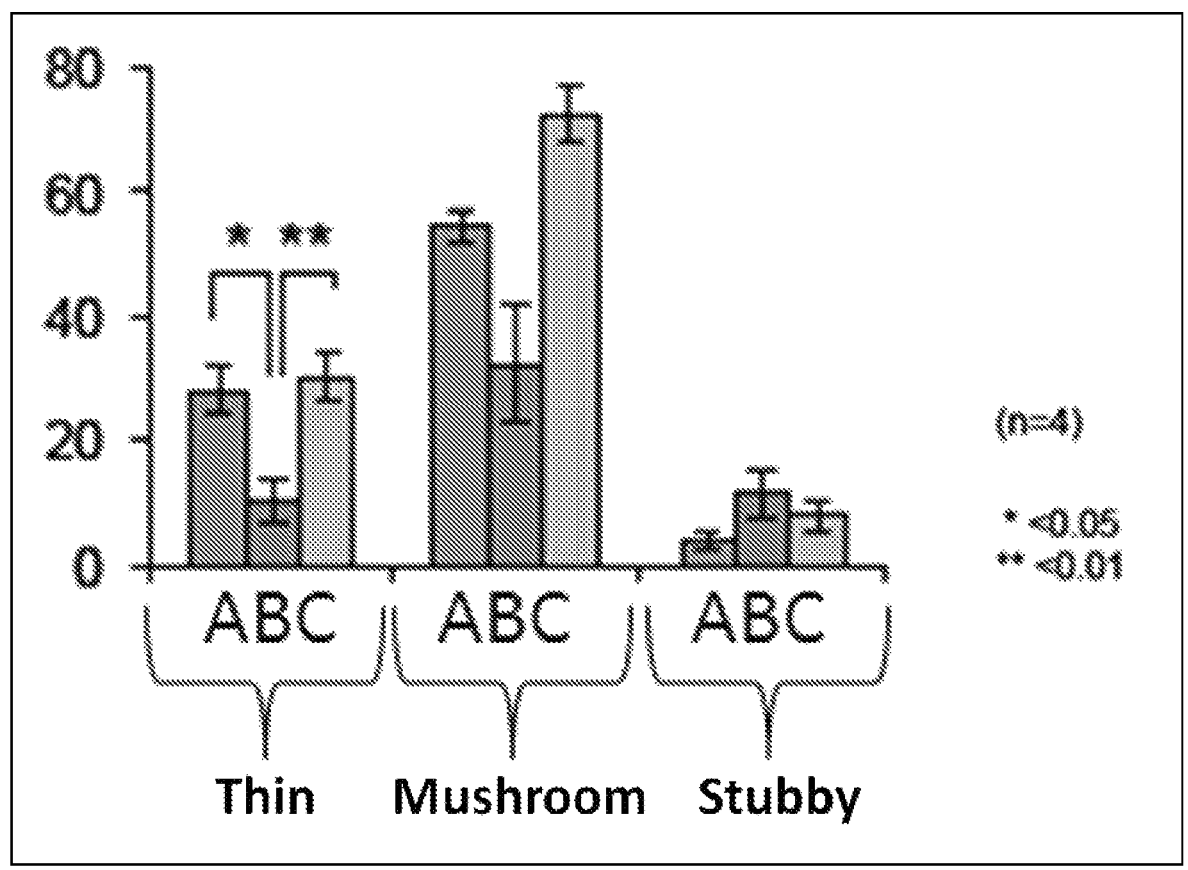
FIG. 14 shows graphs for illustrating the result of quantitatively analyzing the spine type 4 days after the shRNA against MARCKS was injected.
Figure 15:
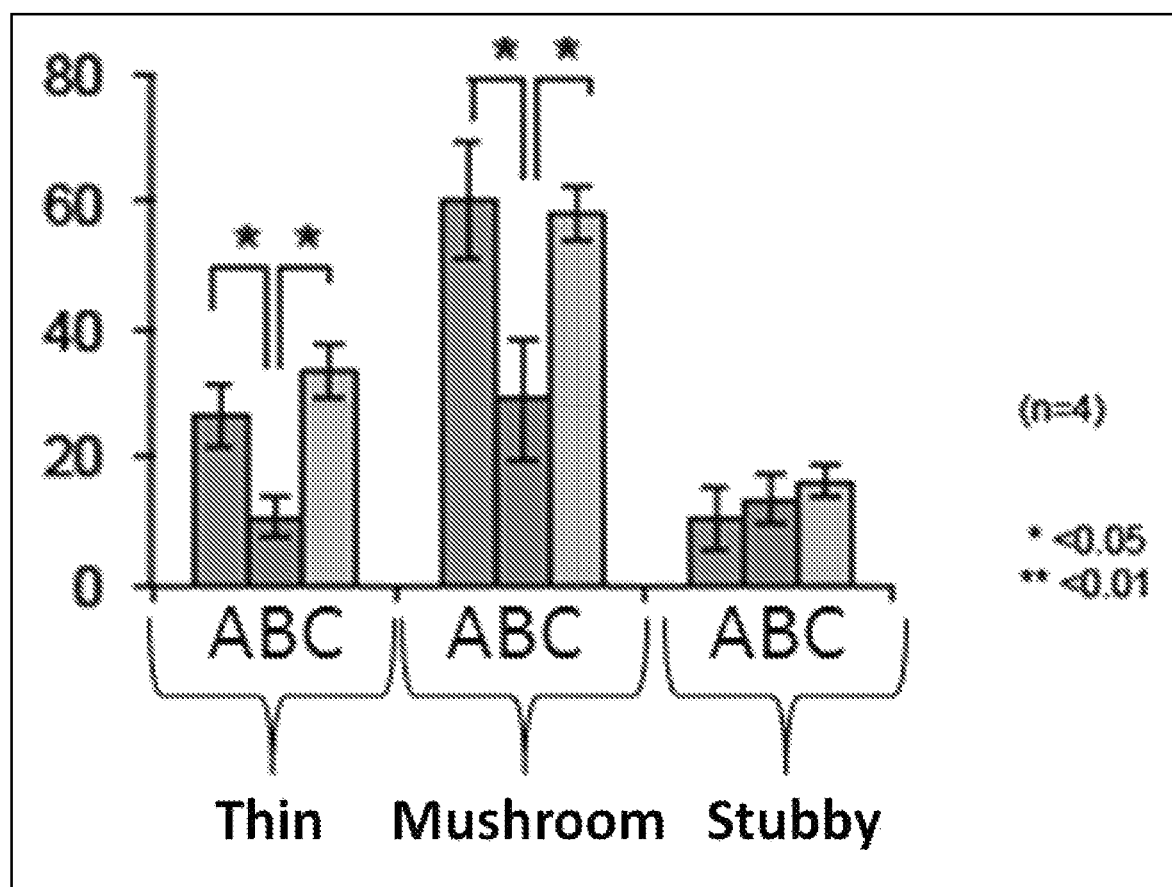
FIG. 15 shows graphs for illustrating the result of quantitatively analyzing the spine type 5 days after the shRNA against MARCKS was injected.
Figure 16:
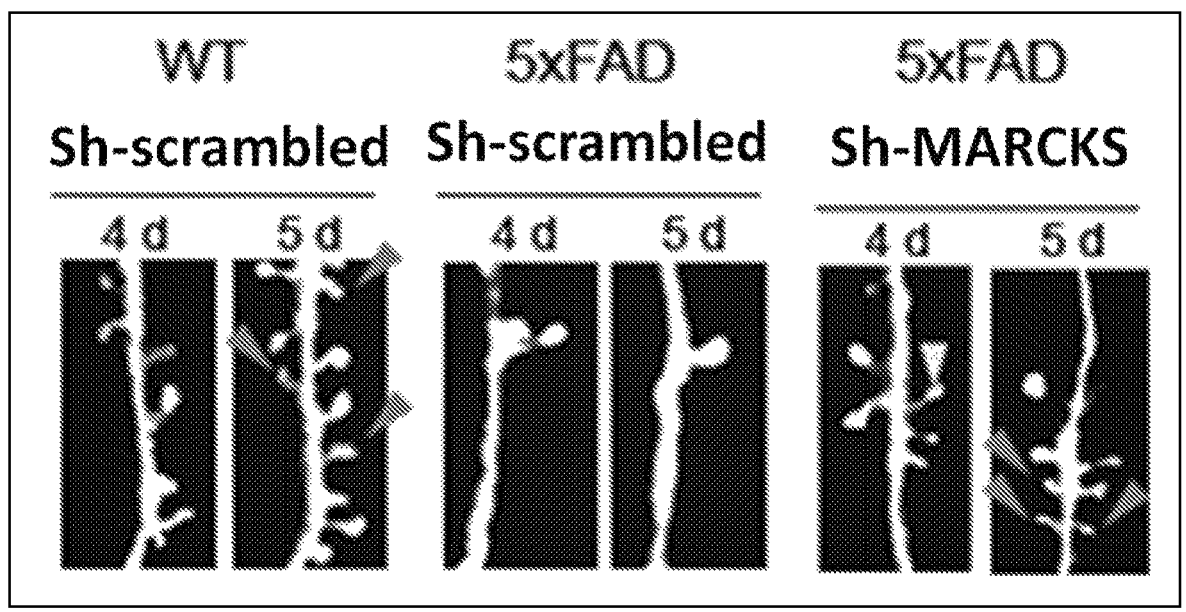
FIG. 16 shows photographs illustrating the spine formation and elimination in the 5×FAD mice 4 days and 5 days after the shRNA against MARCKS was injected. In the figure, the arrow provided to the observation result after 4 days (4d) indicates the spine to be eliminated, while the other arrows indicate formed spines. Note that the observation result of injecting the scrambled shRNA into the 5×FAD mice and the background mice (B6/SJL (WT)) as the controls are also shown together.
Figure 17:
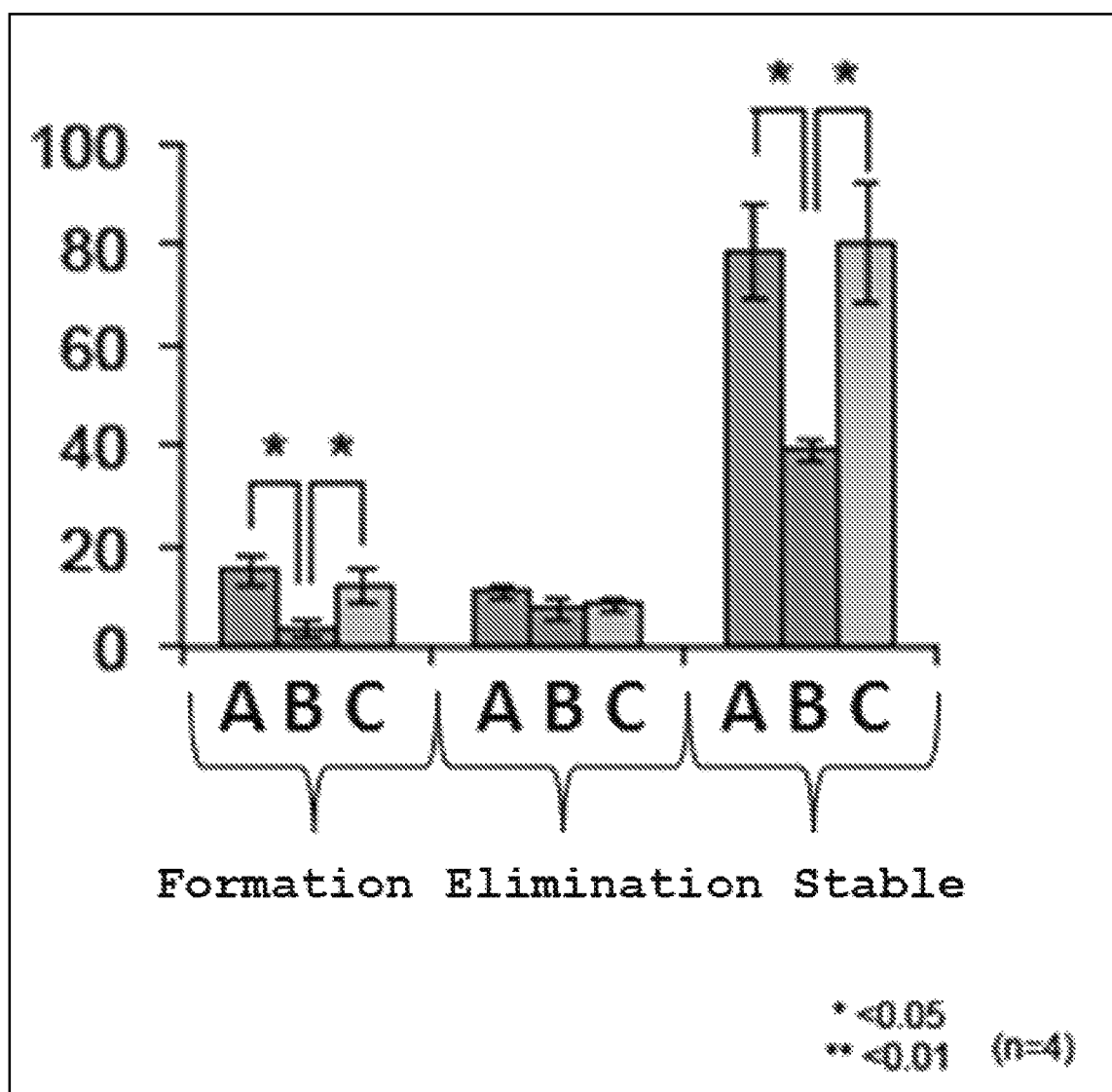
FIG. 17 shows graphs for illustrating the result of quantitatively analyzing the dendritic spine dynamics in the 5×FAD mice in which the shRNA against MARCKS was injected. In the figure, the vertical axis represents the number of formed spines, eliminated spines, or stably remaining spines per 100 μm of the dendritic shaft.
Figure 18:
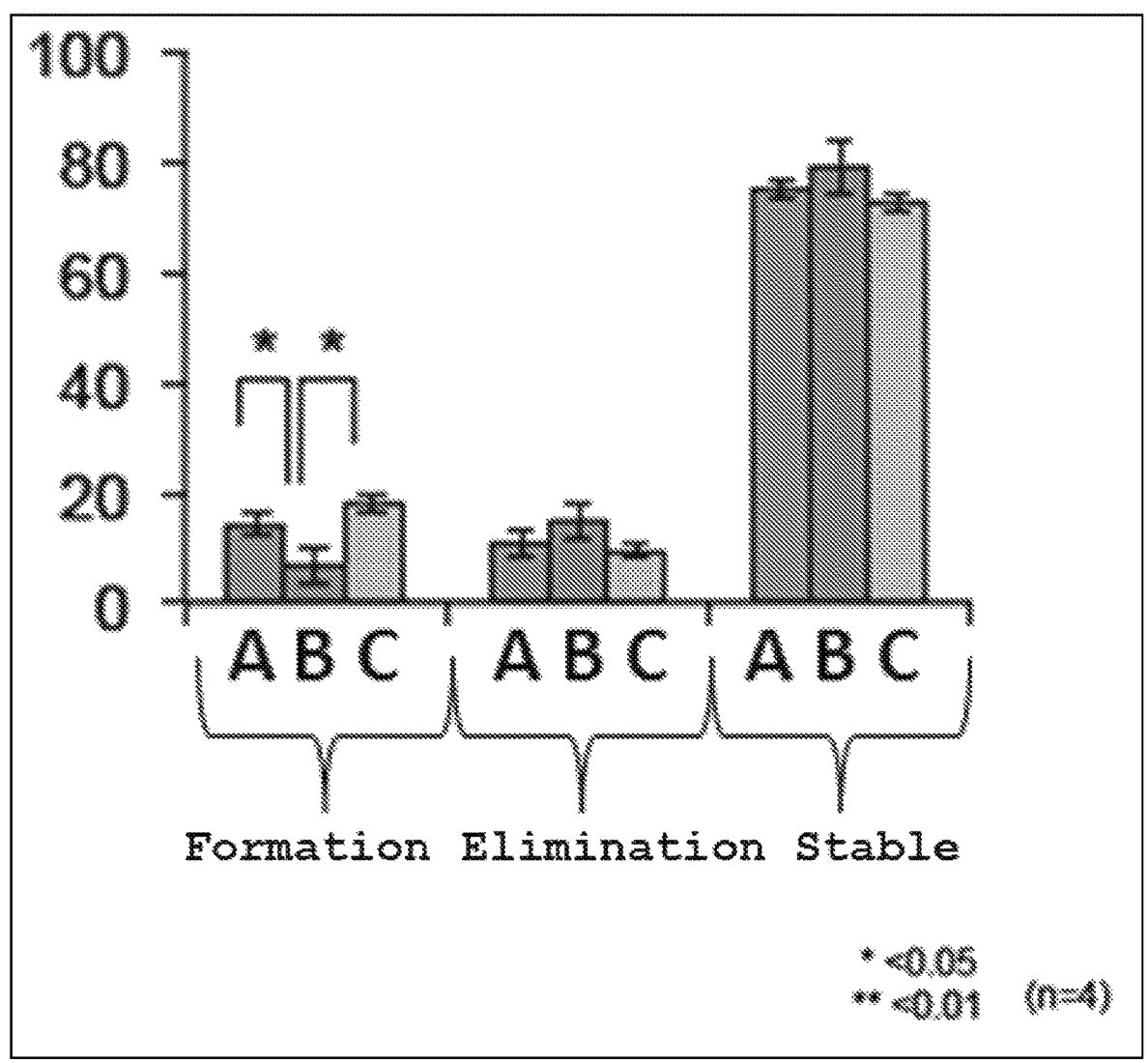
FIG. 18 shows graphs for illustrating the result of quantitatively analyzing the dendritic spine dynamics in the 5×FAD mice in which the shRNA against MARCKS was injected. In the figure, the vertical axis represents the relative percentage of formed spines, eliminated spines, or stably remaining spines.

Furthermore, to confirm the effects of the kinase inhibitors in an in vivo system, an immunohistological analysis was performed targeting brain samples after two-photon microscope observation, and using antibodies against kinases in activated forms. FIGS. 10 and 11 show the obtained result.

As a result, it was verified as shown in FIGS. 10 and 11 that PKCβ, PKCδ, and CamKII (CamKIIα) were activated in the cortical areas (retrosplenial cortexes) of the 5xFAD mice. Moreover, the result of quantifying signals generated from immunostained sites confirmed the above-described effects of the kinase inhibitors.

<Involvement of MARCKS in Spine Pathology of Alzheimer's Disease>

As described above, MARCKS was detected as a protein whose phosphorylation changed at the initial phase of Alzheimer's disease by the aging pattern analysis and also by the aggregation-linked approach described above (see FIG. 34 and FIG. 3). This suggests that MARCKS is the most reliable phosphorylation signal transduction molecule in the pre-onset stage of the pathology of Alzheimer's disease.

To confirm this, MARCKS, which is a substrate of PKC and CamKII, was knocked down in AD model mice. To be more specific, a lentiviral vector expressing a shRNA against MARCK was injected into the cortexes of the 5×FAD mice (12 weeks old) before the onset. FIGS. 12 to 18 show the obtained result.

As apparent from the result shown in FIGS. 12 to 18, the spine pathology in the 5×FAD mice was ameliorated by suppressing the expression of MARCKS with the shRNA.

Moreover, the shRNA against MARCKS recovered the decrease in the number of spines, increased the numbers of immature and matured spines, and further improved the spine formation in the 5×FAD mice.

Example 6

<Search for Kinase Involved in Transition from Amyloid Pathology to Tau Pathology>

In addition to the identification of the specific network in the pre-onset stage of Alzheimer's disease described above, efforts were made to identify a kinase capable of promoting tau phosphorylation.

The proteins selected based on the hypothesis free approach described above did not directly include kinases/phosphatases, but the enhancement of a b-raf protein amount was observed in two 3-month-old AD model mice ($p<0.05$). Moreover, the enhancement was observed in three 1-month-old AD model mice and two 6-month-old AD model mice, too.

Figure 19:
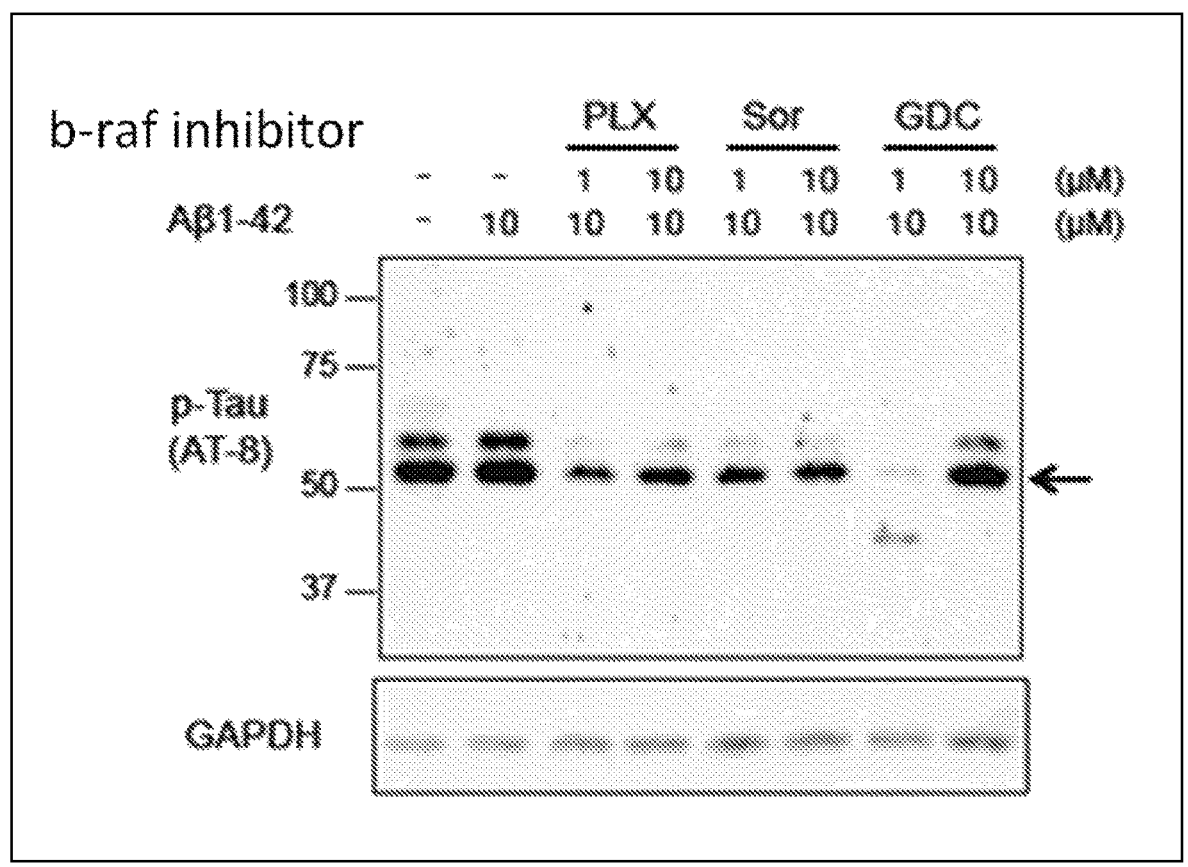
FIG. 19 shows photographs for illustrating the result of treating mouse primary cortical nerve cells (E18) with a 10-μM amyloid β protein (Aβ1-42) in a medium for 6 hours in the presence or absence of a b-raf kinase inhibitor, followed by analysis by western blotting using an anti-phosphorylated tau antibody. Note that, as the b-raf kinase inhibitor, PLX-4720 (PLX), sorafenib (Sor), and GDC-0879 (GDC) were used, each of which was added to the medium at the concentration of 1 μM or 10 μM.
Figure 20:
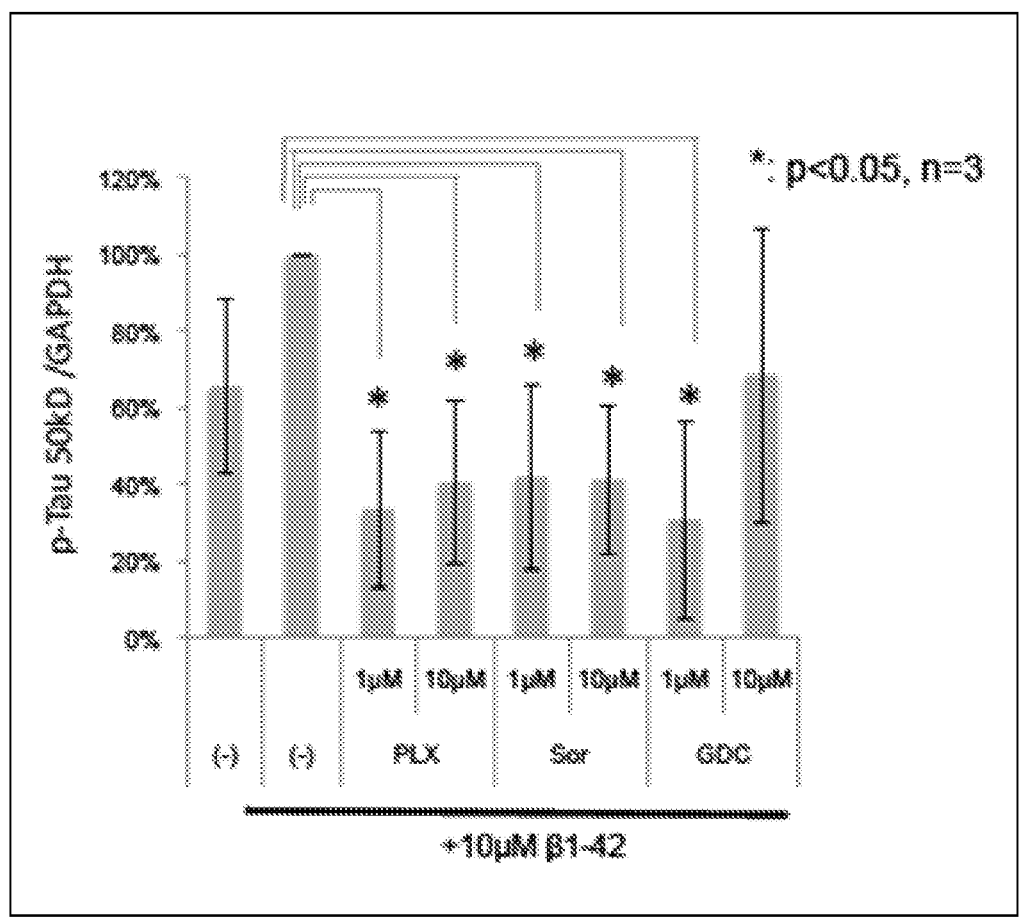
FIG. 20 is a graph for illustrating the result of quantitatively analyzing bands of the western blot shown in FIG. 19. In Student's independent t-test, one asterisk indicates p<0.05 (n=3).

Hence, whether or not inhibiting b-raf actually enabled regulation of tau pathology was tested. To be more specific, an amyloid β protein (Aβ1-42) and three types of b-raf inhibitors were added to primary cultures of cortical nerve cells, and tau phosphorylation in the cortical nerve cells was analyzed. Note that it has been revealed that treating cortical nerve cells with Aβ enhances tau phosphorylation. FIGS. 19 and 20 show the obtained result.

As apparent from the result shown in FIGS. 19 and 20, the tau phosphorylation was suppressed in the Aβ-treated cortical nerve cells. Moreover, although unillustrated, the enhancement of tau phosphorylation was commonly observed in severe AD model mice (5×FAD, APP) and tau model mice at the age of 1 month. To be more specific, this means the tau phosphorylation surprisingly starts in the brains of young AD model mice (1 month old) before immunohistological and symptomatic changes.

Thus, the above result suggested that b-raf was involved in the promotion of the transition from amyloid pathology to tau pathology.

—Frontotemporal Lobar Degeneration—

In the present Examples, next, analyses were performed by employing experimental methods and so forth described below to identify a signal transduction pathway which played a central role in a pre-onset stage of frontotemporal lobar degeneration, and consequently to provide target molecules useful in the diagnosis and treatment of frontotemporal lobar degeneration. Additionally, experiments other than those specifically described below were conducted as in the case of the above Alzheimer's disease analyses, unless otherwise specifically stated.

<Frontotemporal Lobar Degeneration Model Mice>

In the present Examples, frontotemporal lobar degeneration model mice were prepared to search for the target molecules.

It has been known that arginine at position 504 of the PGRN (progranulin) protein is conserved across species, and that a point mutation at this site mainly causes dementia (see Nicholson, A. M. et al., Alzheimers Res. Ther. 4, 4 (2012), Le Ber, I. et al., Hum. Mutat., 2007, Vol. 28, pp. 846 to 855).

Hence, in order to introduce a stop mutation into this site, heterozygous PGRN-R504X mutation knockin mice were prepared. In the preparation, a Neo cassette was inserted in C57BL/6J mice.

To be more specific, first, a targeting vector for the knockin mice preparation was constructed using the following two types of constructs.

(Construct 1)

A 6.5-kbp NotI-XhoI fragment with the R504X mutation was amplified by PCR from a Bac clone (ID: RP23-311P1 or RP23-137J17) and subcloned into a pBS-DTA vector (manufactured by Unitech Co., Ltd.).

(Construct 2)

A 2999-bp ClaI-XhoI fragment was amplified by PCR and subcloned into a pBS-LNL(−) vector (manufactured by Unitech Co., Ltd.) with the Neo cassette.

Then, the BamHI (Blunt)-XhoI fragment derived from the construct 2 was inserted between XhoI (Blunt)-SalI sites of the construct 1 and subcloned. The vector thus obtained was used as a targeting vector.

Next, the targeting vector was linearized by SwaI treatment, and then introduced into ES clones of C57BL/6J mice by electropolation. The genotype analysis of the ES clones was performed by PCR. Positive clones in this analysis were analyzed by Southern blotting using a probe for neomycin (Neo). Then, ES clones confirmed to have homologous recombination occurred between the targeting vector and the genome of the C57BL/6J mice were injected into a mouse early embryo to prepare chimeric mice. Subsequently, the chimeric mice were bred with CAC-Cre mice to remove the Neo cassette in the F1 mouse genome. Further, using the genomic DNA prepared from the tail of the F1 mouse thus obtained, individuals in which the PGRN mutation was introduce by the knockin were selected from these mice. Thus, PGRN-KI mice were established. Note that, unless otherwise specifically stated, the PGRN-KI mice described below refer to the heterozygotes.

Moreover, the PGRN-KI mice thus prepared were subjected to a western blot analysis using an anti-PGRN antibody. It was confirmed that an amount of the full-length PGRN protein expressed was reduced in the cerebral cortexes of the mice. Further, as predicted from the nonsense-mediated RNA decay mechanism, the quantitative PCR confirmed that an amount of the mutant mRNA expressed was also reduced in the PGRN-KI mice. Furthermore, PGRN of the PGRN-KI mice was immunostained, and the result was collated with that of a nerve-cell marker protein NeuN. From this, it was suggested that the reductions of the PGRN in both the cerebral cortex and the cerebellum were mainly attributable to the reduction in nerve cells.

In addition, interestingly, the body weights of the PGRN-KI mice at birth were lighter than those of mice having the same genetic background used as a control (C57BL/6J, hereinafter also referred to as "background mice"). Nonetheless, 20 weeks afterbirth, the body weights of most of the PGRN-KI mice were not much different from that of the wild type. Further, the weight of the brain was slightly light in comparison with the control, but no structural abnormality was observed.

<Recovery Experiment with Vemurafenib and shRNA>

A pharmacological recovery experiment was conducted on the PGRN-KI mice as follows. To be more specific, an osmotic pump (1 μl/hour, 1003D, manufactured by Durect Corporation) was introduced into the subarachnoid cavity of a 12-week-old mouse, and 1.7 µM vemurafenib (S1267, manufactured by Selleckchem Chemicals) or PBS was supplied for 3 days. In addition, 0, 8, and 24 hours on Day 3 after the introduction, imaging was performed.

Moreover, 3 µl of a shRNA-Tau lentiviral vector (sc-430402-V, manufactured by Santa Cruz Biotechnology Inc., $1\times10^6$TU) or scrambled shRNA (SC-108080, manufactured by Santa Cruz Biotechnology Inc., $1\times10^6$ TU) was injected into the same region as in the case of AAV1-EGFP (regarding AAV1-EGFP, see <In Vivo Imaging with Two-Photon Microscope> for Alzheimer's disease described above). In addition, 0, 8, and 24 hours on Day 5 after the shRNA injection, imaging was performed.

<Analysis on Mislocalization of Tau Protein in Spine>

A coimmunostaining analysis was performed using an anti-PSD-95 antibody and an anti-phosphorylated tau antibody (Ser203 or Thr220). To be more specific, paraffin sections (5 µm) were prepared from retrosplenial cortex (RSD) tissues of the PGRN-KI mice and so on, co-stained with the antibodies, and observed by LSM510 confocal microscope (manufactured by Zeiss, objective magnification: ×63, zoom 1, Z-stack images were set at intervals of 0.8 µm).

In the co-localization analysis, the number of sites where phosphorylated tau and PSD-95 signals overlapped with each other was counted in the obtained images (143 µm×143 µm)

Moreover, the fluorescent signal intensity derived from the phosphorylated tau or PSD-95 was quantified using ZEN lite 2012 (manufactured by Zeiss). An average pixel intensity per ROI (20 µm×20 µm) was calculated.

Then, data were obtained from randomly set 10 images, and used for the comparison between the mouse groups by statistical analyses (one-way analysis of variance and Tukey's multiple comparison test).

Reference Example

<Phenotype Analysis on PGRN-KI Mice>

First, analyzed was whether or not the PGRN-KI mice having the stop mutation introduced in the PGRN (progranulin) gene as described above would exhibit the frontotemporal lobar degeneration (FTLD) phenotype.

PGRN-related FTLD is classified as FTLD-TDP characterized by TDP43 aggregates in the nucleus and cytoplasm. Note that TDP43 is a nuclear protein involved in RNA processing, but the aggregate may be formed by the cytoplasmic translocation.

Hence, brain tissues of the PGRN-KI mice were stained with an anti-TDP43 antibody. As a result, although unillustrated, signal intensities of the TDP43 staining were not uniform in the frontal cortexes of the PGRN-KI mice from the age of 1 month. Moreover, the number of nerve cells not stained or weakly stained with the anti-TDP43 antibody was apparently increased in the PGRN-KI mice in comparison with that of the background mice. Further, the difference became remarkable over time.

In addition, cytoplasmic inclusion, lentiform intranuclear inclusion, and cytoplasmic TDP43 staining were observed in the PGRN-KI mice. Further, in the mice, ubiquitin-positive aggregates were also observed.

These characteristics were pathological findings observed in PGRN-related FTLD of human. Thus, it was revealed that the PGRN-KI mice were pathologically similar to patients of this disease.

On the other hand, p62 and FUS inclusion, which are rarely observed in human pathology, were observed in the PGRN-KI mice as an atypical finding. These inclusions recognized by an anti-p62 antibody or an anti-FUS antibody were detected in the frontal cortexes (M2) at the age of 4 months, and spread to the parietal cortexes at the age of 6 months. Meanwhile, in the PGRN-KI mice, an apparent increase in apoptosis, which would be detected by Tunel staining, was not observed until the age of 12 months.

Further, in addition to the analysis on the protein aggregate, whether or not an inflammation was activated in the PGRN-KI mice was analyzed. Note that, such inflammation activation is a characteristic commonly observed across many neurodegenerative diseases. An immunostaining was performed on the PGRN-KI mice using an anti-IBA1 antibody and an anti-GFAP antibody. The result revealed that inflammation was activated in each of microglia and astrocytes. Moreover, such inflammation activations were also confirmed by quantitative PCR targeting IL-1b and Cox-2. However, the invasion of CD4- or CD8-positive cells was not observed.

Further, another common characteristic of neurodegenerative diseases includes DNA damage. An apparent increase in γH2AX focus formation was observed in cortical nerve cells at the age of 6 months. This revealed that DNA damage occurred in the PGRN-KI mice, too.

Furthermore, the PGRN-KI mice were also subjected to six behavioral tests as in the case of Alzheimer's disease model mice described above. As a result, abnormalities regarding anxiety memory and anxiety-related memory were not observed in the open-field test, the light-dark box test, and the elevated plus maze test. Nevertheless, an apparent decrease in memory formation was observed in the fear-conditioning test. Note that it can be said that this decrease in the memory formation was not due to a disorder in a sensory function or motor function because no abnormal score was observed in the rotarod test. Moreover, in the Morris water maze test, a statistically significant decrease was observed from the age of 3 months in the time during which the mice stayed in the target region or the number of times the mice passed through the target. This result supported the loss of the memory formation in the PGRN-KI mice. Note that, in the Morris water maze test using the PGRN-KI mice, the mice received the 60-second trial four times a day for 5 days to learn the position of the platform (target region). Then, the test was conducted under a condition where the platform was removed to measure the time during which the mice stayed in the target region where the platform was originally located and the number of times the mice passed through the target. Additionally, these characteristics observed in the behavioral tests basically agree with clinical symptoms of FTLD patients having an R504 stop mutation which mainly develops dementia.

As described above, the PGRN-KI mice reflected both the pathological observations and the clinical symptoms of FTLD patients, revealing that the mice were quite useful as FTLD model animals.

Example 7

<Phosphoproteome Analysis on FTLD>

Using the PGRN-KI mice whose usefulness as FTLD model animals was verified, efforts were made, as in the case of the above Alzheimer's disease analyses, to comprehensively analyze (phosphoproteome analysis) phosphorylation signal transductions in FTLD also to identify a phosphorylation signal transduction which played a central role in a pathology of the disease.

Particularly, PGRN has been reported to exhibit an antagonistic action against TNF; on the other hand, contradictory results have also been reported (see NPLs 17 to 21). To elucidate this contradiction, a comprehensive proteome analysis was performed on the cerebral cortex tissues of the PGRN-KI mice to examine, in the brains of the PGRN mutation-related FTLD model mice, whether a TNF signal transduction pathway was activated or a different type of signal transduction pathway was activated.

To be more specific, the comprehensive proteome analysis was performed as in the case of Alzheimer's disease described above using ABSCIEX 5600 and targeting the cerebral cortex tissues derived from three PGRN-KI mice and those derived from three background mice (C57BL/6J).

Then, based on the comprehensive proteome data thus constructed, whether or not the TNF signal transduction pathway was activated in the cerebral cortex tissues of the PGRN-KI mice was examined. Concretely, using signal transduction pathway-related database (http://www.genome.jp/kegg/pathway.html) of KEGG (Kyoto Encyclopedia of Genes and Genomes), proteins belonging to the TNF signal transduction pathway were searched for proteins whose phosphorylation states changed in the PGRN-KI mice and C57BL/6J mice. As a result, surprisingly, no protein whose phosphorylation changed was found in the TNF signal transduction pathway per se for 1 to 6 months after birth and after the onset.

Hence, next, an analysis was performed targeting 16 TNF-related signal transduction pathways including an adipocytokine signal transduction pathway, a NF-kB signal transduction pathway, and an apoptosis signal transduction pathway. The result revealed that, in a MAPK signal transduction pathway, an mTOR signal transduction pathway, and a signal transduction pathway related to antigen processing and presentation, phosphorylations of proteins belonging to these signal transduction pathways remarkably changed in the PGRN-KI mice in comparison with the C57BL/6J mice.

Further, it was also revealed that, in these signal transduction pathways, the most remarkable change in the phosphorylation was focused on the MAPK signal transduction pathway which would lead to tau protein phosphorylation. Note that the mTOR signal transduction pathway and the MAPK signal transduction pathway were common in PKC activation. On the other hand, in the signal transduction pathway related to antigen processing and presentation, the protein phosphorylation varied for 1 to 6 months after birth.

The MAPK signal transduction pathway was apparently activated in the PGRN-KI mice from the pre-onset stage. During the period of symptom progression also, multiple proteins belonging to the signal transduction pathway were in high phosphorylation states all the time.

Particularly, in seven proteins, b-raf, PKCα, PKCβ, PKCγ, tau, MAP2K1 (mitogen-activated protein kinase kinase 1, MAP kinase kinase 1, MEK-1), and stathmin belonging to the MAPK signal transduction pathway, the phosphorylations at one or two amino acid sites of each of these proteins (phosphopeptide amounts detected by the mass spectrometry) remarkably changed in the PGRN-KI mice in comparison with the C57BL/6J mice.

Importantly, the phosphorylation of the tau protein significantly changed at multiple sites. Particularly, serine at position 203, threonine at position 220, and serine at position 393 of the tau protein (corresponding respectively to serine at position 214, threonine at position 231, and serine at position 404 of human tau protein) were in high phosphorylation states all the time during the above-described period, or the phosphorylations were enhanced over time.

Moreover, regarding b-raf and PKCγ also, one or multiple sites thereof were in high phosphorylation states all the time, or the phosphorylations were enhanced over time.

More concretely, in the PGRN-KI mice, the phosphorylation of serine at position 348 of b-raf was 1.1487 times, 1.1795 times, and 1.3664 times (shown are relative values at the ages of 1 month, 3 months, and 6 months, respectively) as high as those of the C57BL/6J mice. Moreover, regarding serine at position 766 of b-raf, the phosphorylation was 1.7508 times and 3.0476 times (shown are relative values at the ages of 3 months and 6 months, respectively). Further, regarding serine at position 769 of b-raf, the phosphorylation was 1.9752 times (shown is a relative value at the age of 6 months). Note that these serine at position 348, serine at position 766, and serine at position 769 of b-raf correspond respectively to serine at position 365, serine at position 729, and serine at position 732 in human.

In addition, for PKCγ, in the PGRN-KI mice, the phosphorylation of threonine at position 655 was 1.2052 times, 1.1308 times, and 1.5702 times (shown are relative values at the ages of 1 month, 3 months, and 6 months, respectively) as high as those of the C57BL/6J mice. Moreover, regarding serine at position 690 of PKCγ, the phosphorylation was 2.5918 times (shown is a relative value at the age of 1 month). Note that these threonine at position 655 and serine at position 690 of PKCγ correspond respectively to threonine at position 655 and serine at position 690 in human.

Moreover, although unillustrated, regarding serine at position 766 of b-raf and threonine at position 655 of PKCγ, it was confirmed by western blotting that the phosphorylations at these sites in the cerebral cortexes of the 3-month-old PGRN-KI mice were enhanced in comparison with those in the 3-month-old C57BL/6J mice as in the above result of mass spectrometry.

Further, the phosphorylation of MEK-1 (Map2k1) located downstream of b-raf and PKCγ was also analyzed by western blotting. It was confirmed that the phosphorylation in the cerebral cortexes of the PGRN-KI mice at the age of 3 months was also enhanced in comparison with that of the 3-month-old C57BL/6J mice.

Furthermore, an immunohistological analysis using an anti-phosphorylated tau antibody AT8 was performed to detect phosphorylated tau protein in the cytoplasms of the frontal lobe nerve cells of the PGRN-KI mice. As a result, a signal of the phosphorylated tau protein was detected at the age of 12 months.

On the other hand, a signal transduction induced by TNF was analyzed by a co-immunoprecipitation method based on amounts of complexes formed in the signal transduction (TNFR-TRADD complex, TNFR-RIP complex, and TNFR-TRAF2 complex). As a result, no significant difference was found between the PGRN-KI mice and the C57BL/6J mice.

The above results revealed that, in the PGRN-KI mice, the MAPK signal transduction pathway was activated, while the TNF signal transduction pathway was not activated.

Example 8

<Analysis on Therapeutic Effect of b-Raf Inhibitor on Behavioral Phenotype of FTLD Model Mice>

Analyzed was whether or not suppressing an abnormal activation in the MAPK signal transduction pathway by using a b-raf specific inhibitor would recover the behavioral phenotype of the PGRN-KI mice.

Figure 21:
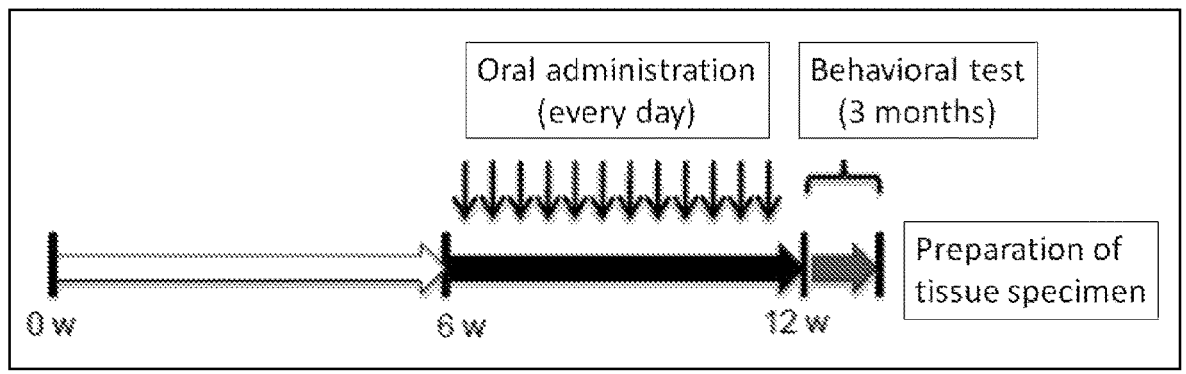
FIG. 21 is a schematic diagram showing a protocol for analyzing the therapeutic effect of a b-raf inhibitor on the behavioral phenotype of FTLD model mice.
Figure 22:
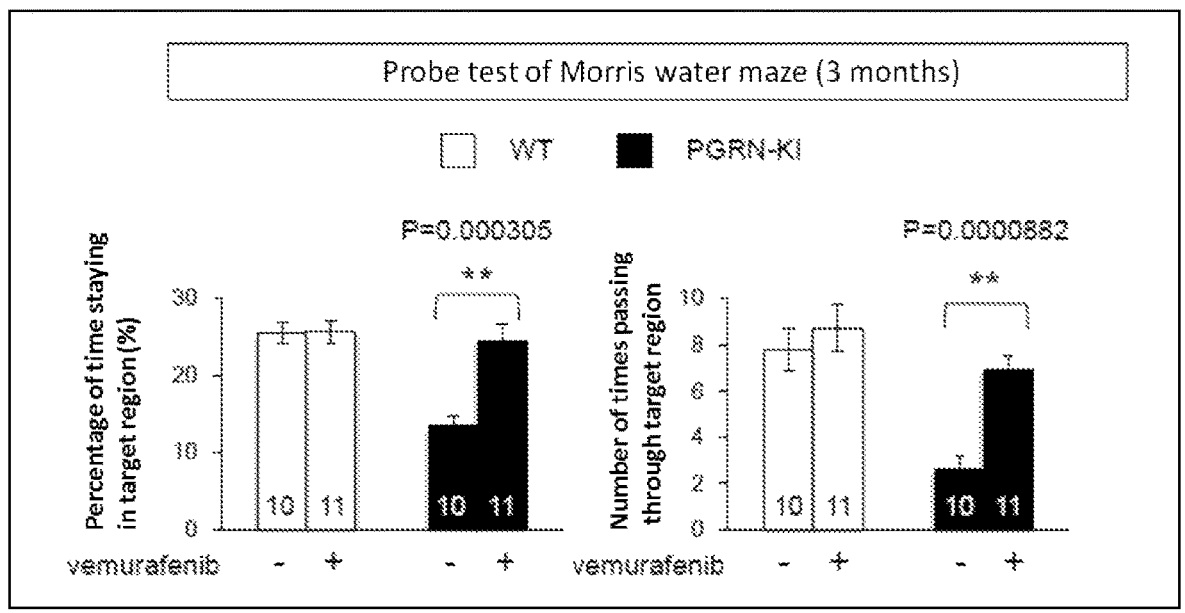
FIG. 22 shows graphs for illustrating the result of providing a b-raf inhibitor (vemurafenib) to FTLD model mice (PGRN-KI mice), and evaluating the behavior of these mice by a Morris water maze test. In the figure, the numbers shown in bars of the graphs indicate the numbers of mice analyzed in each test. Moreover, "-" shows the result (negative control) of mice to which PBS was administered in place of vemurafenib.
Figure 23:
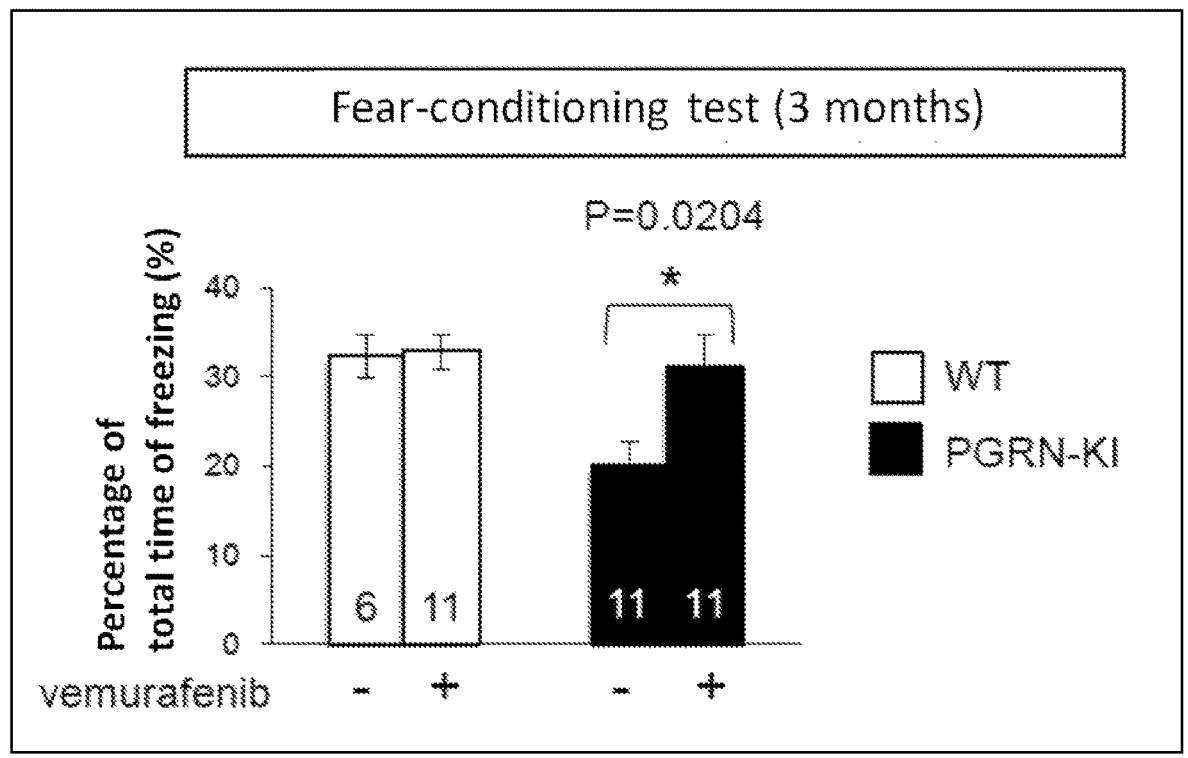
FIG. 23 is a graph for illustrating the result of providing vemurafenib to the PGRN-KI mice, and evaluating the behavior of these mice by a fear-conditioning test (the representations in the figure are the same as FIG. 22).

To be more specific, in accordance with the protocol shown in FIG. 21, a b-raf specific inhibitor vemurafenib or PBS was provided to the 6-week-old PGRN-KI mice every day over 6 weeks. Then, the behaviors of these mice were evaluated in the Morris water maze test and the fear-conditioning test. FIGS. 22 and 23 show the obtained result.

As apparent from the result shown in FIGS. 22 and 23, administering vemurafenib to the PGRN-KI mice remarkably recovered the scores in the two tests.

Figure 24:
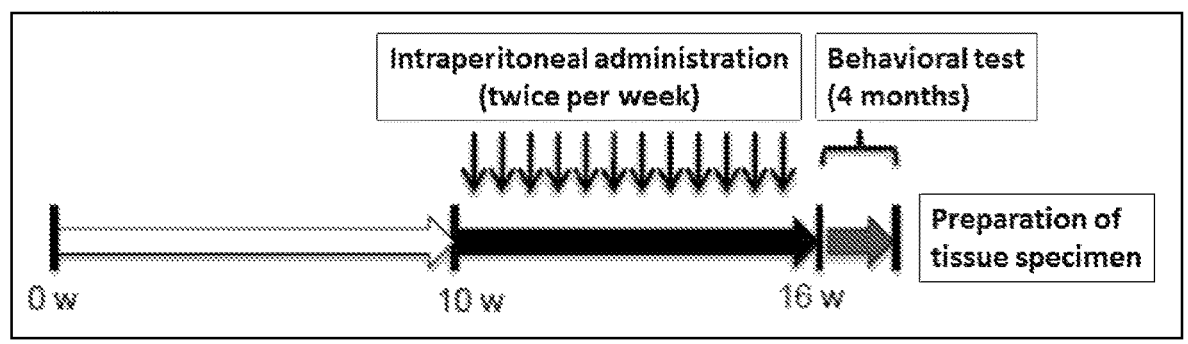
FIG. 24 is a schematic diagram showing a protocol analyzing the therapeutic effect of a TNF signal transduction inhibitor on the behavioral phenotype of the FTLD model mice.
Figure 25:
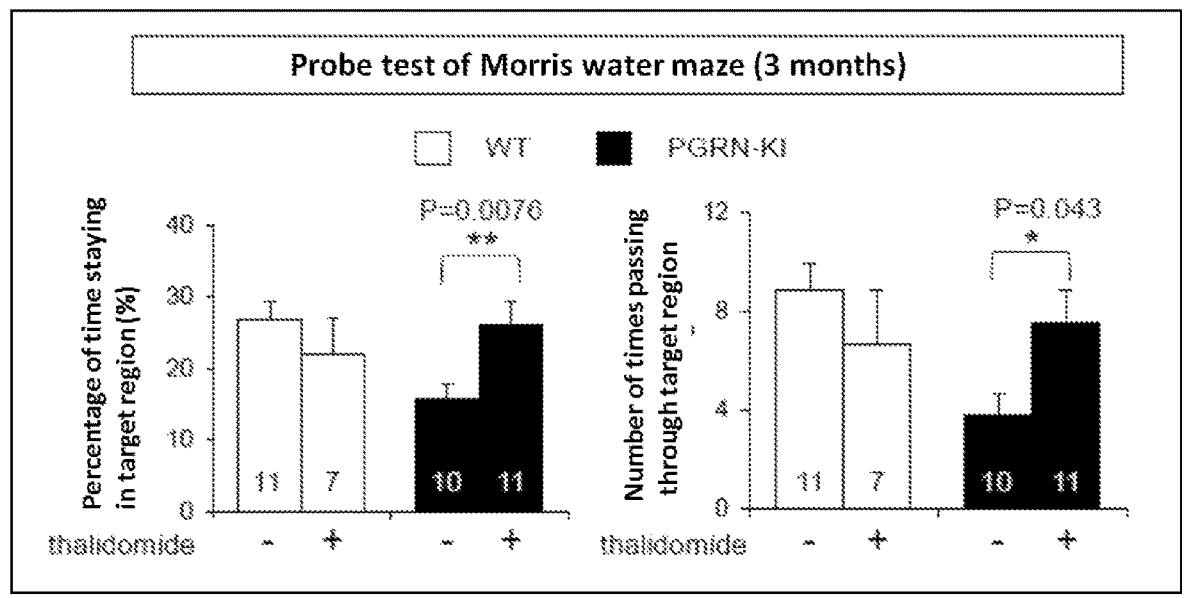
FIG. 25 shows graphs for illustrating the result of providing a TNF signal transduction inhibitor (thalidomide) to the FTLD model mice (PGRN-KI mice), and evaluating the behavior of these mice by the Morris water maze test. In the figure, the numbers shown in bars of the graphs indicate the numbers of mice analyzed in each test. Moreover, "-" shows the result (negative control) of mice to which PBS was administered in place of thalidomide.
Figure 26:
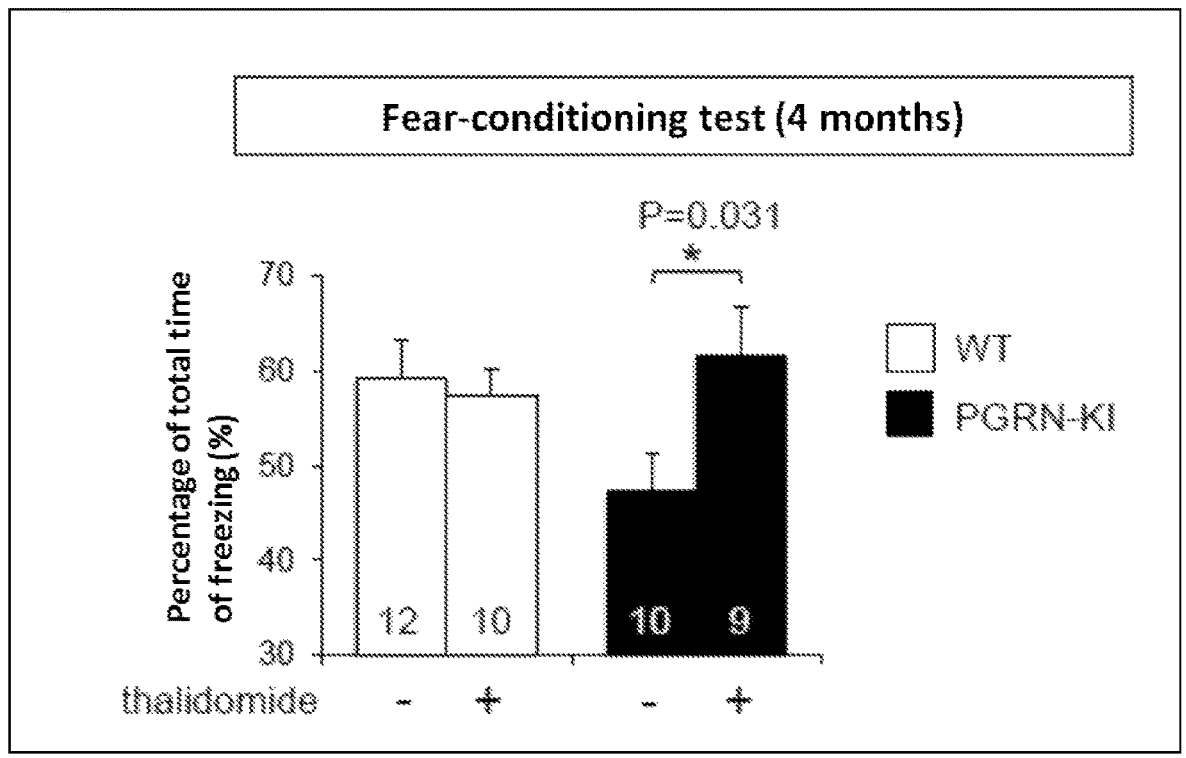
FIG. 26 is a graph for illustrating the result of providing thalidomide to the PGRN-KI mice, and evaluating the behavior of these mice by the fear-conditioning test (the representations in the figure are the same as FIG. 25).

Meanwhile, the therapeutic effect of thalidomide was also tested. Note that thalidomide is known to suppress the TNF signal transduction pathway. Concretely, in accordance with the protocol shown in FIG. 24, thalidomide was administered to the PGRN-KI mice by peritoneal cavity injection every day for the same period as that in the protocol using the b-raf inhibitor. The behaviors of these mice were evaluated by the above two tests. FIGS. 25 and 26 show the obtained result.

As apparent from the result shown in FIGS. 25 and 26, in the thalidomide administration example also, beneficial effects were finally verified regarding the scores in the Morris water maze test and the fear-conditioning test.

Note that such symptom recoveries were not observed in the PBS-administered PGRN-KI mice.

Figure 27:
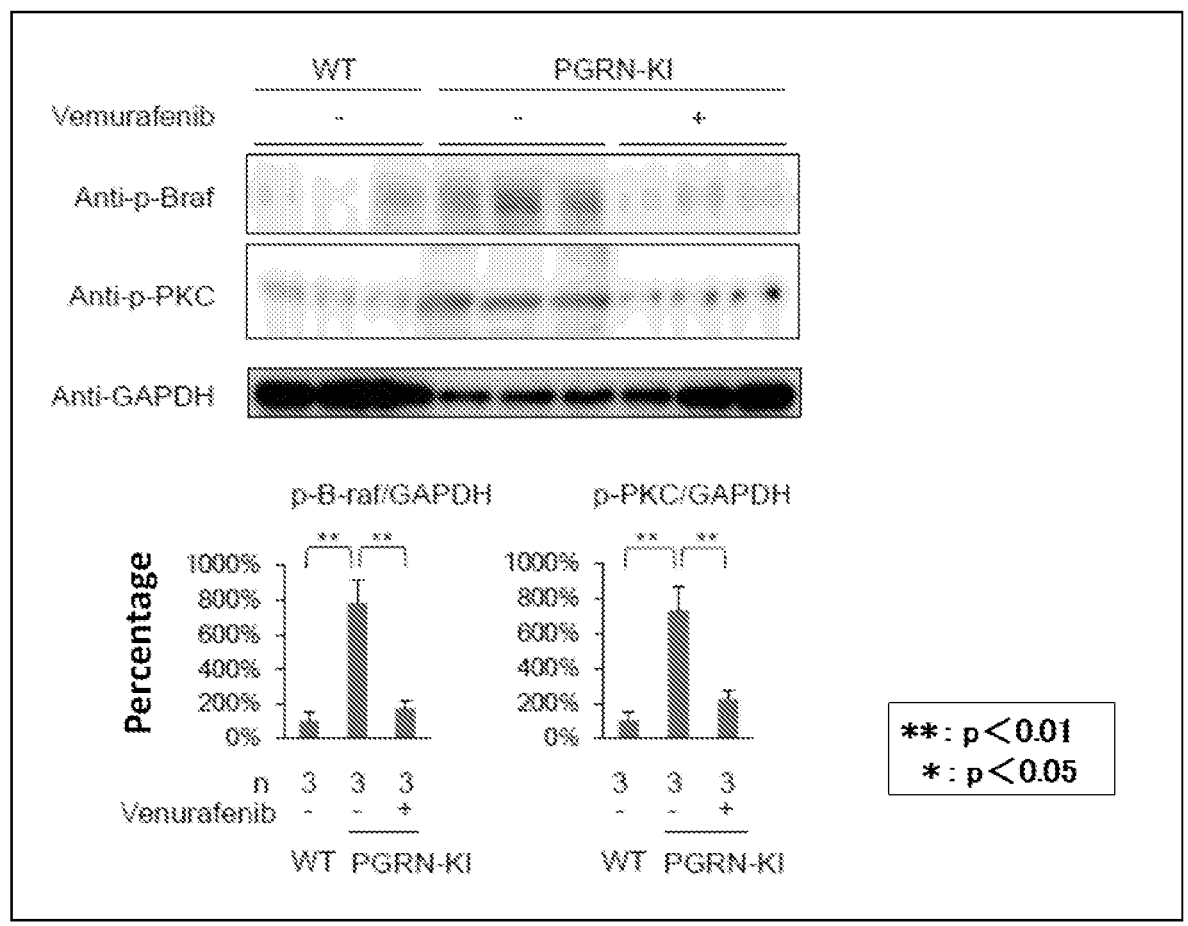
FIG. 27 is a figure for illustrating the result of western blot analysis on the cerebral cortexes of wild-type mice (WT) and the PGRN-KI mice to which vemurafenib was administered. In the figure, the upper panel shows photographs for illustrating the western blot analysis result. "Anti-p-Braf" and "Anti-p-PKC" respectively show the analysis result of phosphorylated b-RAF protein and the analysis result of phosphorylated PKC protein. "Anti-GAPDH" shows the result of detecting a GAPDH protein as an internal standard. Moreover, in the figure, the lower two panels are graphs for illustrating the western blot analysis result: the left side shows the relative value of the phosphorylated b-RAF protein amount based on the GAPDH amount, and the right side shows the relative value of the phosphorylated PKC protein amount based on the GAPDH amount. The significant differences were evaluated based on the P-value calculated by Student's independent t-test.

Moreover, the cerebral cortexes of the PGRN-KI mice treated with the agent were analyzed by western blot. The result confirmed as shown in FIG. 27 that vemurafenib suppressed the b-raf phosphorylation. Further, it was revealed that vemurafenib also suppressed the PKC phosphorylation.

Figure 28:
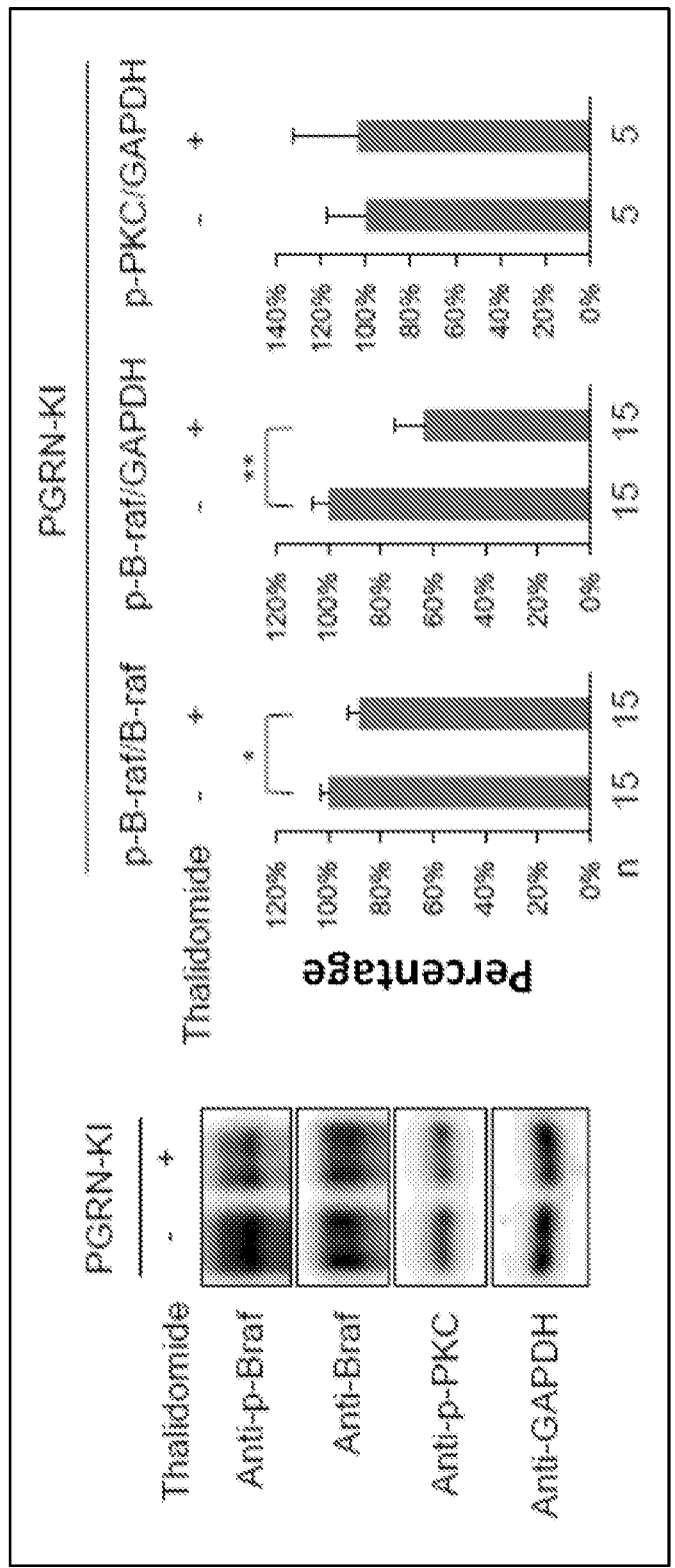
FIG. 28 is a figure for illustrating the result of western blot analysis on the cerebral cortexes of the PGRN-KI mice to which thalidomide was administered. In the figure, the left panel shows photographs for illustrating the western blot analysis result. "Anti-p-Braf", "Anti-Braf", and "Anti-p-PKC" respectively show the analysis result of phosphorylated b-raf protein, the analysis result of b-raf protein, and the analysis result of phosphorylated PKC protein. "Anti-GAPDH" shows the result of detecting a GAPDH protein as an internal standard. Moreover, in the figure, the right panel shows graphs for illustrating the western blot analysis result. "p-B-raf/Braf" shows the relative value of the phosphorylated b-raf protein amount based on a total b-raf protein amount, "p-B-raf/GAPDH" shows the relative value of the phosphorylated b-raf protein amount based on the GAPDH amount, and "p-PKC/GAPDH" shows the relative value of the phosphorylated PKC protein amount based on the GAPDH amount. Further, in the figure, one asterisk indicates $p<0.05$ in Student's independent t-test, and two asterisks indicate $p<0.01$ in Student's independent t-test.

On the other hand, in the thalidomide administration example, the b-raf phosphorylation was suppressing, but the PKC phosphorylation was not suppressed, as apparent from the result shown in FIG. 28.

In sum, these results revealed that the two agents had the therapeutic effects on the FTLD-involved phenotype through the inhibition of the b-raf pathway.

Example 9

<Analysis on Recovery Effect of b-Raf Inhibitor and Tau Knockdown on Spine Phenotype of FTLD Model Mice>

It is known that, in Alzheimer's disease and FTLD-Tau, tau phosphorylation is involved in formation of paired helical filaments (PHF) and aggregation of this protein in the cytoplasm. Moreover, there is a report on a pathological relation between tau and amyloid β (Aβ) in Alzheimer's disease. From these findings, tau is normally believed to be an effector molecule located downstream of Aβ.

In addition, it has recently been revealed that, in an initial pathological stage when Aβ exhibits toxicity on synapse function, tau plays a different important role in synaptic spines.

Further, it is also reported that the transition of tau to spine due to a Fyn kinase which phosphorylates NMDAR enhances a calcium concentration and triggers the destruction of spine cytoskeleton.

Hence, based on the above findings, two hypotheses were proposed and examined. To be more specific, as the first hypothesis, the aforementioned therapeutic effect by suppressing b-raf phosphorylation was presumably based on the elimination of protein aggregation in the nerve by vemurafenib or thalidomide. Accordingly, analyzed was the recovery effect of vemurafenib or thalidomide on the protein aggregation in the cerebral cortexes of the PGRN-KI mice.

However, although unillustrated, in an immunohistological analysis on the brains of the PGRN-KI mice, no significant effect of vemurafenib or thalidomide was observed on FUS and p62 inclusion (IB). Moreover, regarding the transition of TDP43 into the cytoplasm also, no large change was observed in the PGRN-KI mice in which vemurafenib or thalidomide was administered.

Hence, next, the second hypothesis was proposed that synaptic spines were impaired by abnormal tau phosphorylation. To be more specific, the therapeutic effect of vemurafenib or thalidomide was presumably exhibited through the recovery of synaptic spines by suppressing b-raf phosphorylation, and in vivo imaging was performed on synaptic spines with a two-photon microscope.

Figure 29:
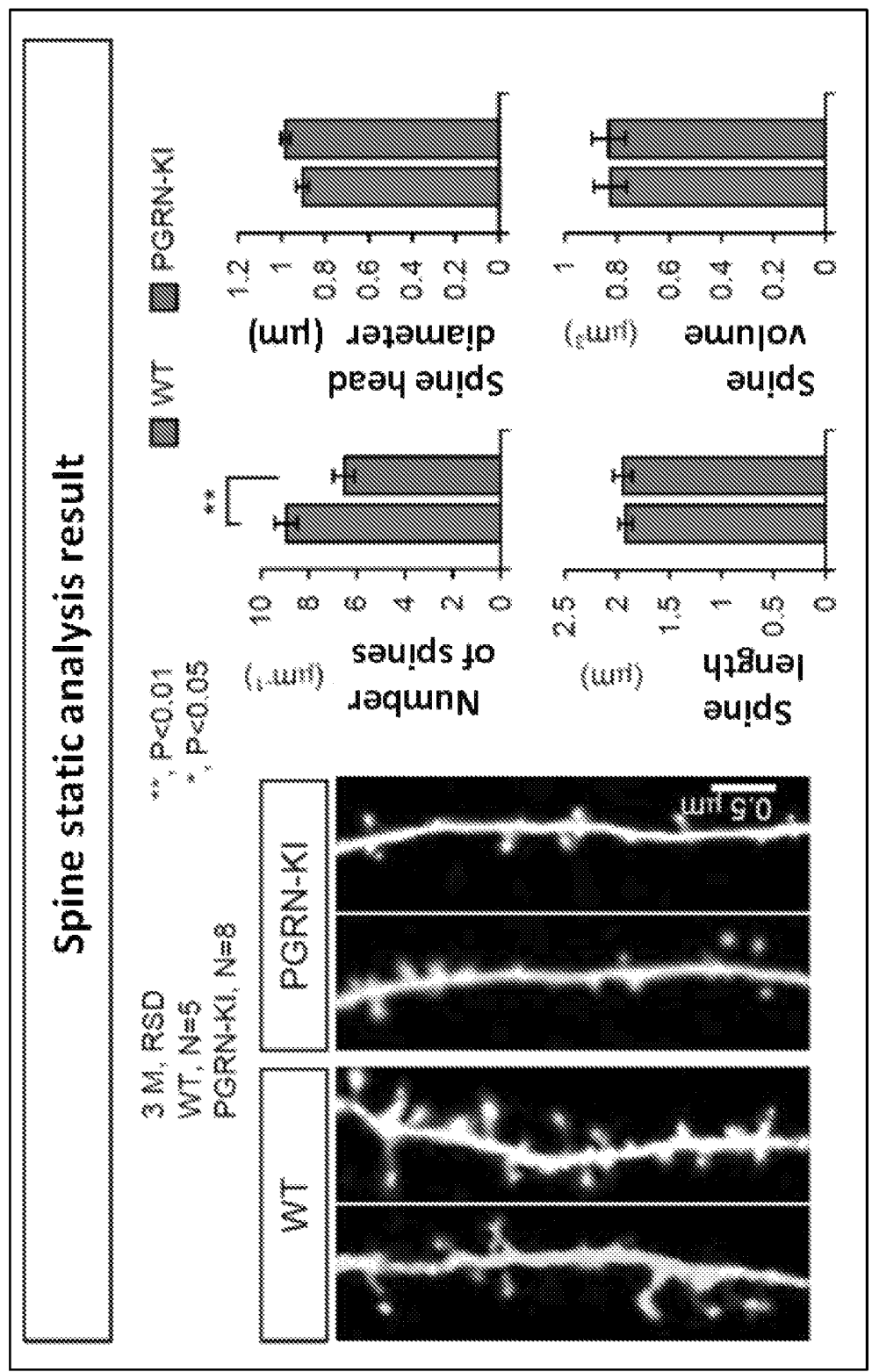
FIG. 29 is a figure for illustrating the result of spine static analysis on the retrosplenial cortexes (RSD) of the FTLD model mice (PGRN-KI mice) and wild-type mice (WT). In the figure, the left panel shows photographs of spines observed with a two-photon microscope. In the figure, graphs in the right panel show the number of spines (the number of spines per 1 μm of the dendrite), spine length, spine head diameter, and spine volume measured by the two-photon microscope observation. Moreover, in each graph, the left bar shows the observation result of the wild-type mice, and the right bar shows the observation result of the PGRN-KI mice. In the figure, two asterisks indicate $p<0.01$ in Student's independent t-test.
Figure 30:
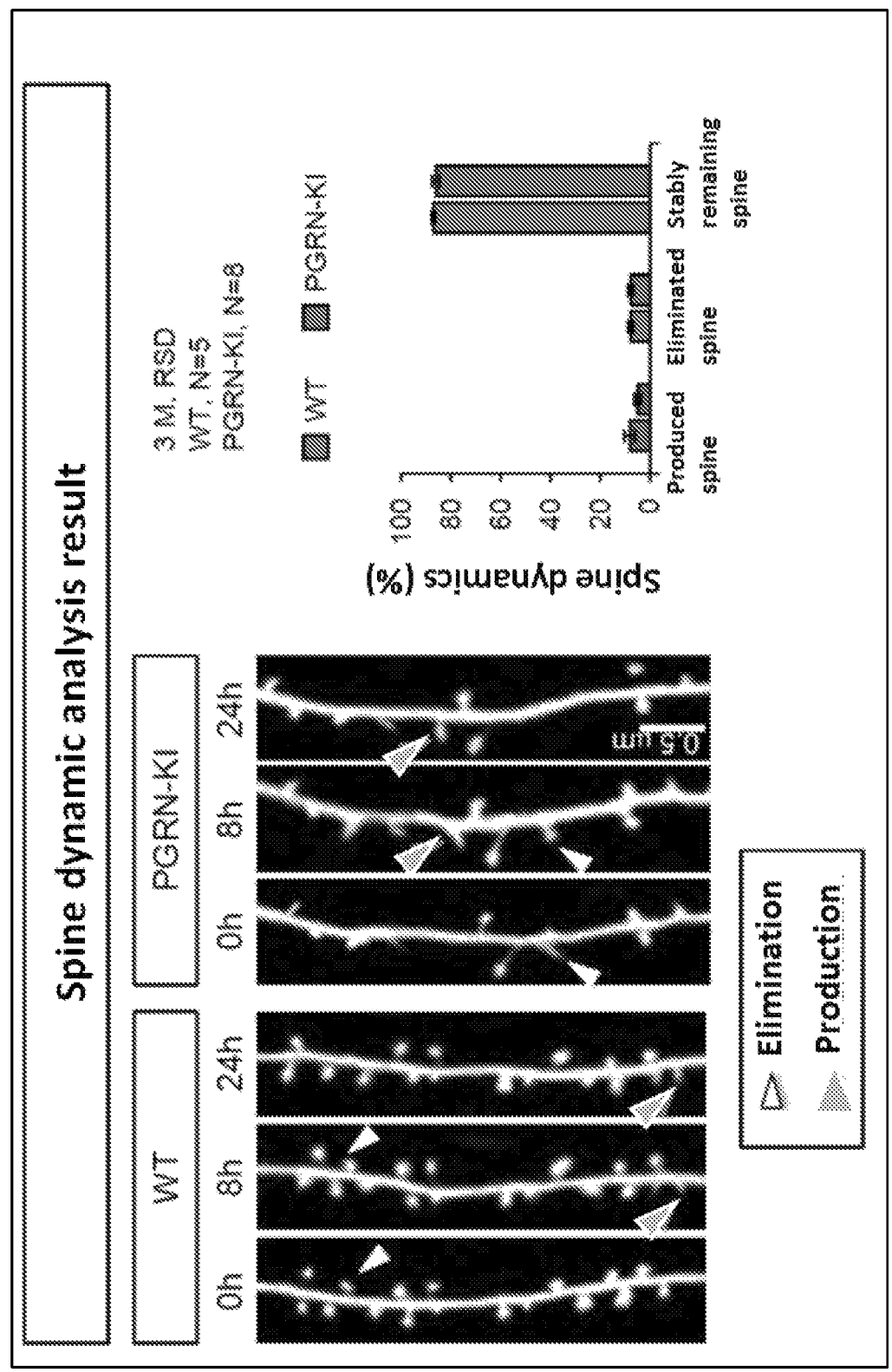
FIG. 30 is a figure for illustrating the result of spine dynamic analysis on the retrosplenial cortexes (RSD) of the FTLD model mice (PGRN-KI mice) and wild-type mice (WT). In the figure, the left panel shows photographs of spines observed with a two-photon microscope. In the photographs, the upward arrows indicate spines to be eliminated, and the downward arrows indicate produced spines. The right panel shows the number of spines produced, the number of spines eliminated, and the number of spines stably remaining detected by the two-photon microscope observation. Moreover, in each graph, the left bar shows the observation result of the wild-type mice, and the right bar shows the observation result of the PGRN-KI mice.

Concretely, EGFP-expressing AAV was injected into retrosplenial cortexes (RSD) of the PGRN-KI mice and the C57BL/6J mice. Then, two weeks thereafter, in vivo imaging was performed on synaptic spines with a two-photon microscope. FIGS. 29 and 30 show the obtained result.

As shown in FIG. 29, the result of the in vivo imaging on EGFP-positive nerve cells in layer 1 revealed that the spine density was remarkably reduced in the PGRN-KI mice. Note that the other spine parameters such as length, diameter, and volume were not much different from those of the C57BL/6J mice. These suggest that the reduction in the spine density is a phenotype requiring a comparatively long time.

Further, as shown in FIG. 30, the result of observing the spine dynamics at three time points showed that, consistently, the numbers of produced spines, eliminated spines, and stably remaining spines did not significantly change at any time point within 24 hours.

Figure 31:
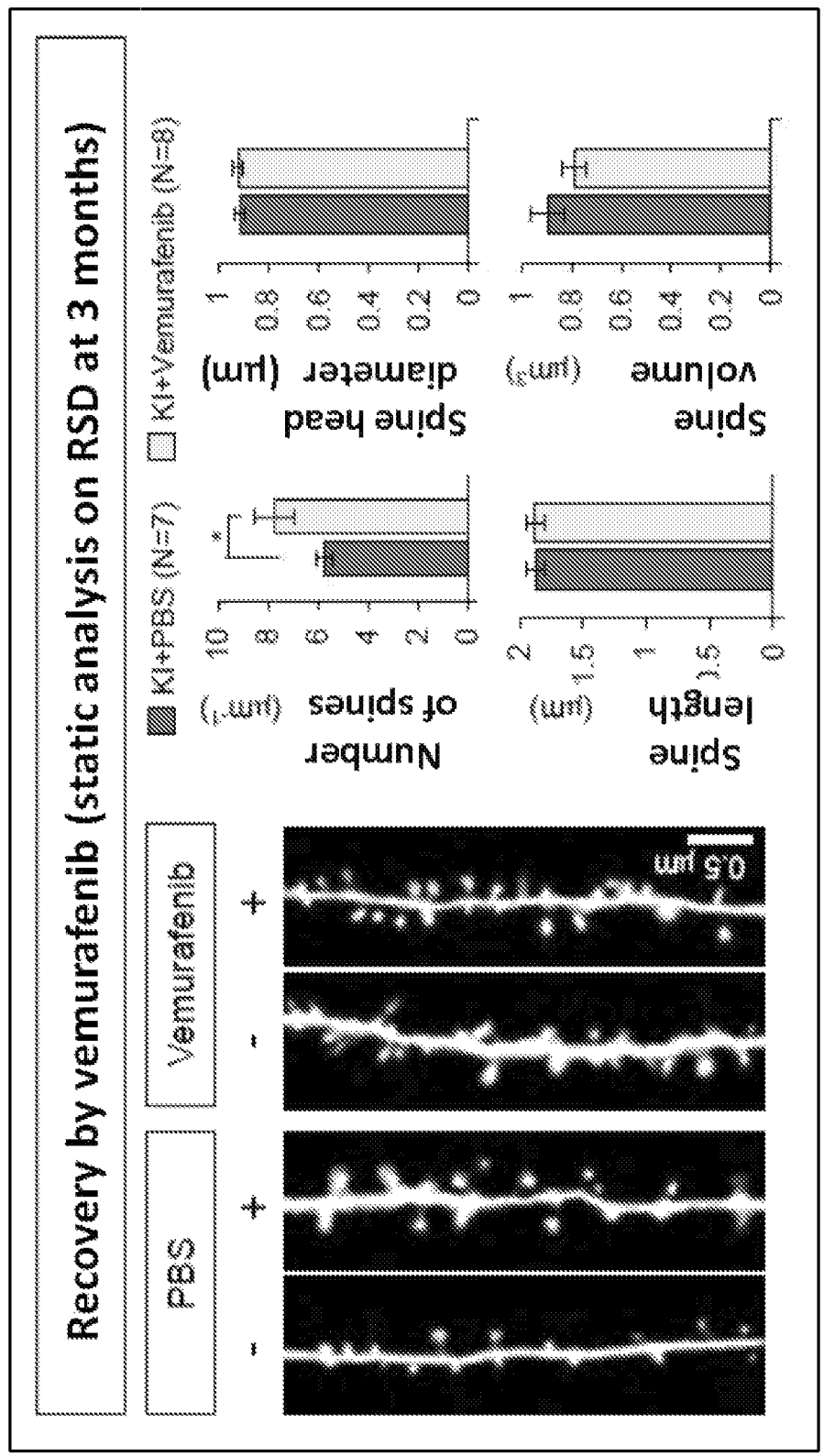
FIG. 31 is a figure for illustrating the result of spine static analysis on the retrosplenial cortexes (RSD) of the PGRN-KI mice (KI) to which the b-raf inhibitor (vemurafenib) or PBS was administered. In the figure, the left panel shows photographs of spines observed with a two-photon microscope. In the figure, graphs in the right panel show the number of spines (the number of spines per 1 μm of the dendrite), spine length, spine head diameter, and spine volume measured by the two-photon microscope observation. Moreover, in each graph, the left bar shows the observation result of the PBS-administered PGRN-KI mice (KI+PBS), and the right bar shows the observation result of the vemurafenib-administered PGRN-KI mice (KI+vemurafenib). In the figure, one asterisk indicates $p<0.05$ in Student's independent t-test.
Figure 32:
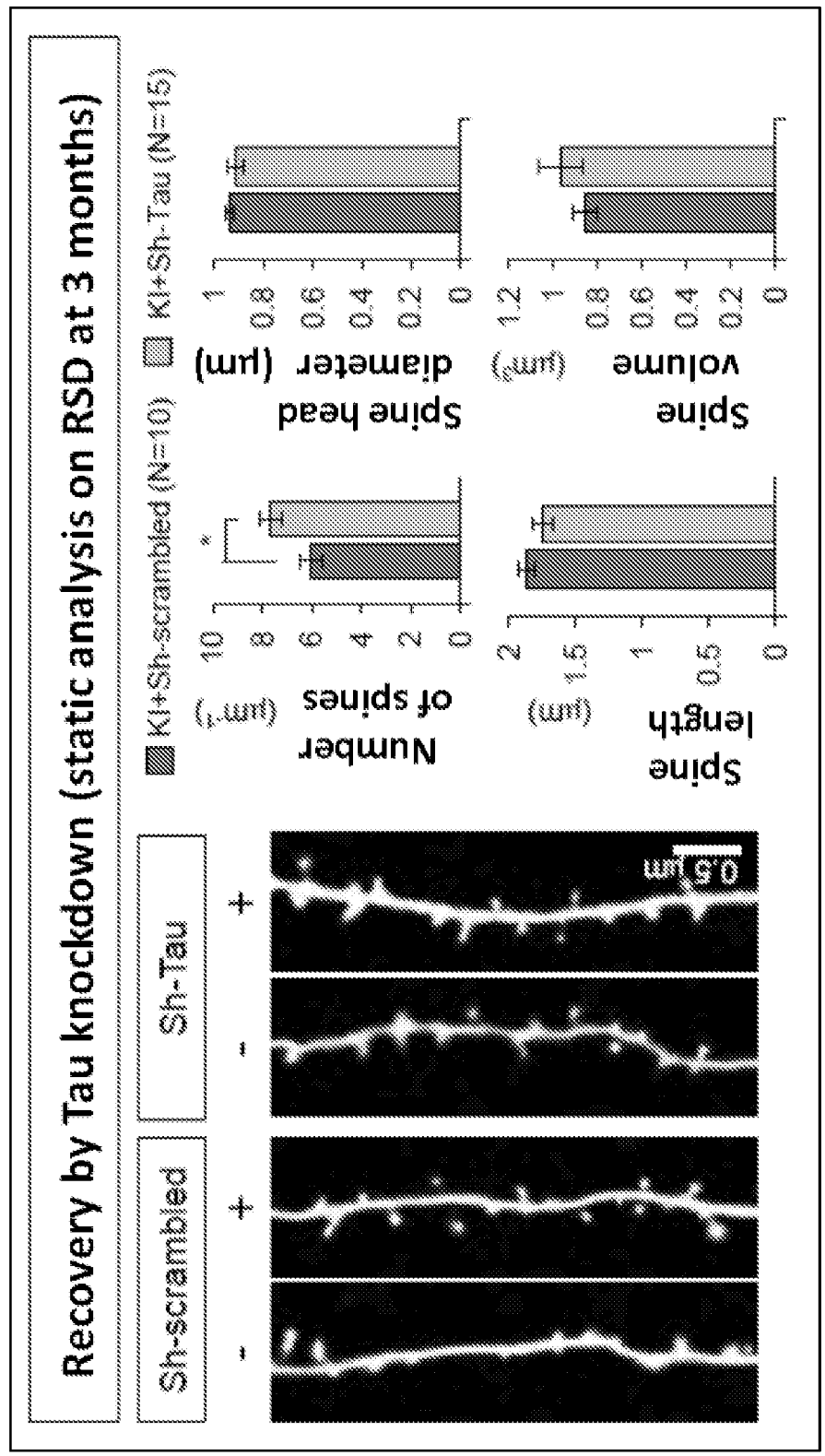
FIG. 32 is a figure for illustrating the result of spine static analysis on the retrosplenial cortexes (RSD) of the PGRN-KI mice (KI) in which shRNA against tau (Sh-Tau) or scrambled shRNA (Sh-scrambled) was injected. In the figure, the left panel shows photographs of spines observed with a two-photon microscope. In the figure, graphs in the right panel show the number of spines (the number of spines per 1 μm of the dendrite), spine length, spine head diameter, and spine volume measured by the two-photon microscope observation. Moreover, in each graph, the left bar shows the observation result of the scrambled shRNA-injected PGRN-KI mice (KI+Sh-scrambled), and the right bar shows the observation result of the Sh-Tau-injected PGRN-KI mice (KI+Sh-Tau). In the figure, one asterisk indicates $p<0.05$ in Student's independent t-test.

In addition, analyzed was whether or not vemurafenib and/or tau knockdown enabled recovery of spine related phenotype. FIGS. 31 and 32 show the obtained result.

As shown in FIG. 31, the observation result with a two-photon microscope revealed that administering vemurafenib using an osmotic pump recovered the number of spines of the PGRN-KI mice.

Moreover, as shown in FIG. 32, the in vivo recovery effect on the number of spines was observed as a result of knocking down Tau using a lentiviral vector expressing shRNA against tau (sh-tau).

As shown in FIGS. 31 and 32, the changes in synaptic spines were the same in the two treatments, but a slight difference was detected in the static spine morphology. To be more specific, a trend was observed that b-raf inhibition decreased the spine volume. On the other hand, the tau knockdown tended to increase the spine volume. This difference between the trends was conceivably because the spines increased by vemurafenib and sh-tau were thin spines in the former, but were thick spines in the latter. Nevertheless, as shown in FIGS. 31 and 32, the difference was not stably confirmed as a statistically significant difference.

Figure 33:
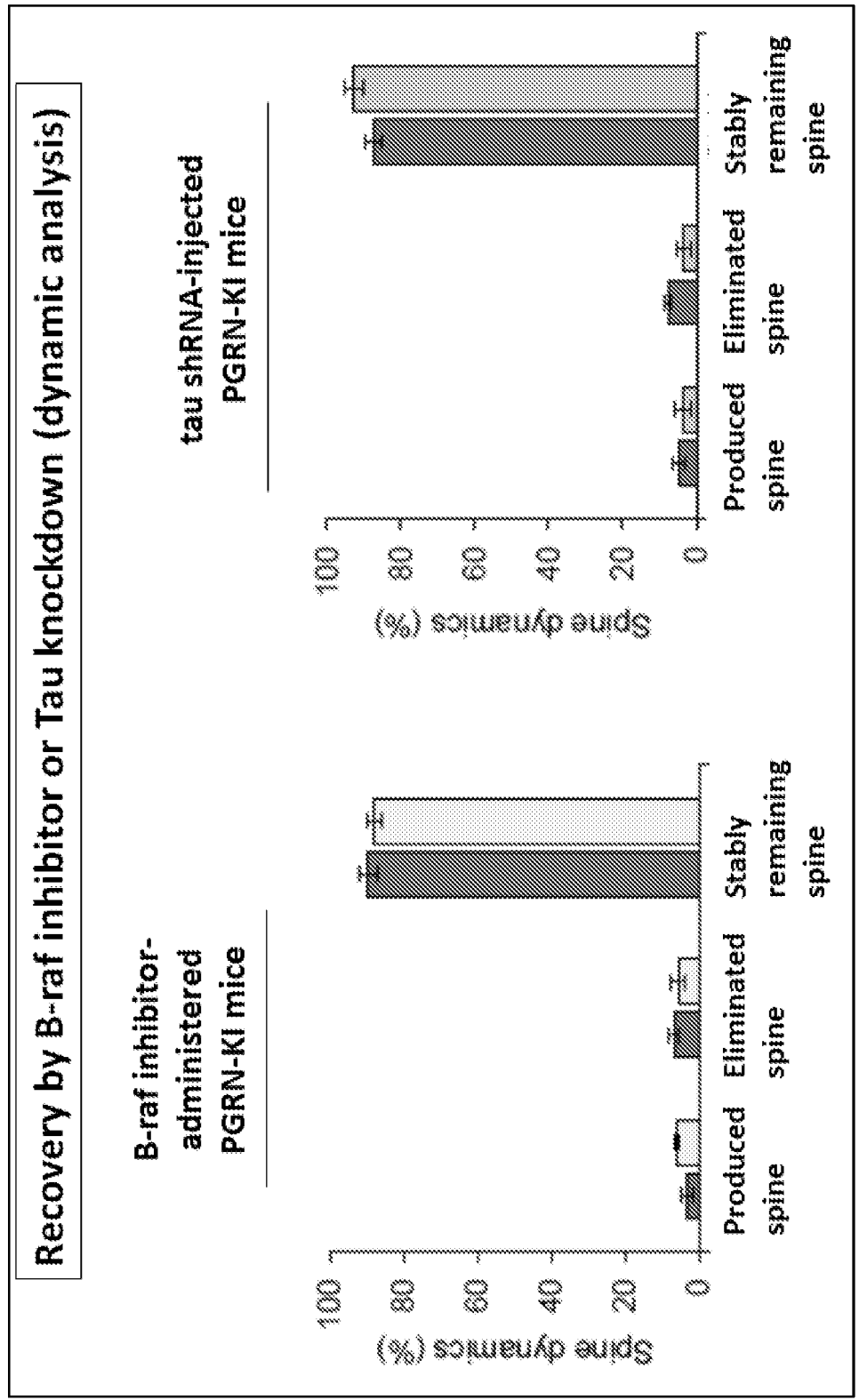
FIG. 33 shows graphs for illustrating the result of spine dynamics analysis on the retrosplenial cortexes of the FTLD model mice (PGRN-KI mice). In the figure, the left graph shows the result of administering vemurafenib to the PGRN-KI mice (the number of analyses: three mice, the left bars in the graph) or the result of administering PBS to the PGRN-KI mice (the number of analyses: four mice, the right bars in the graph). In the figure, the right graph shows the result of injecting scrambled shRNA into the PGRN-KI mice (the number of analyses: four mice, the left bars in the graph) or the result of injecting shRNA against tau into the PGRN-KI mice (the number of analyses: four mice, the right bars in the graph).

In addition, the spine dynamics were also observed. However, as shown in FIG. 33, no change was detected in spine production or elimination.

The above results revealed that the vemurafenib administration or tau knockdown had a recovery effect on the number of spines. Moreover, these results confirmed that activating the MAPK pathway including tau was a major mechanism of the abnormal behavior in the PGRN-KI mice.

INDUSTRIAL APPLICABILITY

As has been described above, it has been revealed that, in the pre-onset stage of Alzheimer's disease, stepwise enhancement of the phosphorylation of the AD core network composed of MARCKS, Marcksl1, SRRM2, SPTA2, ADDB, NEUM, BASP1, SYT1, G3P, HS90A, CLH, NFH, NFL, GPRIN1, ACON, ATPA, and ATPB affects dendritic spine dynamics and the like, consequently developing Alzheimer's disease. Moreover, it has also been revealed that the phosphorylation of the AD core network is caused by PKC, CaMK, CSK, and Lyn, and further that b-raf is involved in the promotion of the transition from amyloid pathology to tau pathology (enhancement of the phosphorylation of the tau protein) important for the progression of Alzheimer's disease.

Thus, the present invention targets the proteins composing the AD core network and kinases which phosphorylate these proteins, and is useful in providing early-stage diagnosis and treatment methods against Alzheimer's disease and agents utilizable in the se methods.

In addition, regarding frontotemporal lobar degeneration (FTLD) also, it has been revealed that TNF-related signal transduction pathways, particularly a MAPK signal transduction pathway, are activated from a pre-onset stage of the disease, and that the activation decreases the number of synaptic spines in FTLD patients, consequently developing abnormal behaviors and the like.

Thus, the present invention targets b-RAF belonging to the MAPK signal transduction pathway, and is useful in providing diagnosis and treatment methods against FTLD and agents utilizable in these methods.

The invention claimed is:

1. A method for diagnosing and treating pre-onset Alzheimer's disease, or diagnosing and treating a risk of developing Alzheimer's disease, the method comprising:
    (i) detecting, in a test subject, an increased phosphorylation level of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB, by detecting the level of phosphorylation of said at least one substrate protein in said subject as being higher than the level of phosphorylation of said at least one substrate protein in a normal subject;
    (ii) determining that the test subject is affected with pre-onset Alzheimer's disease, or has a risk of developing Alzheimer's disease, following the detection of the increased phosphorylation level of said at least one substrate protein in said test subject; and
    (iii) administering a treatment to the test subject determined as being affected with pre-onset Alzheimer's disease, or having a risk of developing Alzheimer's disease in step (ii), wherein
    the treatment is administering an agent comprising a peptide having a dominant negative effect on the phosphorylation of MARCKS, wherein said peptide comprises a fragment of MARCKS containing a phosphorylation site.

2. The method according to claim 1, wherein the level of phosphorylation is detected by enzyme immunoassay, positron emission tomography, or mass spectrometry.

3. A method for diagnosing pre-onset Alzheimer's disease, the method comprising:
    (i) detecting, in a test subject, an increased phosphorylation level of at least one substrate protein selected from the group consisting of MARCKS, Marcksl1, SRRM2, SPTA2, ADDB, NEUM, BASP1, SYT1, G3P, HS90A, CLH, NFH, NFL, GPRIN1, ACON, ATPA, and ATPB, by detecting the level of phosphorylation of said at least one substrate protein in said subject as being higher than the level of phosphorylation of said at least one substrate protein in a normal subject;
    (ii) determining that the test subject is affected with:
    an initial phase of pre-onset Alzheimer's disease following detection of increased phosphorylation level at least one substrate protein selected from the group consisting of MARCKS, Marcksl1, and SRRM2, in said test subject,
    a mid-phase of pre-onset Alzheimer's disease following detection of increased phosphorylation level at least one substrate protein selected from the group consisting of SPTA2, ADDB, NEUM, BASP1, SYT1, G3P, and HS90A, in said test subject, or
    a late phase of pre-onset Alzheimer's disease following detection of increased phosphorylation level at least one substrate protein selected from the group consisting of CLH, NFH, NFL, and GPRIN1, in said test subject; and
    (iii) performing diagnostic brain imaging on the test subject determined in step (ii) as being affected with pre-onset Alzheimer's disease, wherein said diagnostic brain imaging is selected from the group consisting of CT, MRI, PET and SPECT.

* * * * *